US008889826B2

(12) United States Patent
Leese et al.

(10) Patent No.: US 8,889,826 B2
(45) Date of Patent: Nov. 18, 2014

(54) PEPTIDE ANTIBIOTICS AND METHODS FOR MAKING SAME

(75) Inventors: Richard A. Leese, Suffern, NY (US); Noreen Francis, Suffern, NY (US); William V. Curran, Pearl River, NY (US); Donald B. Borders, Suffern, NY (US); Howard Jarolmen, Township of Washington, NJ (US)

(73) Assignee: BioSource Pharm, Inc., Spring Valley, NY (US)

( * ) Notice: Subject to any disclaimer, the term of this patent is extended or adjusted under 35 U.S.C. 154(b) by 1510 days.

(21) Appl. No.: 11/630,847

(22) PCT Filed: Jul. 1, 2005

(86) PCT No.: PCT/US2005/023343
§ 371 (c)(1),
(2), (4) Date: Jan. 3, 2008

(87) PCT Pub. No.: WO2006/083317
PCT Pub. Date: Aug. 10, 2006

(65) Prior Publication Data
US 2008/0207874 A1     Aug. 28, 2008

Related U.S. Application Data

(60) Provisional application No. 60/813,587, filed on Jul. 1, 2004.

(51) Int. Cl.
| C07K 7/62 | (2006.01) |
| C07K 7/64 | (2006.01) |
| A61K 38/00 | (2006.01) |
| A61K 38/12 | (2006.01) |
| C07K 5/09 | (2006.01) |
| C07K 5/068 | (2006.01) |

(52) U.S. Cl.
CPC .............. C07K 5/0815 (2013.01); C07K 7/65 (2013.01); C07K 7/64 (2013.01); A61K 38/00 (2013.01); C07K 5/06086 (2013.01)
USPC ............. 530/319; 530/317; 514/2.2; 514/2.3; 514/2.8; 514/2.9; 514/3.6; 514/21.1; 514/21.6

(58) Field of Classification Search
CPC ........ C07K 7/62; C07K 7/64; C07K 5/06086; C07K 5/0815; A61K 38/00; A61K 38/12
USPC .............. 530/319, 317; 514/2.2, 2.3, 2.8, 2.9, 514/21.1, 21.6
See application file for complete search history.

(56) References Cited

U.S. PATENT DOCUMENTS

| 3,753,970 A | 8/1973 | Bouchaudon et al. |
| 3,817,973 A | 6/1974 | Bouchaudon et al. |
| 3,854,480 A | 12/1974 | Zaffaroni |
| 4,091,092 A | 5/1978 | Park et al. |
| 4,399,067 A | 8/1983 | Debono et al. |
| 4,452,775 A | 6/1984 | Kent |
| 4,482,487 A | 11/1984 | Abbott et al. |
| 4,510,132 A | 4/1985 | Vaara et al. |
| 4,524,135 A | 6/1985 | Abbott et al. |
| 4,526,938 A | 7/1985 | Churchill et al. |
| 4,537,717 A | 8/1985 | Abbott et al. |
| 4,601,893 A | 7/1986 | Cardinal |
| RE32,310 E | 12/1986 | Debono |
| RE32,311 E | 12/1986 | Debono |
| 4,767,628 A | 8/1988 | Hutchinson |
| 4,830,860 A | 5/1989 | Ranade |
| 4,874,850 A | 10/1989 | Paradies |
| 4,895,566 A | 1/1990 | Lee |
| 4,942,035 A | 7/1990 | Churchill et al. |
| 5,004,602 A | 4/1991 | Hutchinson |
| 5,028,590 A | 7/1991 | Fukuda et al. |
| 5,039,789 A | 8/1991 | Fukuda et al. |
| 5,041,567 A | 8/1991 | Rogers et al. |
| 5,082,653 A | 1/1992 | Pan et al. |
| 5,112,614 A | 5/1992 | Magruder et al. |
| 5,239,660 A | 8/1993 | Ooi |
| 5,254,535 A | 10/1993 | Zaslof et al. |
| 5,283,005 A | 2/1994 | Nelson, Jr. et al. |
| 5,360,788 A | 11/1994 | Nelson |
| 5,366,734 A | 11/1994 | Hutchinson |

(Continued)

FOREIGN PATENT DOCUMENTS

| EP | 1 360 961 A1 | 11/2003 |
| JP | 2003-505042 | 2/2003 |

(Continued)

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*

(Continued)

*Primary Examiner* — Julie Ha
(74) *Attorney, Agent, or Firm* — Hamilton, Brook, Smith & Reynolds, P.C.

(57) ABSTRACT

Disclosed herein are novel peptides and protected peptides. These compounds can be derived from naturally occurring peptides, such as those selected from colistin, circulin A, polymyxin A, polymyxin B, polymyxin D, octapeptin B, octapeptin C, and [Ile$^7$]polymyxin B$_1$. Also disclosed are pharmaceutical compositions containing the new peptides, as well as methods for preparing the novel peptides and protected peptides.

64 Claims, No Drawings

(56) References Cited

U.S. PATENT DOCUMENTS

| | | | |
|---|---|---|---|
| 5,424,290 A | 6/1995 | Maloy et al. |
| 5,459,237 A | 10/1995 | Berkowitz et al. |
| 5,470,950 A | 11/1995 | Maloy et al. |
| 5,565,423 A | 10/1996 | Sandow et al. |
| 5,587,358 A | 12/1996 | Sukigara et al. |
| 5,616,557 A | 4/1997 | Tsuchiya et al. |
| 5,620,954 A | 4/1997 | Maloy |
| 5,635,216 A | 6/1997 | Thompson |
| 5,654,451 A | 8/1997 | Kari |
| 5,660,847 A | 8/1997 | Magruder et al. |
| 5,686,065 A | 11/1997 | Haney |
| 5,725,875 A | 3/1998 | Noll et al. |
| 5,755,788 A | 5/1998 | Strauss |
| 5,776,919 A | 7/1998 | Sukigara et al. |
| 5,849,761 A | 12/1998 | Yaksh |
| 5,856,438 A | 1/1999 | Little, II |
| 5,891,914 A | 4/1999 | Haney |
| 6,004,573 A | 12/1999 | Rathi et al. |
| 6,011,008 A | 1/2000 | Domb et al. |
| 6,153,730 A | 11/2000 | Little |
| 6,180,134 B1 | 1/2001 | Zalipsky et al. |
| 6,228,834 B1 | 5/2001 | Little |
| 6,348,445 B1 | 2/2002 | Kari et al. |
| 6,350,438 B1 | 2/2002 | Witt et al. |
| 6,350,738 B1 | 2/2002 | Savage et al. |
| 6,380,356 B1 | 4/2002 | Griffin et al. |
| 6,440,690 B1 | 8/2002 | Mor et al. |
| 6,468,967 B1 | 10/2002 | Oleson, Jr. et al. |
| 6,495,516 B1 | 12/2002 | Little, II et al. |
| 6,511,962 B1 | 1/2003 | Borders et al. |
| 6,515,104 B1 | 2/2003 | Little, II et al. |
| 6,846,478 B1 | 1/2005 | Doyle et al. |
| 7,053,044 B1 | 5/2006 | Curstedt et al. |
| 7,364,747 B1 | 4/2008 | Haas |
| 7,541,046 B1 | 6/2009 | Sung et al. |
| 8,343,912 B2 | 1/2013 | Leese |
| 8,415,307 B1 | 4/2013 | Curran et al. |
| 2001/0021697 A1 | 9/2001 | Lowenstein et al. |
| 2002/0019376 A1 | 2/2002 | Savage et al. |
| 2002/0091278 A1 | 7/2002 | Savage et al. |
| 2002/0123520 A1 | 9/2002 | Marfat et al. |
| 2002/0150964 A1 | 10/2002 | Mor et al. |
| 2003/0055028 A1 | 3/2003 | Stergiopoulos et al. |
| 2003/0111075 A1 | 6/2003 | Wen |
| 2003/0114724 A1 | 6/2003 | Boss |
| 2003/0144195 A1 | 7/2003 | Little, II et al. |
| 2003/0202974 A1 | 10/2003 | Willnow |
| 2003/0224475 A1 | 12/2003 | Leese et al. |
| 2004/0023884 A1 | 2/2004 | Little, II |
| 2004/0024179 A1 | 2/2004 | Little, II |
| 2004/0048793 A1 | 3/2004 | Little, II et al. |
| 2005/0032765 A1 | 2/2005 | Savage et al. |
| 2005/0079200 A1 | 4/2005 | Rathenow et al. |
| 2005/0163727 A1 | 7/2005 | Doyle et al. |
| 2005/0260186 A1 | 11/2005 | Bookbinder et al. |
| 2005/0277577 A1 | 12/2005 | Hunter et al. |
| 2006/0093597 A1 | 5/2006 | Zhu |
| 2006/0104968 A1 | 5/2006 | Bookbinder et al. |
| 2006/0120977 A1 | 6/2006 | Friedman et al. |
| 2006/0195183 A1 | 8/2006 | Navia et al. |
| 2006/0259135 A1 | 11/2006 | Navia et al. |
| 2007/0038296 A1 | 2/2007 | Navia et al. |
| 2007/0060558 A1 | 3/2007 | Sanchez et al. |
| 2007/0196421 A1 | 8/2007 | Hunter et al. |
| 2007/0197658 A1 | 8/2007 | David et al. |
| 2007/0197957 A1 | 8/2007 | Hunter et al. |
| 2007/0203080 A1 | 8/2007 | Lipshutz |
| 2007/0207186 A1 | 9/2007 | Scanlon et al. |
| 2007/0208134 A1 | 9/2007 | Hunter et al. |
| 2007/0243275 A1 | 10/2007 | Gilbard |
| 2007/0254833 A1 | 11/2007 | Hunter et al. |
| 2007/0299043 A1 | 12/2007 | Hunter et al. |
| 2008/0009902 A1 | 1/2008 | Hunter et al. |
| 2008/0241275 A1 | 10/2008 | Perl et al. |
| 2008/0279820 A1 | 11/2008 | Hicks et al. |
| 2008/0287345 A1 | 11/2008 | Vaara et al. |
| 2009/0017075 A1 | 1/2009 | Van Nest et al. |
| 2009/0048155 A1 | 2/2009 | Wilson |
| 2009/0118168 A1 | 5/2009 | Dinh et al. |
| 2009/0123367 A1 | 5/2009 | Bookbinder et al. |
| 2009/0177262 A1 | 7/2009 | Oberti et al. |
| 2009/0214601 A1 | 8/2009 | Chappa et al. |
| 2009/0215677 A1 | 8/2009 | Vaara et al. |
| 2009/0226964 A1 | 9/2009 | Park et al. |
| 2009/0239792 A1 | 9/2009 | Vaara et al. |
| 2009/0247458 A1 | 10/2009 | Watson et al. |
| 2009/0264342 A1 | 10/2009 | Cottarel et al. |
| 2009/0318403 A1 | 12/2009 | De Visser et al. |
| 2010/0028334 A1 | 2/2010 | Cottarel et al. |
| 2010/0029597 A1 | 2/2010 | Cottarel et al. |
| 2010/0160215 A1 | 6/2010 | Leese |

FOREIGN PATENT DOCUMENTS

| | | |
|---|---|---|
| WO | WO 95/05384 | 2/1995 |
| WO | WO 95/30417 | 11/1995 |
| WO | WO 01/05815 A1 | 1/2001 |
| WO | WO 01/44271 | 6/2001 |
| WO | WO 01/44272 | 6/2001 |
| WO | WO 01/44274 | 6/2001 |
| WO | WO 02/05837 A1 | 1/2002 |
| WO | WO 02/05838 | 1/2002 |
| WO | WO 02/055543 A2 | 7/2002 |
| WO | WO 02/055543 A3 | 7/2002 |
| WO | WO 03/014147 | 2/2003 |
| WO | WO 2006/083317 A2 | 8/2006 |
| WO | WO 2008/017734 A1 | 2/2008 |
| WO | WO 2010/075416 A1 | 7/2010 |

OTHER PUBLICATIONS

Katz M, Tsubery H, Kolusheva S, Shames A, Fridkin M, Jelinek R, "Lipid binding and membrane penetration of polymyxin B derivatives studied in a biomimetic vesicle system," Biochem. J., 2003, 375: 405-413.*

Barnett, M. et al. "Sodium Sulphomethyl Derivatives of Polymyxins" *Br. J. Pharmacol.* 23:552-574 (1964).

Clausell, A. et al. "Synthesis and Membrane Action of Polymyxin B Analogues" *Luminescence* 20:117-123 (2005).

Clausell, A. et al. "Membrane Association and Contact Formation by a Synthetic Analogue of Polymyxin B and Its Fluorescent Derivatives" *J. Phys. Chem. B* 110:4465-4471 (2006).

Frecer, V. et al. "De Novo Design of Potent Antimicrobial Peptides" *Antimicrob. Agents Chemother.* 48(9):3349-3357 (2004).

Kanazawa, K. et al. "Contribution of Each Amino Acid Residue in Polymyxin $B_3$ to Antimicrobial and Lipopolysaccharide Binding Activity" *Chem. Pharm. Bull.* 57(3):240-244 (2009).

Katsuma, N. et al. "Development of Des-Fatty Acyl-Polymyxin B Decapeptide Analogs with *Pseudomonal aeruginosa*-Specific Antimicrobial Activity" *Chem. Pharm. Bull.* 57(4):332-336 (2009).

Kristensen, H.K. et al. "Separation of Polymyxins by Micellar Electrokinetic Capillary Chromatography" *J. Chromatography* 628:309-315 (1993).

Li, C. et al. "Incremental Conversion of Outer-Membrane Permeabilizers into Potent Antibiotics for Gram-Negative Bacteria" *J. Am. Chem. Soc.* 121:931-940 (1999).

Molina, J. et al. "New Information about the Polymyxin/Colistin Class of Antibiotics" *Expert Opin. Pharmacother.* 10(17):2811-2828 (2009).

O'Dowd, H. et al. "Preparation of Tetra-Boc-Protected Polymyxin B Nonapeptide" *Tetrahedron Lett.* 48:2003-2005 (2007).

Okimura, K. et al. "Chemical Conversion of Natural Polymyxin B and Colistin to Their *N*-Derivatives" *Bull. Chem. Soc. Jpn.* 80(3):543-552 (2007).

Okimura, K. et al. "Semi-synthesis of Polymyxin B (2-10) and Colistin (2-10) Analogs Employing the Trichloroethoxycarbonyl (Troc) Group for Side Chain Protection of α, γ-Diaminobutyric Acid Residues" *Chem. Pharm. Bull.* 55(12):1724-1730 (2007).

Orwa, J.A. et al. "Isolation and Structural Characterization of Polymyxin B Components" *J. Chromatography A* 912:369-373 (2001).

(56) References Cited

OTHER PUBLICATIONS

Orwa, J.A. et al. "Isolation and Structural Characterization of Colistin Components" *J. Antibiotics* 54(7):595-599 (2001).
Puar, M.S. "Carbon-13 NMR Studies of EM49 and Related Octapeptins" *J. Antibiotics* 33:760-763 (1980).
Rosenthal, K.S. et al. "Mechanism of Action of EM 49, Membrane-Active Peptide Antibiotic" *Antimicrob. Agents Chemother.* 12(6):665-672 (1977).
Rustici, A. et al. "Molecular Mapping and Detoxification of the Lipid A Binding Site by Synthetic Peptides" *Science* 259:361-365 (1993).
Shoji, J. et al. "Isolation of Two New Polymyxin Group Antibiotics (Studies on Antibiotics from the Genus *Bacillus*. XX)" *J. Antibiot.* 30:1029-1034 (1977).
Shoji, J. et al. "The Structure of Polymyxin $S_1$ (Studies on Antibiotics from the Genus *Bacillus*. XXI)" *J. Antibiot.* 30(12):1035-1041 (1977).
Sil, D. et al. "Bound to Shock: Protection from Lethal Endotoxemic Shock by a Novel, Nontoxic, Alkylpolyamine Lipopolysaccharide Sequestrant" *Antimicrob. Agents Chemother.* Published online ahead of print on Jun. 4, 2007, pp. 1-32; retrieved from the Internet at www.aac.asm.org on Dec. 1, 2009.
Srinivasa, B.R. et al. "Chemical Modification of Peptide Antibiotics: Part VI—Biological Activity of Derivatives of Polymyxin B" *Indian J. Biochem. Biophys.* 14:54-58 (1978).
Sugawara, K. et al. "Bu-2470, a New Peptide Antibiotic Complex. II. Structure Determination of Bu-2470 $A_1$ $B_1$, $B_{2a}$ and $B_{2b}$," *J. Antibiot.* 36:634-638 (1983).
Tueber, M. "Preparation of biologically active mono-$N$-acetyl($^{14}$C)-derivatives of the membrane-specific polypeptide antibiotic polymyxin B" *Z. Naturforsch.* 25b:117 (1970).
Tsubery, H. et al. "Structure-Function Studies of Polymyxin B Nonapeptide: Implications to Sensitization of Gram-Negative Bacteria" *J. Med. Chem.* 43:3085-3092 (2000).
Tsubery, H. et al. "Modulation of the Hydrophobic Domain of Polymyxin B Nonapeptide: Effect on Outer-Membrane Permeabilization and Lipopolysaccharide Neutralization" *Mol. Pharmacol.* 62(5):1036-1042 (2002).
Tsubery, H. et al. "Neopeptide Antibiotics That Function as Opsonins and Membrane-Permeabilizing Agents for Gram-Negative Bacteria" *Antimicrob. Agents Chemother.* 49(8):3122-3128 (2005).
Vaara, M. "The Outer Membrane Permeability-Increasing Action of Linear Analogues of Polymyxin B Nonapeptide" *Drugs Exptl. Clin. Res.* 17(9):437-444 (1991).
Vaara, M. et al. "Novel Polymyxin Derivatives Carrying Only Three Positive Charges Are Effective Antibacterial Agents" *Antimicrob. Agents Chemother.* Published online ahead of print on Jun. 30, 2008, pp. 1-31; retrieved from the Internet at www.aac.asm.org on Dec. 1, 2009.
Vogler, K. et al. "The Chemistry of the Polymyxin Antibiotics" *Experientia* 22(6):345-416 (1966).
Choi et al., "Identification of a Polymyxin Synthetase Gene Cluster of *Paenibacillus polymyxa* and Heterologous Expression of the Gene in *Bacillus subtilis*", Journal of Bacteriology, May 2009, vol. 191, No. 10, p. 3350-3358.
Barrett, et al. "Edman Stepwise degradation of polypeptides: a new strategy employing mild basic cleavage conditions" *Tetrahedron Letters* 26(36):4375-4378 (1985).
Berge, et al. "Pharmaceutical salts" *J. Pharm. Sci.* 66:1-19 (1977).
Boeck, et al. "Deacylation of A21978C, an acidic Lipopeptide Antibiotic Complex, by *Actinoplanes utahensis*" *J. Antibiot.* 41(8):1085-1092 (1988).
Boeck, et al. "Deacylation of Echinocandin B by *Actinoplanes utahensis*" *J. Antibiot.* 42(3):382-388 (1989).
Brandt, et al. "Abnormal behaviour of proline in the isothiocyanate degradation" *Z. Physiol. Chem.* 357:1505-1508 (1976).
Chihara, et al. "Chemical Synthesis and Characterization of α-N-Octanoyl and Other α-N-Acyl Nonapeptide Derivatives" *Agr. Biol. Chem.* 37(12): 2709-2717 (1973).
Chihara, et al. "Chemical synthesis, isolation, and characterization of α-N-fattyacyl colistin nonapeptide with special reference to the correlation between antimicrobial activity and carbon number of fattyacyl moiety" *Agr. Biol. Chem.* 38(3):521-529 (1974).
Chihara, et al. "Chemical Synthesis and Characterization of n-Fattyacyl Mono-Aminoacyl Derivatives of Colistin Nonapeptide" *Agr. Biol. Chem.* 38(10): 1767-1777 (1974).
De Visser, et al. "Solid-phase synthesis of polymyxin B1 and analogues via a safety-catch approach" *J. Pept. Res.* 61(6):298-306 (Jun. 2003).
Duwe, et al. "In Vitro Cytotoxicity and Antibiotic Activity of Polymyxin B Nonapeptide" *Antimicrob. Agents Chemother* 30:340-341 (1986).
Elverdam, et al. "Isolation and Characterization of Three New Polymyxins in Polymyxins B and E by High-Performance Liquid Chromatography" *J. Chromatogr.* 218: 653-661 (1981).
Evans, et al, "Polymyxin B Sulfate and Colistin: Old Antibiotics for Emerging Multiresistant Gram-Negative Bacteria" *Ann. Pharmacother* 33:960-967 (1999).
Falagas, et al. "Colistin: The Revival of Polymyxins for the Management of Multidrug-Resistant Gram-Negative Bacterial Infections" *Rev. Anti-Infect. Agents.* 40:1333-1341 (2005); Erratum *Rev. Anti-Infect. Agents* 42:1819 (2006).
Fostel, et al, "Emerging novel antifungal agent" *Drug Discovery Today* 5:25-32 (2000).
Gershonov, et al. "A Novel Approach for a Water-Soluble Long-Acting Insulin ProDrug: Design, Preparation, and Analysis of [(2-Sulfo)-9-Fluorenylmethoxycarbonyl]$_3$-Insulin" *J. Med. Chem.* 43(13):2530-2537 (2000).
Han, et al. "Dégradation récurrente d'Edman" *Biochemie* 59:557-576 (1977).
Han, et al. "Current developments in stepwise Edman degradation of peptides and proteins" *Int. J. Biochem.* 17(4):429-445 (1985).
Hausmann, et al. "Polymyxin B1. Fractionation, molecular weight determination, amino acid and fatty acid composition" *J. Am. Chem. Soc.* 76:4892-4896 (1954).
International Search Report issued by the International Searching Authority on Dec. 6, 2006 in PCT/US2005/023343.
Jarolmen, et al. "Activity of Minocycline Against R-Factor Carrying *Enterobacteriaceae*" *Infect. Immun.* 1(4):321-326 (1970).
Kato, et al. "The Structure of Octapeptin D (Studies on Antibiotics from the Genus *Bacillus*. XXVIII)" *J. Antibiotics* 33(2):186-191 (Feb. 1980).
Kimura, et al. "Polymyxin acylase: purification and characterization, with special reference to broad substrate specificity" *Agr. Biol. Chem* 53(2):497-504 (1989).
Kimura, et al. "Polymyxin B Octapeptide and Polymyxin B Heptapeptide are Potent Outer Membrane Permeability-Increasing Agents" *J. Antibiot.* 45:742-749 (1992).
Kleinkauf, H. et al. "Nonribosomal biosynthesis of peptide antibiotics" *Eur. J. Biochem.* 192:1-15 (1990).
Kline, et al. "Synthesis and characterization of the colistin peptide polymyxin E1 and related antimicrobial peptides" *J. Pept. Res.* 57(3):175-187 (Mar. 2001).
Kreuzman, et al. "Membrane-associated echinocandin B deacylase of *Actinoplanes utahensis*: purification, characterization, heterologous cloning and enzymatic deacylation reaction" *J. Ind. Microbiol. Biotechnol.* 24(3):173-180 (Mar. 2000).
Kurihara, et al. "Studies on the compounds related to colistin. V. Synthesis and pharmacological activity of colistin analogues" *Yakugaku Zasshi* 92:129-134 (1972).
Liu et al. "A novel fmoc-based anchorage for the synthesis of protected peptide on solid phase" *Int. J. Pept. Protein Res.* 35:95-98 (1990).
Markou, et al. "Intravenous colistin in the treatment of sepsis from multiresistant Gram-negative bacilli in critically ill patients" *Critical Care* 7:R78-R83 (2003).
Martin, et al. "Isolation, structural characterization, and properties of mattacin (polymyxin M), a cyclic peptide antibiotic produced by *Paenibacillus kobensis* M" *J. Biol. Chem.* 278:13124-13132 (2003).
McCallister, et al. "Antimicrobial properties of liposomal polymyxin B" *J. Antimicrob. Chemother.* 43:203-210 (1999).
Merrifield, et al. "9-(2-sulfo)fluorenylmethyloxycarbonyl chloride, a new reagent for the purification of synthetic peptides" *J. Org. Chem.* 43(25):4808-4816 (1978).

(56) References Cited

OTHER PUBLICATIONS

Mutter et al. "A New Base-Labile Anchoring Group for Polymer-Supported Peptide Synthesis" *Helv. Chim. Acta* 67:2009 (1984).
Nakajima "Structure-activity relationship of colistins" *Chem. Pharm. Bull.* 15(8):1219-1224 (Aug. 1967).
Parker, et al. "EM49: A New Peptide Antibiotic IV. The Structure of EM49" *J. Antibiot.* 28(5):379-389 (1975).
Sakura, et al. "The Contribution of the N-Terminal Structure of Polymyxin B Peptides to Antimicrobial and Lipopolysaccharide Binding Activity" *Bull. Chem. Soc. Jpn.* 77:1915-1924 (2004).
Salem, et al. "Synthesis of Pelargonoyl-Cyclic Decapeptide Analog of the Antibiotic Polymyxin $B_1$" *Pharmazie* 35:540-541 (1980).
Shechter, et al. "Prolonging the half-life of human interferon-$\alpha_2$ in circulation: Design, preparation, and analysis of (2-sulfo-9-fluorenylmethoxycarbonyl)$_7$-interferon-$\alpha 2$" *Proc. Natl. Acad. Sci., U.S.A.* 98: 1212-1217 (2001).
Schechter, et al. "N-[(2-Sulfo)-9-Fluorenylmethoxycarbonyl]$_3$-gentamicin Is a Long-Acting Prodrug Derivative" *J. Med. Chem.* 45(19):4264-4270 (2002).
Shechter, et al. "Suspensions of pro-drug insulin greatly prolong normoglycemic patterns in diabetic rats" *Biochem. Biophys. Res. Commun.* 307(2):315-321 (Jul. 25, 2003).
Srinivasa, et al. "Essential Amino Groups of Polymyxin B" *Indian J. Biochem. Biophys.* 17:112-118 (1980).
Storm, et al. "Polimixin and related peptide antibiotics" *Ann. Rev. Biochem.* 46:723-763 (1977).
Takeshima, et al. "A deacylation enzyme for Aculeacin A, a neutral lipopeptide antibiotic, from *Actinoplanes utahensis*: purification and characterization" *J. Biochem.* 105(4):606-610 (1989).
Tarr "Improved manual sequencing methods" *Methods Enzymol.* 47:335-357 (1977).
Tsubery, et al. "N-Terminal Modifications of Polymyxin B Nonapeptide and Their Effect on Antibacterial Activity" *Peptides* 22:1675-1681 (2001).
Weinstein et al., "Selective Chemical Modifications of Polymyxin B," *Bioorg. Med. Chem. Lett.* 8:3391-3396 (1998).
Castanheira M. et al. "Antimicrobial susceptibility patterns of KPC-producing or CTX-M-producing Enterobacteriaceae,"Microb. Drug Resist.16:61-65 (2010).
Clinical and Laboratory Standards Institute, M07-A8, "Methods for dilution antimicrobial susceptibility tests for bacteria that grow aerobically," approved standard: eighth edition, Wayne, PA: CLSI (2009).
Clinical and Laboratory Standards Institute, M100-S20-U, "Performance standards for antimicrobial susceptibility testing," 20th informational supplement, Wayne, PA: CLSI (2010).
Gales, A.C. et al., "Global assessment of the antimicrobial activity of polymyxin B against 54 731 clinical isolates of Gram-negative bacilli,": report from the SENTRY antimicrobial surveillance programme (2001-2004), Clin Microbiol Infect 12:315-321 (2006).
Giamarellou, H. et al. "Multidrug-resistant Gram-negative infections: What are the treatment options?," Drugs 69: 1879-1901 (2009).
Li, J. et al., "Colistin: The re-emerging antibiotic for multidrug resistant Gram-negative bacterial infections," Lancet Infect Dis 6:589-601 (2006).
Livermore, D.M., "Has the era of untreatable infections arrived?," J Antimcrob Chemother 64 Suppl 1:i29-i36 (2009).
Michalopoulos, A. et al.,"Colistin and polymyxin B in critical care," Crit Care Clin 24: 377-391 (2008).
Sader, H.S. et al., "Assessment of colistin and polymyxin B antimicrobial susceptibility testing methods against non-fermentative Gram-negative bacilli (NFGNB)," Abstr. C173, 106TH ASM, Orlando FL (2006).
Tygacil Package Insert, available at www.wyeth.com, accessed Aug. 2009 (2009).
Zavascki, A.P. et al., "Polymyxin B for the treatment of multidrug-resistant pathogens: A critical review," J Antimicrob Chemother 60:1206-1215 (2007).
Extended European Search Report for EP application No. 10184953.7, dated Apr. 6, 2011, pp. 9.
PCT International Preliminary Report on Patentability for International Application No. PCT/US2005/023343, dated Jan. 9, 2007, pp. 12.
PCT International Search Report for International Patent Application No. PCT/US2009/069247, mailed May 6, 2010, pp. 3.
PCT Written Opinion of the International Searching Authority for International Patent Application No. PCT/US2005/023343, dated Dec. 6, 2006, pp. 11.
Ohki, K. et al., "Synthesis and Antimicrobial Activity of Polymyxin B Component, Peptides," Peptide Science 2001, The Japanese Peptide Society (2002), pp. 189-192.
Non Final Office Action for U.S. Appl. No. 12/644,943 dated Feb. 21, 2012.
Notice of Allowance for U.S. Appl. No. 12/644,943 dated Aug. 31, 2012.
Arnold, T.M., et al., "Polymyxin Antibiotics for Gram-Negativbe Infections," Am. J. Health Syst. Pharm., 64(8): 819-826 (Apr. 2007).
Ferrari, D., et al., "The Antibiotic Polymyxin B Modulates $P2X_7$ Receptor Function[1]" J. Immunol, 173: 4652-4660 (2004).
Grzybowska, W., et al., "Interaction of Neomycin with Other Antibiotics on Selected Bacterial Strains," Med. Dosw. Mikrobiol., 56(2): 187-198 (2004).
Guelfi, K.C., et al., "In Vitro Evaluation of the Antimicrobial Activity of Meropenem in Combination with Polymyxin B and Gatifloxacin Against Pseudomonas Aeruginosa and Acinetobacter Baumannii," J. Chemother., 20(2) 180-185 (Apr. 2008).
Kubo, A., et al., "Indole and (E)-2-Hexenal, Phytochemical Potentiators of Polymyxins Against Pseudomonas and *Escherichia Coli*," Antimicrob. Agents and Chemother., 40(6): 1438-1441 (Jun. 1996).
Longbottom, C.L, et al., "Tolerance of Pseudomonas Aeruginosa to Melaleuca Alternifolia (tea tree) Oil is Associated with the Outer Membrane and Energy-Dependent Cellular Processes," Jour. Antimicrob. Chemother., 54: 386-392 (Jul. 2004).
Medoff, G., et al., "Potentiation of Rifampicin, Rifampicin Analogs, and Tetracycline Against Animal Cells by Amphotericin B and Polymyxin B," Cancer Res., 33: 1146-1149 (Jun. 1973).
Michael, R., et al., "Investigation of Synergism Between Combination of Ciproflaxacin, Polymyxin, Sulphadiazine and P-Aminobenzoic Acid," J. Pharm. Pharmacol., 45(3): 171-175 (1993).
Moneib, N. A., "In-Vitro Activity of Commonly Used Antifungal Agents in the Presence of Rifampin, Polymxyin B and Norfloacin Against Candida Albicans," J. Chemother., 7(6): 525-529 (Dec. 1995).
Munoz, J.L., et al., "Activity of Trimethoprim/Sulfamethoazole Plus Polymyxin B Against Multiresistant Stenotrophomonas maltophilia," Eur. J. Clin. Microbiol. Infect. Dis., 15: 879-882 (1996).
Notice of Allowance for U.S. Appl. No. 13/167,495 "Antibiotic Compositions for the Treatment of Gram Negative Infections" dated Dec. 10, 2012.
Ogita, A., et al., "Synergistic Fungicidal Activities of Polymxyin B and Ionophores, and Their Dependence on Direct Disruptive Action of Polymyxin B on Fungal Vacuole," J. Antibiot. (Tokyo), 62(2): 81-87 (Feb. 2009).
Pankey, G.A., et al., "The Detection of Synergy Between Meropenem and Polymyxin B Against Meropenem-Resistant Acinetobacter baumannii Using ETest® and Time-Kill Assay," Diagn. Micr. Infec. Dis., 63(2): 228-232 (Feb. 2009).
Pankey, G.A., et al., "Detection of Synergy Using the Combination of Polymyxin B With Either Meropenem or Rifampin Against Carbapenemase-Producing Klebsiella Pneumoniae," Diagn. Microbiol. Infect. Dis., 70(4): 561-564 (Aug. 2011).
Pietschmann, S., et al., "Synergistic Effects of Miconazole and Polymyxin B on Microbial Pathogens," Vet. Res. Commun., 33(6): 489-505 (Aug. 2009).
Rosenblatt, J.E., et al., "Combined Activity of Sulfamethoxazole, Trimethoprim, and Polymyxin B Against Gram-Negative Bacilli," Antimicrob. Ag. and Chemother., 84-92 (Jul. 1974).
Schwartz, S.N., et al., "Antifungal Properties of Polymyxin B and Its Potentiation of Tetracycline as an Antifungal Agent," Antimicrob. Ag. and Chemother., 2(1): 36-40 (Jul. 1972).

(56) References Cited

OTHER PUBLICATIONS

Tempera, G., et al., "In Vitro Evaluation of the Synergistic Activity of Neomycin-Polymyxin B Association Against Pathogens Responsible for Otitis Externa," Int. J. Immunopathol. Pharmacol., 22(2): 299-302 (Apr. 2009) [abstract only].

Urban, C., et al., "Considerations in Control and Treatment of Nosocomial Infections Due to Multidrug-Resistant Acinetobacter baumannii," Clinical Practice, 36: 1268-1274 (May 2003).

Wareham, D.W., et al., "In Vitro Activities of Polymyxin B, Imipenem, and Rifampin Against Multidrug-Resistant Acinetobacter baumannii," Antimicrob. Agents Chemother., 50(2): 825-826 (Feb. 2006).

Wareham, D.W., et al., "In Vitro Activity of Polymyxin B in Combination with Imipenem, Rifapicin and Azithromycin Versus Multidrug Resistant Strains of Acinetobacter baumannii Producing OXA-23 Carbapenemases," Annals of Clin. Microbiol. and Antimicrobials, 5:10 (2006).

Yoon, J., et al., "In Vitro Double and Triple Synergistic Activities of Polymyxin B, Impenem, and Rifampin Against Multidrug-Resistant Acinetobacter baumannii," Antimicrob. Agents Chemother., 48(3): 753-757 (Mar. 2004).

Brownlee, G., et al., "Comparative Biological Studies of Polymyxin A and Polymyxin D," *Annals New York Academy of Sciences*, 51(5): 891-896 (Jun. 1949).

Brownlee, G., et al., "The Pharmacology of Polymyxin A, B, and D," *Annals New York Academy of Sciences*, 51(5): 952-967 (Jun. 1949).

Brownlee, G., et al., "Remarks on Clinical Results with Polymyxin A and B," *Annals New York Academy of Sciences*, 51(5): 998-1000 (Jun. 1949).

Bryer, M., et al., "Pharmacology of Polymyxin," *Annals New York Academy of Sciences*, 51(5): 935-943 (Jun. 1949).

Catch, J.R., et al., "The Chemistry of Polymyxin A," *The Wellcome Chemical Research Laboratories*, 51(5): 917-923 (Jun. 1949).

Bruch, M., et al., "Higher-Order Structure of Polymyxin B: The Functional Significance of Topological Flexibility," J. Am. Chem. Soc. 121: 11993-12001 (1999).

International Preliminary Report on Patentability for International Application No. PCT/US2009/069247 dated Jul. 7, 2011.

Kimura, et al. "Polymyxin P, New Antibiotics of Polymyxin Group," J. Antibiot., XXII(9): 449-450 (Sep. 1969).

Mares, J., et al., "Interactions of Lipopolysaccharide and Polymyxin Studied by NMR Spectroscopy," J. Biol. Chem., 284(17): 11498-11506 (Apr. 24, 2009).

Matsenaga, H., et al., "Polymyxin P, Antibiotics from *Bacillus polymyxa* T-39; Fermentation, Isolation, Structure Elucidation and Antibacterial Activity," *Mukogawa Women's University* Nishimoyia 663, 37: 37-43 (1995).

Parker, et al. "EM49: A New Peptide Antibiotic II. Chemical Characterization," J. Antibiot., 26(8):449-456 (1975).

Pristovsek, P, et al., "Solution Structure of Polymyxins B and E and Effect of Binding to Lipopolysaccharide: An NMR and Molecular Modeling Study," J. Med. Chem.42: 4604-4613 (1999).

Shoji, J. et al. "The Structure of Polymyxin T (Studies on Antibiotics from the Genus Bacillus. XXII)," J. Antibiot.30(12):1042-1048 (1977).

Short, E., "Mechanism of Methionine Protection Against the Nephrotoxicity of Polymyxin A," Brit. J. Pharmacol., 7 248-254 (1952).

Trakhanova, M.N., et al., "Structural and Functional Investigation of Polymyxins, Structure and Biological Properties of Polymyxin M Analogs," *All Union Research Institute of Antibiotics, Moscow*, 1: 20-24 (1989).

Trakhanova, M.N., et al., "Structural and Functional Investigation of Polymyxins, Isolation and Properties of Individual Polymyxin M Components," *All Union Research Institute of Antibiotics, Moscow*, 4: 262-266 (1988).

Velkov, T. et al., "Structure-Activity Relationships of Polymyxin Antibiotics," J. Med. Chem, 53(5): 1898-1916 (2010).

Wang, W., et al., "Structure and Dynamics of $^{13}C,^{15}N$-Labeled Lipopolysaccharides in a Membrane Mimetic," *Angew. Chem. Int. Ed.*, 47: 9870-9874 (2008).

Wilkinson, S., et al., "Structures of the Polymyxins A and the Question of Identity with the Polymyxins M," *Nature*, No. 5059 p. 311 (Oct. 15, 1966).

Written Opinion of the International Searching Authority for International Application No. PCT/US2009/069247 dated Jun. 23, 2011.

\* cited by examiner

US 8,889,826 B2

PEPTIDE ANTIBIOTICS AND METHODS FOR MAKING SAME

RELATED APPLICATION

This application is the U.S. National Stage of International Application No. PCT/US2005/023343, filed on Jul. 1, 2005, published in English, which claims the benefit of U.S. Provisional Application No. 60/813,587, filed on Jul. 1, 2004. The entire teachings of the above applications are incorporated herein by reference.

FIELD OF THE INVENTION

Disclosed herein are novel peptides and novel protected peptides derived from polymyxin and octapeptin peptides, including, e.g., colistin, circulin A, polymyxin A, polymyxin B, polymyxin D, octapeptin B, octapeptin C, and [Ile$^7$]polymyxin B$_1$. The novel peptides and novel protected peptides have antibacterial properties. Also disclosed are pharmaceutical compositions containing the novel peptides and novel protected peptides, as well as methods for preparing the novel peptides and novel protected peptides.

BACKGROUND

Gram-negative bacteria that are resistant to aminoglycoside, β-lactam, and fluoroquinolone antibiotics are increasingly common. These bacteria are often susceptible to the polymyxins and related peptides having antibacterial properties (Refs. 1, 10, 23). As a result, there is interest in the use of polymyxins for multidrug-resistant gram-negative bacterial infections in humans (Ref. 23).

Peptides such as polymyxin B and the related colistin (polymyxin E) have been administered to humans as antibacterial agents. However, their use has been previously restricted because of their toxicity. These peptides comprise a seven amino acid cyclic peptide attached to an exocyclic three amino acid chain, wherein the N-terminal amine of the exocyclic chain is linked to a "side chain" or "tail". The tail is most commonly an acyl group.

Some renal toxicity has been observed with the recommended dosing of polymyxin B in patients. Neurotoxicity has also been observed in patients with compromised renal functions, with an overall incidence of 7.3% reported in one large study with colistin (Ref. 1). The acyl exocyclic chain and the adjacent N-terminal 2,4-diaminobutanoic acid (Dab) residue can be enzymatically removed from polymyxin, thereby yielding the corresponding nonapeptide. The in vivo toxicity of the nonapeptide of polymyxin B is significantly less than that of polymyxin B itself (Ref. 16). The toxicity of the nonapeptide in cell culture is reduced by about 100-fold relative to polymyxin B; however, the antibacterial activity of the nonapeptide is also reduced by about 2-64 fold relative to polymyxin B (Ref. 11).

Attempts have been made to chemically modify polymyxin and colistin in order to obtain peptides with improved antibacterial properties. For example, the total synthesis of polymyxin B and four analogs was previously accomplished by a combination of solid phase peptide syntheses to obtain linear structures, followed by removal from the resin and condensation in solution at high dilution to obtain the cyclic peptide structure (Ref. 7). The derivatives, however, were less active than polymyxin B. A more recent total synthesis of polymyxin B and a few closely related compounds was accomplished only by solid phase peptide synthesis (Refs. 15, 26). Although both of these solid phase total synthetic approaches can provide new derivatives of polymyxin, these methods appear limited since the quantities of antibiotic produced are small and require large amounts of amino acid precursors. Any scale up of these methods for clinical studies may prove to be difficult and costly.

Accordingly, there remains an ongoing need for new peptide compounds having antibacterial properties, and new methods for preparing such compounds.

SUMMARY

Disclosed herein are novel peptides, such as peptide antibiotics and/or other peptides having antibacterial properties, and methods for preparing the peptides. The compounds disclosed herein can provide structural diversity in the exocyclic region (the exocyclic amino acids and tail) of the cyclic peptide.

DEFINITIONS

"Acyl," as used herein, refers to a carbonyl radical attached to an alkyl, alkenyl, alkynyl, cycloalkyl, heterocyclyl, aryl, or heteroaryl group. Exemplary acyls include, but are not limited to: (1) "unsubstituted alkanoyl," which is defined as carbonyl radical attached to an unsubstituted alkyl group; (2) "unsubstituted alkenoyl," which is defined as carbonyl radical attached to an unsubstituted alkenyl group; (3) "substituted alkanoyl," which is defined as a carbonyl radical attached to a substituted alkyl group, in which one or more hydrogen atoms is replaced by a substituent group selected from acyl, acylamino, acyloxy, alkenyl, alkoxy, alkyl, alkynyl, amino, aryl, aryloxy, carbamoyl, carboalkoxy, carboxy, carboxyamido, carboxyamino, cyano, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, and ureido; and (4) "substituted alkenoyl," which is defined as carbonyl radical attached to an substituted alkenyl group, in which one or more hydrogen atoms is replaced by a substituent group as described above. Nonlimiting examples of acyls include radicals such as acetyl, n-octanoyl, n-nonanoyl, benzoyl, and isonicotinoyl.

"Acylamino," as used herein, refers to an amino group bonded to an acyl group.

"Acyloxy," as used herein, refers to an oxygen radical substituted with an acyl group. In some embodiments, acyloxy is substituted with an acyl, acylamino, acyloxy, alkenyl, alkoxy, alkyl, alkynyl, amino, aryl, aryloxy, carbamoyl, carboalkoxy, carboxy, carboxyamido, carboxyamino, cyano, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, or ureido group.

An "addition reagent," as used herein, is a compound that can react with an amino group such as the N-terminus of a peptide, thereby chemically modifying the amino group by addition of all, or a component, of the addition reagent to the amino group. For example, an addition reagent may be an acylamino reagent such as R'—(C=O)-LG or a sulfonating reagent such as R'—SO$_2$-LG, where LG is a leaving group, that can react with an amino group to form an acylamino group or a sulfonamino group, respectively. An addition reagent may also be, for example, an isocyanate, isothiocyanate, activated ester, acid chloride, sulfonyl chloride, activated sulfonamide, activated heterocycle, activated heteroaryl, chloroformate, cyanoformate, thioacylester, phosphoryl chloride, phosphoramidate, imidate, or lactone. An addition reagent may also be an aldehyde or ketone that reacts with an amine under reductive conditions to form an alkylated amine. An addition reagent may also be an activated amino acid, or an amino acid and a peptide coupling reagent, such as, e.g., PYBOP® (benzotriazole-1-yl-oxy-tris-pyrrolidino-phosphonium hexafluorophosphate), HBtU (2-(1H-benzotriazole-1-yl)-1,1,3,3-tetramethyluronium hexafluorophosphate), HBtU/HOBt (2-(1H-benzotriazole-1-yl)-1,1,3,3-tetramethyluronium hexafluorophosphate/N-hydroxybenzotriazole), or DCC (dicyclohexylcarbodiimide).

"Alkenyl," as used herein, refers to linear or branched radicals having 2-20 carbon atoms, such as 2-12, 2-10, or 2-6 carbon atoms, and containing at least one carbon-carbon double bond. One or more hydrogen atoms can also be replaced by a substituent group selected from acyl, acylamino, acyloxy, alkenyl, alkoxy, alkyl, alkynyl, amino, aryl, aryloxy, carbamoyl, carboalkoxy, carboxy, carboxyamido, carboxyamino, cyano, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, and ureido. The double bond portion(s) of the unsaturated hydrocarbon chain may be either in the cis or trans configuration. Nonlimiting examples of alkenyls include "unsubstituted alkenyl," which is defined as an alkenyl group that bears no substituent groups. Other nonlimiting examples of alkenyl groups include ethenyl, 2-phenyl-1-ethenyl, prop-1-en-2-yl, prop-2-en-1-yl (allyl), prop-1-en-1-yl, cycloprop-1-en-1-yl; cycloprop-2-en-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl.

"Alkoxy," as used herein, refers to an oxygen radical substituted with an alkyl, alkenyl, alkynyl, cycloalkyl, or heterocyclyl group. Nonlimiting examples include methoxy, tert-butoxy, benzyloxy, and cyclohexyloxy.

"Alkyl," as used herein, refers to a linear or branched saturated radicals having at least one carbon atom, such as 1-20 carbon atoms, 1-12, 1-10, or 1-6 carbon atoms, or at least 6 carbon atoms, at least 7 carbon atoms, at least 8 carbon atoms, at least 9 carbons atoms, or at least 10 carbon atoms, unless otherwise specified. A "lower alkyl" is defined as an alkyl group containing 1-4 carbon atoms. One or more hydrogen atoms can also be replaced by a substituent group selected from acyl, acylamino, acyloxy, alkenyl, alkoxy, alkyl, alkynyl, amino, aryl, aryloxy, carbamoyl, carboalkoxy, carboxy, carboxyamido, carboxyamino, cyano, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, and ureido. Nonlimiting examples of alkyl groups include methyl, butyl, tert-butyl, isopropyl, trifluoromethyl, nonyl, undecyl, octyl, dodecyl, methoxymethyl, 2-(2'-aminophenacyl), 3-indolylmethyl, benzyl, and carboxymethyl. Other exemplary alkyls include, but are not limited to: (1) "unsubstituted alkyl," which is defined as an alkyl group that bears no substituent groups; and (2) "substituted alkyl," which denotes an alkyl radical in which one or more hydrogen atoms is replaced by a substituent group selected from acyl, acylamino, acyloxy, alkenyl, alkoxy, alkyl, alkynyl, amino, aryl, aryloxy, carbamoyl, carboalkoxy, carboxy, carboxyamido, carboxyamino, cyano, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, and ureido. Exemplary alkyl groups include, but are not limited to, methyl, ethyls such as ethanyl (ethyl), propyls such as propan-1-yl (n-propyl), propan-2-yl (iso-propyl), butyls such as butan-1-yl (n-butyl), butan-2-yl (s-butyl), 2-methyl-propan-1-yl (iso-butyl), 2-methyl-propan-2-yl (tert-butyl), trifluoromethyl, nonyl, undecyl, octyl, dodecyl, methoxymethyl, 2-(2'-aminophenacyl), 3-indolylmethyl, benzyl, and carboxymethyl.

"Alkynyl," as used herein, refers to linear and branched radicals having from 2-10 carbon atoms, and containing at least one carbon-carbon triple bond. One or more hydrogen atoms can also be replaced by a substituent group selected from acyl, acylamino, acyloxy, alkenyl, alkoxy, alkyl, alkynyl, amino, aryl, aryloxy, carbamoyl, carboalkoxy, carboxy, carboxyamido, carboxyamino, cyano, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, and ureido. Examples of alkynyl groups include, but are not limited to, ethynyl, prop-1-yn-1-yl, prop-2-yn-1-yl, but-1-yn-1-yl, but-1-yn-3-yl, and but-3-yn-1-yl.

"Amino," as used herein, refers to an $NR_1R_2$ radical, in which $R_1$ and $R_2$ may be selected from hydrido, acyl, acyloxy, alkenyl, alkoxy, alkyl, alkynyl, aryl, aryloxy, carbamoyl, carboalkoxy, carboxy, formyl, heteroaryl, heterocyclyl, hydroxy, imino, nitro, oxo, sulfinyl, sulfonyl, and thio. A monosubstituted amino refers to an $NR_1R_2$ radical wherein $R_1$ is hydrido and $R_2$ is selected from acyl, acyloxy, alkenyl, alkoxy, alkyl, alkynyl, aryl, aryloxy, carbamoyl, carboalkoxy, carboxy, formyl, heteroaryl, heterocyclyl, hydroxy, imino, nitro, oxo, sulfinyl, sulfonyl, and thio. A disubstituted amino refers to an $NR_1R_2$ radical wherein $R_1$ and $R_2$ are each independently selected from acyl, acyloxy, alkenyl, alkoxy, alkyl, alkynyl, aryl, aryloxy, carbamoyl, carboalkoxy, carboxy, formyl, heteroaryl, heterocyclyl, hydroxy, imino, nitro, oxo, sulfinyl, sulfonyl, and thio.

An "amino acid," as used herein, refers to a compound containing a carboxylic acid group and an amino group and having the formula $H_2N[C(R)(R')]_n$—$C(O)OH$, where n is an integer greater than equal to one, and R and R' are independently selected from hydrogen and amino acid side chains. For example, when n is equal to one, the amino acid of the formula $H_2N[C(R)(R')]C(O)OH$ is an alpha amino acid, and when n is equal to two, the amino acid of the formula $H_2N$—$C(R_1)(R_1')$—$C(R_2)(R_2')$—$C(O)OH$ is a beta amino acid, where $R_1$, $R_1'$, $R_2$, and $R_2'$ are each independently chosen from amino acid side chains. An "amino acid residue," as used herein, refers to an amino acid that is part of a peptide or protein, and having the formula —$N(H)C(R)(R')C(O)$—. An "amino acid side chain" as used herein, refers to any side chain from a naturally-occurring or synthetic amino acid. For example, methyl may be referred to as an alanine side chain, and 2-amino-1-ethyl may be referred to as the side chain of 2,4-diaminobutanoic acid.

Exemplary amino acids may be chosen from the twenty encoded amino acids and derivatives thereof, as well as from, e.g., other α-amino acids, β-amino acids, γ-amino acids, δ-amino acids, and ω-amino acids. An amino acid may have R or S chirality at any chiral atom. An amino acid may be chosen from, e.g., alanine, β-alanine, α-aminoadipic acid, 2-aminobutanoic acid, 4-aminobutanoic acid, 1-aminocyclopentanecarboxylic acid, 6-aminohexanoic acid, 2-aminoheptanedioic acid, 7-aminoheptanoic acid, 2-aminoisobutyric acid, aminomethylpyrrole carboxylic acid, 8-amino-3,6-dioxa-octanoic acid, aminopiperidinecarboxylic acid, 3-amino-propionic acid, aminoserine, aminotetrahydropyran-4-carboxylic acid, arginine, asparagine, aspartic acid, azetidine carboxylic acid, benzothiazolylalanine, butylglycine, carnitine, 4-chlorophenylalanine, citrulline, cyclohexylalanine, cyclohexylstatine, cysteine, 2,4-diaminobutanoic acid, 2,3-diaminopropionic acid, dihydroxyphenylalanine, dimethylthiazolidine carboxylic acid, glutamic acid, glutamine, glycine, histidine, homoserine, hydroxyproline, isoleucine, isonipecotic acid, leucine, lysine, methanoproline, methionine, norleucine, norvaline, ornithine, p-aminobenzoic acid, penicillamine, phenylalanine, phenylglycine, piperidinylalanine, piperidinylglycine, proline, pyrrolidinylalanine, sarcosine, selenocysteine, serine, statine, tetrahydropyranglycine, thienylalanine, threonine, tryptophan, tyrosine, valine, allo-isoleucine, allo-threonine, 2,6-diamino-4-hexanoic acid, 2,6-diaminopimelic acid, 2,3-diaminopropionic acid, dicarboxidine, homoarginine, homocitrulline, homocysteine, homocystine, homophenylalanine, homoproline, and 4-hydrazinobenzoic acid.

N-protected α-amino acids for peptide synthesis having L- or D-chirality at Cα are commercially available, e.g., from NOVABIOCHEM® (San Diego, Calif.) and Bachem (Bubendorf, Switzerland). The synthesis of chiral α-amino acids and other amino acids is also well known to those of ordinary skill in the art, and is described, e.g., in Arnstein Synthesis of amino acids and proteins, University Park Press, 1975; Enantioselective Synthesis of Beta-Amino Acids, Juaristi et al., Eds., Wiley-VCH: New York, 2005; and Williams Synthesis of optically active α-amino acids, Pergamon Press, 1989.

"Amino protecting group," as used herein, refers to any substituent that may be used to prevent an amino group on a molecule from undergoing a chemical reaction while chemical change occurs elsewhere in the molecule. An amino protecting group can be removed under the appropriate chemical conditions. Numerous amino protecting groups are known to those skilled in the art, and examples of amino protecting groups, methods for their addition, and methods for their removal can be found in "Protective Groups in Organic Synthesis" by Theodora W. Greene,
John Wiley and Sons, New York, 1991, the disclosure of which is incorporated herein by reference. Nonlimiting examples of amino protecting groups include phthalimido, trichloroacetyl, STA-base, benzyloxycarbonyl, t-butoxycarbonyl, t-amyloxycarbonyl, isobornyloxycarbonyl, adamantyloxycarbonyl, chlorobenzyloxycarbonyl, and nitrobenzyloxycarbonyl. Other exemplary amino protecting groups include "carbamate amino protecting groups," which are defined as a carbonyl containing protecting group that when bound to an amino group forms a carbamate. Nonlimiting exemplary amino carbamate protecting groups include 9-fluorenylmethoxycarbonyl (Fmoc), allyloxycarbonyl (Alloc), carbobenzyloxy (CBZ), and t-butoxycarbonyl (Boc) protecting groups. Other exemplary protecting groups include 9-fluorenylmethoxycarbonyl (Fmoc) substituted with acidic substituents, such as 2-sulfo-9-fluorenylmethoxycarbonylcarbonyl, 2-carboxymethyl-9-fluorenylmethoxycarbonyl, and 4-carboxy-9-fluorenylmethoxycarbonyl.

"Amino protecting group reagents," as used herein, refer to addition reagents that can react with an amino group such as the N-terminus of a peptide, thereby chemically modifying said amino group by addition of an amino protecting group.

"Aryl," as used herein, refers to a mono-, bi-, or other multi-carbocyclic, aromatic ring system. The aryl group can optionally be fused to one or more rings selected from aryls, cycloalkyls, and heterocyclyls. Aryls can have from 5-14 ring members, such as from six to ten ring members. One or more hydrogen atoms may also be replaced by a substituent group selected from acyl, acylamino, acyloxy, alkenyl, alkoxy, alkyl, alkynyl, amino, aryl, aryloxy, azido, carbamoyl, carboalkoxy, carboxy, carboxyamido, carboxyamino, cyano, cycloalkyl, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, and ureido. Nonlimiting examples of aryl groups include phenyl, naphthyl, biphenyl, and anthracenyl.

"Aryloxy," as used herein, refers to an oxygen radical substituted with an aryl or heteroaryl group. An exemplary aryloxy includes, but is not limited to, phenoxy.

"Carbamoyl," as used herein, refers to a nitrogen radical of the formula —N(R$^{x2}$)—C(O)—OR$^{x3}$, wherein R$^{x2}$ is selected from hydrido, alkyl, alkenyl, alkynyl, cycloalkyl, heterocyclyl, aryl, and heteroaryl, and R$^{x3}$ is selected from alkyl, aryl, cycloalkyl, heteroaryl, and heterocyclyl.

"Carboalkoxy," as used herein, refers to a carbonyl radical bonded to an alkoxy or aryloxy group.

"Carboxy," as used herein, refers to a COOH radical.

"Carboxyamino," as used herein, refers to a CONH$_2$ radical.

"Carboxyamido," as used herein, refers to a carbonyl radical bonded to a monosubstituted amino or disubstituted amino group.

"Cycloalkyl," as used herein, refers to a saturated or partially unsaturated carbocyclic ring in a single or fused carbocyclic ring system having from three to twelve ring members, such as a ring system having from three to seven ring members. One or more hydrogen atoms may also be replaced by a substituent group selected from acyl, acylamino, acyloxy, alkenyl, alkoxy, alkyl, alkynyl, amino, aryl, aryloxy, carbamoyl, carboalkoxy, carboxy, carboxyamido, carboxyamino, cyano, cycloalkyl, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, and ureido. Nonlimiting exemplary cycloalkyl groups include cyclopropyl, cyclobutyl, cyclohexyl, and cycloheptyl.

"Fmoc" is a 9-fluorenylmethoxycarbonyl group.

"Halo," as used herein, refers to a bromo, chloro, fluoro or iodo radical.

"Heteroaryl," as used herein, refers to an aromatic radical having from one to four hetero atoms or hetero groups selected from O, N, NH, S, or SO in a single or fused heterocyclic ring system, having from five to fifteen ring members, such as a heteroaryl ring system having from six to ten ring members. One or more hydrogen atoms may also be replaced by a substituent group selected from acyl, acylamino, acyloxy, alkenyl, alkoxy, alkyl, alkynyl, amino, aryl, aryloxy, carbamoyl, carboalkoxy, carboxy, carboxyamido, carboxyamino, cyano, cycloalkyl, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, and ureido. Nonlimiting examples of heteroaryl groups include indolyl, pyridinyl, thiazolyl, thiadiazoyl, isoquinolinyl, pyrazolyl, oxazolyl, oxadiazolyl, triazolyl, and pyrrolyl groups.

"Heterocyclyl" or "heterocyclic," as used herein, refers to a saturated or partially unsaturated ring containing one to four hetero atoms or hetero groups selected from O, N, NH, N(alkyl, such as lower alkyl), S, SO or SO$_2$, in a single or fused heterocyclic ring system having from three to twelve ring members, such as a heterocyclyl ring system having from three to seven ring members. One or more hydrogen atoms may also be replaced by a substituent group selected from acyl, acylamino, acyloxy, alkenyl, alkoxy, alkyl, alkynyl, amino, aryl, aryloxy, carbamoyl, carboalkoxy, carboxy, carboxyamido, carboxyamino, cyano, cycloalkyl, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, and ureido. Nonlimiting examples of heterocyclyl groups include morpholinyl, piperidinyl, pyrrolidinyl and succinimidyl.

"Hydroxy," as used herein, refers to —OH.

"Iminoamino," as used herein, refers to —N(H)C(=NR$^{x26}$)R$^{x27}$, wherein R$^{x26}$ and R$^{x27}$ are selected from hydrido, alkyl, aryl, cycloalkyl, heteroaryl, and heterocyclyl.

"Phosphonamino," as used herein, refers to

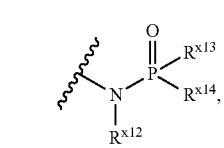

wherein R$^{x13}$ and R$^{x14}$ are independently selected from alkoxy, alkyl, amino, aryl, aryloxy, cycloalkyl, disubstituted amino, halo, heteroaryl, heterocyclyl, hydroxy, monosubstituted amino, and thio.

"Sulfinyl," as used herein, refers to —S(=O)OH.

"Sulfo," as used herein, refers to —SO$_3$H.

"Sulfonamino," as used herein, refers to an amino radical of the formula

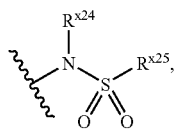

wherein each of $R^{x24}$ is selected from hydrido, alkyl, cycloalkyl, aryl, heteroaryl, and heterocyclyl, and $R^{x25}$ is selected from alkyl, aryl, cycloalkyl, heteroaryl, and heterocyclyl.

"Sulfonyl," as used herein, refers to a hexavalent sulfur radical substituted with two oxo substituents and a third substituent selected from alkyl, cycloalkyl, heterocyclyl, aryl, and heteroaryl.

"Thio," as used herein, refers to a radical containing a substituent group independently selected from hydrido, alkyl, cycloalkyl, heterocyclyl, aryl and heteroaryl, attached to a divalent sulfur atom, such as methylthio and phenylthio.

"Thioacyl," as used herein, refers to a thiocarbonyl radical attached to an alkyl, alkenyl, alkynyl, cycloalkyl, heterocycyl, aryl or heteroaryl group.

"Thioacylamino," as used herein, refers to an amino radical bonded to a thioacyl group.

"Thioacylester," as used herein, refers to a thiocarbonyl radical attached to an alkoxy group.

"Thioureido," as used herein, refers to a nitrogen radical of the formula —N($R^{x5}$)—C(S)—N($R^{x6}$)($R^{x7}$), wherein each of $R^{x5}$ and $R^{x6}$ is independently selected from hydrido, alkyl, alkenyl, alkynyl, cycloalkyl, heterocyclyl, aryl, and heteroaryl; and $R^{x7}$ is selected from an alkyl, aryl, cycloalkyl, heteroaryl, and heterocyclyl.

"Ureido," as used herein, refers to a nitrogen radical of the formula —N($R^{x21}$)—C(O)—N$R^{x22}R^{x23}$, wherein each of $R^{x21}$ and $R^{x22}$ is independently selected from hydrido, alkyl, alkenyl, alkynyl, cycloalkyl, heterocyclyl, aryl, and heteroaryl; and $R^{x23}$ is selected from an alkyl, aryl, cycloalkyl, heteroaryl, and heterocyclyl.

The compounds of the present invention may be used in the form of salts or pharmaceutically-acceptable salts derived from inorganic or organic acids. The present invention includes all such salts and all crystalline forms of such salts. By "pharmaceutically-acceptable salt" is meant those salts that are, within the scope of sound medical judgment, suitable for use in contact with the tissues of humans and lower animals without undue toxicity, irritation, and allergic response, and are commensurate with a reasonable benefit/risk ratio. Pharmaceutically-acceptable salts are well known in the art. For example, S. M. Berge, et al. describes pharmaceutically-acceptable salts in *J. Pharm. Sci.*, 1977, 66:1-19. All of these salts may be prepared by conventional means from the corresponding compound of the invention by treating, for example, the compound with the appropriate acid or base.

The salts or pharmaceutically-acceptable salts may be prepared in situ during the final isolation and purification of the compounds of the invention, or separately by reaction of a free base function with a suitable acid. For example, basic addition salts can be prepared in situ during the final isolation and purification of compounds of this invention by combining a carboxylic acid-containing group with a suitable base such as the hydroxide, carbonate, or bicarbonate of a pharmaceutically-acceptable metal cation, or with ammonia or an organic primary, secondary, or tertiary amine.

Nonlimiting examples of organic acids may be selected from aliphatic, cycloaliphatic, aromatic, aryl, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactic, and galacturonic acid. Representative organic acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate addition salts. Examples of acids that may be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid.

Also, the basic nitrogen-containing groups can be quaternized with such agents as lower alkyl halides (e.g., methyl, ethyl, propyl, and butyl chlorides, bromides and iodides); dialkyl sulfates (e.g., dimethyl, diethyl, dibutyl and diamyl sulfates); long-chain halides (e.g., decyl, lauryl, myristyl and stearyl chlorides, bromides and iodides); or arylalkyl halides (e.g., benzyl and phenethyl chloride bromides and iodides) and others. Water- or oil-soluble or -dispersible products are thereby obtained.

For example, suitable pharmaceutically-acceptable base addition salts of compounds of the invention include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine. Pharmaceutically-acceptable basic addition salts include cations based on alkali metals or alkaline earth metals such as lithium, sodium, potassium, calcium, magnesium, and aluminum salts, and nontoxic quaternary ammonia and amine cations including ammonium, tetramethylammonium, tetraethylammonium, methylammonium, dimethylammonium, trimethylammonium, triethylammonium, diethylammonium, and ethylammonium. Other representative organic amines useful for the formation of base addition salts include ethylenediamine, ethanolamine, diethanolamine, piperidine, and piperazine.

The compounds of the invention can possess one or more asymmetric carbon atoms and are thus capable of exhibiting optical activity. The compounds of the invention can exist in enantiomeric and/or diastereomeric forms, as well as in the form of racemic or non-racemic mixtures thereof. The compounds disclosed herein can be utilized in the present invention as a single isomer or as a mixture of stereochemical isomeric forms.

Diastereomers can be separated by conventional means such as chromatography, distillation, crystallization or sublimation. Enantiomers can be obtained by resolution of the racemic mixtures according to conventional processes, for example by formation of diastereomeric salts by treatment with an optically active acid or base. Nonlimiting examples of appropriate acids include tartaric, diacetyltartaric, dibenzoyltartaric, ditoluoyltartaric and camphorsulfonic acid. The mixture of diastereomers can be separated by crystallization followed by liberation of the optically active bases from the optically active salts. An alternative process for separation of enantiomers includes the use of a chiral chromatography column optimally chosen to maximize the separation of the enantiomers. Another method involves synthesis of covalent diastereomeric molecules by treating compounds of the invention with an activated form of an enantiomerically enriched acid or with an enantiomerically enriched isocyanate. The synthesized diastereomers can be separated by conventional means such as chromatography, distillation, crystallization or sublimation, and then hydrolyzed to obtain the enantiomerically enriched compound. Optically active compounds can likewise be obtained by utilizing optically active starting materials. These isomers may be in the form of a free acid, a free base, an ester or a salt.

Geometric isomers can also exist in the compounds of the present invention. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Substituents around a carbon-carbon double bond alternatively can be referred to as "cis" or "trans," where "cis" represents substituents on the same side of the double bond and "trans" represents substituents on opposite sides of the double bond.

The arrangement of substituents around a carbocyclic ring is also designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans".

An isolated, pure, or purified compound refers to a composition containing at least 10%, such as at least 20%, at least 50%, at least 80%, or at least 90% of the compound. In one embodiment, a pharmaceutically acceptable salt thereof or a pharmaceutical composition comprising any of the compounds disclosed herein exhibits a detectable (e.g., statistically significant) antimicrobial activity when tested in conventional biological assays such as those described herein.

The term "pharmaceutically-acceptable prodrugs" as used herein, represents those prodrugs of the compounds of the present invention that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the invention.

The term "pro-drug," as used herein, represents compounds that are rapidly transformed in vivo to the parent compound of the formulas described herein, for example, by hydrolysis in blood. A discussion is provided in T. Higuchi and V. Stella, *Pro-drugs as Novel Delivery Systems*, Vol. 14 of the ACS Symposium Series, and in Edward B. Roche, ed., *Bioreversible Carriers in Drug Design*, American Pharmaceutical Association and Pergamon Press, 1987, both of which are incorporated herein by reference.

DETAILED DESCRIPTION

Disclosed herein are novel peptides and methods for preparing peptides. The peptides can have applications as antibacterial agents.

One embodiment discloses new peptides comprising a cyclic heptapeptide attached to an exocyclic peptide chain and tail. In one embodiment, the new peptides are derived from naturally occurring peptides having the following structure:

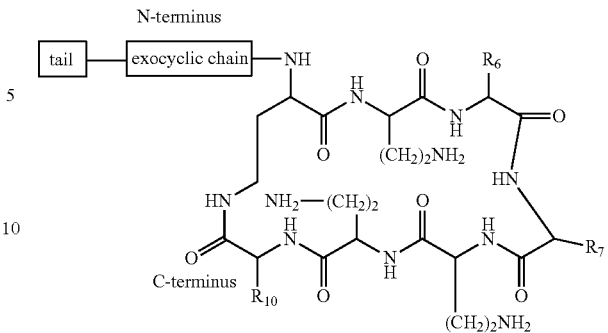

These naturally occurring peptides have an exocyclic peptide chain attached to an N-terminal "side chain" or "tail." In one embodiment, such peptides are related to naturally occurring peptides including polymyxins or octapeptins. These peptides have the common structure shown above with variation at amino acids 6, 7, and 10 (polymyxin numbering), where $R_6$ depicts the side chain of the amino acid at position 6, $R_7$ depicts the side chain of the amino acid at position 7, and $R_{10}$ depicts the side chain of the amino acid at position 10. In one embodiment, $R_6$, $R_7$, and $R_{10}$ may each be independently chosen from iso-propyl (to give Val), benzyl (to give Phe), iso-butyl (to give Leu), sec-butyl (to give Ile), 1-hydroxy-1-ethyl (to give Thr), and hydroxymethyl (to give Ser). In another embodiment, $R_6$ and $R_7$ are each independently chosen from, iso-propyl, benzyl, iso-butyl, sec-butyl, 1-hydroxy-1-ethyl, and hydroxymethyl and $R_{10}$ is chosen from iso-propyl, iso-butyl, sec-butyl, 1-hydroxy-1-ethyl, and hydroxymethyl. The exocyclic chain and tail provide variation as well. In one embodiment, the exocyclic chain comprises 1 to 3 amino acid residues.

In one embodiment, the exocyclic chain comprises a chain of amino acid residues. In another embodiment, the exocyclic chain is represented by —$(Y1)_x(Y2)_y(Y3)_z$—, where Y1, Y2, and Y3 are each independently selected from amino acid residues including non-encoded amino acid residues, and x, y, and z are integers independently selected from 0 and 1.

In one embodiment, the tail is depicted as "T", where the "tail-exocyclic chain" portion has the formula $T(Y1)_x(Y2)_y(Y3)_z$—. In one embodiment, T is selected from R'—(C=O)—, R'—SO$_2$—, R'—(C=NH)—, R'—NH—(C=S)—, R'—NH—(C=O) R'—NH—(C=NH)—, R'—O—(C=O)—, R'—O—(C=S)—, R'—P(O)OH—, R'—(C=S)—, R'-alkyl, and hydrogen wherein R' is selected from alkyl, cycloalkyl, alkenyl, aryl, heteroaryl, and heterocyclyl.

Accordingly, one embodiment provides new peptides derived from naturally occurring peptides, where the naturally occurring peptides have the structure of formula (A):

(A)

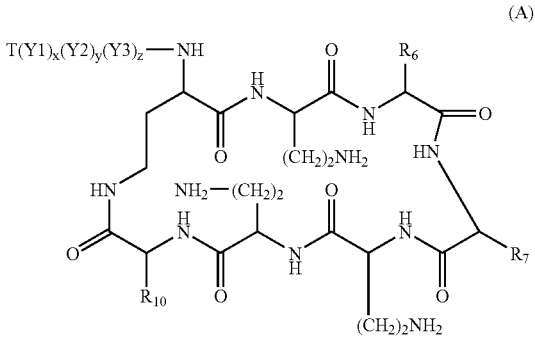

Also disclosed are methods for preparing new peptides containing either free amino groups or protected amino groups. In one embodiment, the new peptides are related to, for example, naturally occurring peptides described herein. In one embodiment, the new peptides have the structure of formula (B):

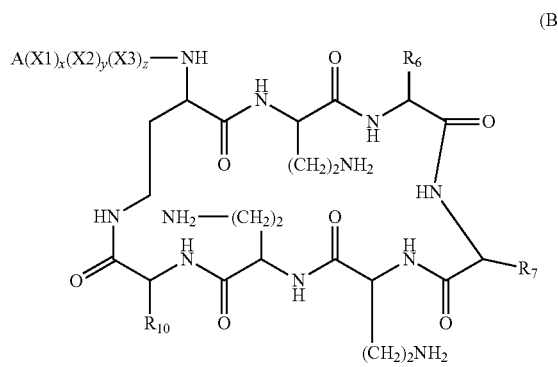

In one embodiment, the exocyclic chain is represented by —$(X1)_x(X2)_y(X3)_z$—, where X1, X2, and X3 are each independently selected from amino acid residues, including any residue described herein, and x, y, and z are integers independently selected from 0 and 1, and "A" represents the tail where A is selected from R'—(C=O)—, R'—$SO_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl, and hydrogen wherein R' is selected from alkyl, cycloalkyl, alkenyl, aryl, heteroaryl, and heterocyclyl.

One embodiment disclosed herein is a method for preparing a compound, comprising:

(a) treating a peptide having at least one side chain comprising an amino group with an amino protecting group reagent to form a protected peptide, wherein the peptide comprises a cyclic heptapeptide attached to an exocyclic peptide chain comprising an acyl group, and the protecting group contains at least one acidic substituent; and (b) treating the protected peptide with a deacylating agent to form a protected, deacylated peptide.

In one embodiment, the peptide to be treated with the protecting group reagent in (a) is selected from naturally occurring peptides having the structure of formula (A), such as polymyxins and octapeptins. Representative polymyxins and octapeptins include polymyxin A (PA), polymyxin B (PB), [Ile$^7$]-polymyxin $B_1$ (IL), polymyxin D, polymyxin E, polymyxin F, polymyxin M (mattacin), polymyxin S, polymyxin T, circulin A, polymyxin D (PD), octapeptin A, octapeptin B (OB), octapeptin C(OC), and octapeptin D. Polymyxin E is conventionally called colistin. Letters (e.g., polymyxin A, polymyxin B, polymyxin C, etc.) generally refer to polymyxins having variations in amino acid sequence. Numerical subscripts (e.g., octapeptin $A_1$, octapeptin $A_2$, octapeptin $A_3$, etc. or polymyxin $B_1$, polymyxin $B_2$, polymyxin $B_3$, etc.) generally refer to variations in the tail. Polymyxins and octapeptins can be isolated from natural sources with a variety of lipid tails, as shown in Table 1 for polymyxin B. One exception is colistin (polymyxin E): colistin A (polymyxin $E_1$) and colistin B (polymyxin $E_2$) differ in lipid tail.

TABLE 1

| Peptide | Tail |
|---|---|
| Polymyxin $B_1$ | 6-methyloctanoyl |
| Polymyxin $B_2$ | 6-methylheptanoyl |
| Polymyxin $B_3$ | octanoyl |
| Polymyxin $B_4$ | heptanoyl |
| Polymyxin $B_5$ | nonanoyl |
| Polymyxin $B_6$ | 3-hydroxy-6-methyloctanoyl |
| Polymyxin E1 (colistin A) | 6-methyloctanoyl |
| Polymyxin E2 (colistin B) | 6-methylheptanoyl |

Table 2 shows the peptide sequences of several peptides disclosed herein.

TABLE 2

| Peptide | Exocyclic chain 1-2-3 | Cyclic Peptide 4-5-6-7-8-9-10 |
|---|---|---|
| Polymyxin A | Dab-Thr-$_D$Dab- | [Dab-Dab-$_D$Leu-Leu-Dab-Dab-Thr-] |
| Polymyxin B (PB) | Dab-Thr-Dab- | [Dab-Dab-$_D$Phe-Leu-Dab-Dab-Thr-] |
| Polymyxin D | Dab-Thr-$_D$Ser- | [Dab-Dab-$_D$Leu-Thr-Dab-Dab-Thr-] |
| Polymyxin M | Dab-Thr-Dab | [Dab-Dab-Leu-Thr-Dab-Dab-Thr-] |
| Polymyxin S | Dab-Thr-Ser | [Dab-Dab-$_D$Phe-Thr-Dab-Dab-Thr-] |
| Polymyxin T | Dab-Thr-Dab | [Dab-Dab-$_D$Phe-Leu-Dab-Dab-Leu-] |
| Colistin (C) | Dab-Thr-Dab- | [Dab-Dab-$_D$Leu-Leu-Dab-Dab-Thr-] |
| Circulin A (CA) | Dab-Thr-Dab- | [Dab-Dab-$_D$Leu-Ile-Dab-Dab-Thr-] |
| Polymyxin A (PA) | Dab-Thr-$_D$Dab- | [Dab-Dab-$_D$Leu-Leu-Dab-Dab-Thr-] |
| Polymyxin D (PD) | Dab-Thr-$_D$Ser- | [Dab-Dab-$_D$Leu-Thr-Dab-Dab-Thr-] |
| Octapeptin A | $_D$Dab- | [Dab-Dab-$_D$Leu-Leu-Dab-Dab-Leu-] |
| Octapeptin B (OB) | $_D$Dab- | [Dab-Dab-$_D$Leu-Leu-Dab-Dab-Leu-] |
| Octapeptin C (OC) | $_D$Dab- | [Dab-Dab-$_D$Leu-Phe-Dab-Dab-Leu-] |
| Octapeptin D | $_D$Ser- | [Dab-Dab-$_D$Leu-Leu-Dab-Dab-Leu-] |
| [Ile$^7$]-polymyxin B | (IL)Dab-Thr-Dab- | [Dab-Dab-$_D$Phe-Ile-Dab-Dab-Thr-] |

*All amino acids are L-isomers unless designated as the D-isomer. Dab is 2, 4-diaminobutanoic acid.

In one embodiment, the peptide to be treated is selected from polymyxin A, polymyxin B (e.g., polymyxin $B_1$, polymyxin $B_2$, and polymyxin $B_3$), [Ile$^7$]-polymyxin $B_1$, polymyxin C, polymyxin D, polymyxin E (also called colistin), polymyxin F, polymyxin M (also called mattacin), polymyxin P, polymyxin S, polymyxin T (e.g., polymyxin $T_1$), colistin (e.g. colistin A and colistin B), circulin A, octapeptin A (e.g., octapeptin $A_1$, octapeptin $A_2$, and octapeptin $A_3$) octapeptin B (e.g., octapeptin $B_1$, octapeptin $B_2$, and octapeptin $B_3$), octapeptin C (e.g., octapeptin $C_1$), and octapeptin D. Polymyxin F is also known, where the amino acid composition is 5:1:1:1:2 Dab:Thr:Ser:Ile:Leu.

In one embodiment, the peptide to be treated is selected from polymyxin B, polymyxin A, polymyxin D, [Ile$^7$]-polymyxin $B_1$, colistin, circulin A, octapeptin B, and octapeptin C.

In one embodiment, the resulting protected deacylated peptide can be further modified to form new protected peptide compounds. New peptide compounds can then be formed following deprotection.

Scheme I below shows one embodiment of a method of protecting and deacylating a peptide. For illustrative purposes, the method is depicted with polymyxin $B_1$. However, this method is applicable to all peptides having the common heptapeptide cyclic core structure of formula (A), such as the polymyxins and octapeptins.

Scheme I

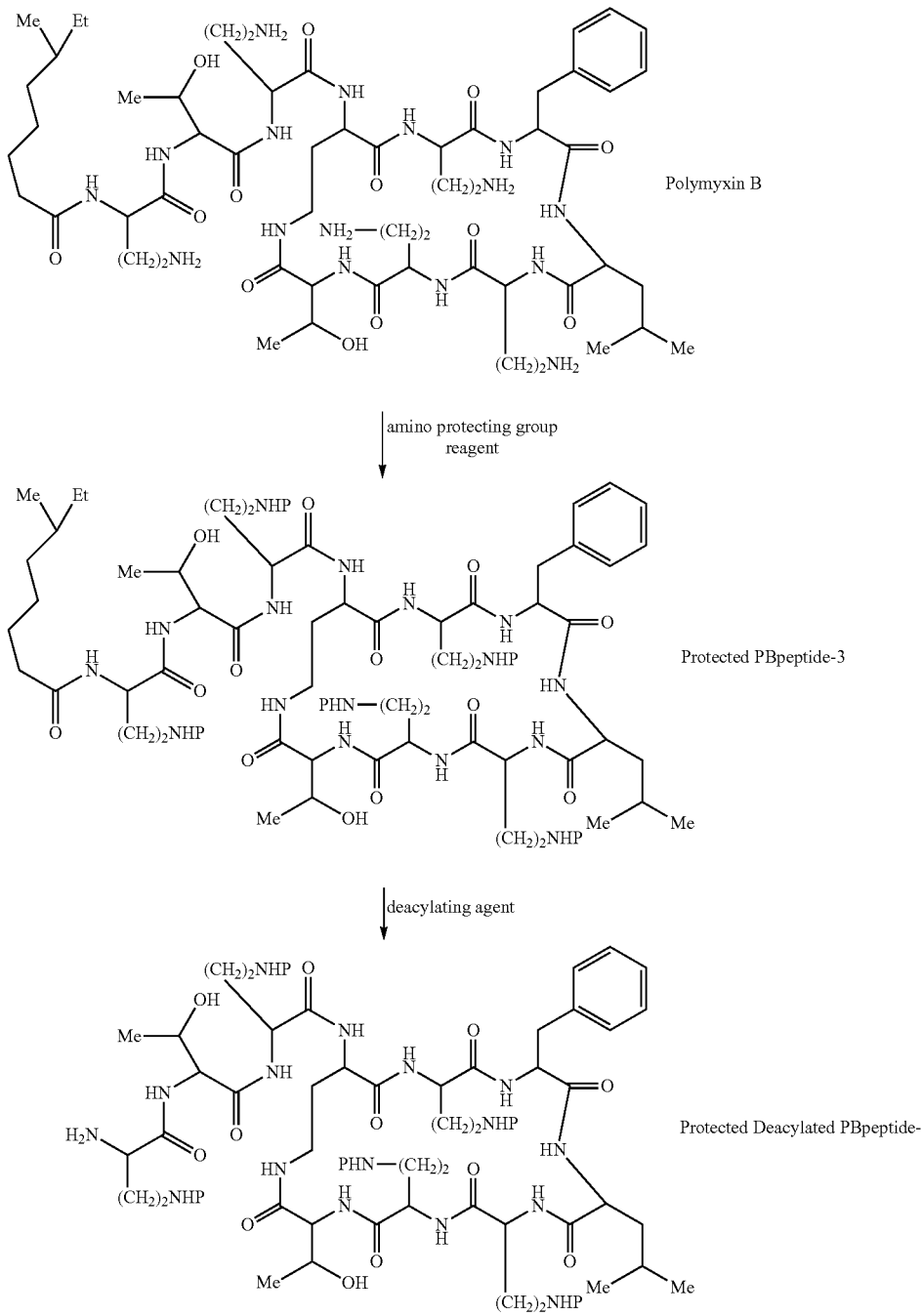

In Scheme I, "P" depicts the protecting group containing at least one acidic substituent. The peptide of Scheme I (polymyxin B, or PB) has three amino acids in the exocyclic chain, and is thus termed "PBpeptide-3."

Although Scheme I depicts protecting all of the amino groups of polymyxin B, the present invention also encompasses protecting one or more amino groups. One of ordinary skill in the art can readily appreciate that the method depicted in Scheme I may equally apply to any peptide disclosed herein.

In one embodiment, the protecting group contains at least one "acidic substituent," which, as used herein, refers to a substituent containing a donatable hydrogen. Exemplary acidic substituents include the acid or salt form of sulfo, sulfate, sulfonate, carboxy, carboxylate, phosphonate, and phosphate. In one embodiment, the protecting group comprises an aryl or heteroaryl substituted with the acidic substituent.

In one embodiment, the protecting group is selected from the acid or salt form of sulfo, sulfate, sulfonate, carboxy, carboxylate, phosphonate, and phosphate derivatives of amino protecting groups, such as carbamate amino protecting groups. Exemplary carbamate amino protecting groups include, but are not limited to, the protecting groups disclosed in "Protective Groups in Organic Synthesis" by Theodora W. Greene, John Wiley and Sons, New York, 1991 at pp. 315-348, the disclosure of which is incorporated herein by reference. Nonlimiting examples of carbamate amino protecting groups include 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (phenoc), 2-phenylethyl carbamate (hZ), 1-methyl-1-(4-biphenylyl)ethyl carbamate (Bpoc), 1-(3,5-di-t-butylphenyl)-1-methylethyl carbamate (t-bumeoc), 2-(2'- and 4'-pyridyl)ethyl carbamate (pyoc), 8-quinolyl carbamate, benzyl carbamate (Cbz- or Z), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-(p-toluenesulfonyl)ethyl carbamate, 4-methylthiophenyl carbamate (Mtpc), 2-triphenylphosphonioisopropyl carbamate (Ppoc), m-chloro-p-acyloxybenzyl carbamate, p-(dihydroxyboryl)benzyl carbamate (Dobz), 5-benzisoxazolylmethyl carbamate (Bic), 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, t-amyl carbamate, p-cyanobenzyl carbamate, p-decyloxybenzyl carbamate, o-(N,N-dimethylcarboxamido)benzyl carbamate, di(2-pyridyl)methyl carbamate, 2-furanylmethyl carbamate, p-(p'-methoxyphenylazo)benzyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Another exemplary protecting group includes 9-fluorenylmethoxycarbonyl (Fmoc) substituted with acidic substituents or salts thereof. Depicted below are examples of protecting groups substituted with acidic substituents for polymyxin peptides and other related peptides, where 2-(sulfo)-9-fluorenylmethoxycarbonyl is abbreviated as HSO$_3$-Fmoc, and its sodium salt is abbreviated as NaSO$_3$-Fmoc:

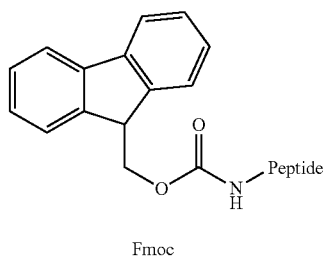

Fmoc

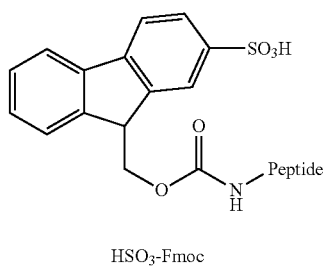

HSO$_3$-Fmoc

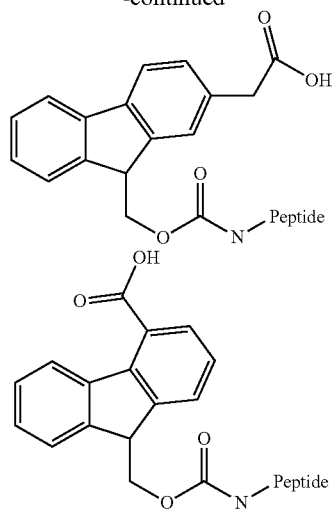

Carboxylic acid derivatives of Fmoc suitable as amino protecting group reagents for the protection of the peptides of the invention can be prepared according to Refs. 8 and 9, the disclosures of which are disclosed herein by reference. Sulfated derivatives of Fmoc can be prepared according to Refs. 28, 29, 32, and 33, the disclosures of which are incorporated herein by reference.

In one embodiment, the protected peptide is water soluble. The water solubility may allow the protected peptide (for example, the protected peptide PBpeptide-3 prior to deacylation in Scheme I), to react with a biologically-based deacylase, e.g., an enzyme, in an aqueous system. In one embodiment, the protected peptide is polyanionic, water soluble as a salt, and can react in aqueous or partially aqueous solution with a deacylase enzyme.

In another embodiment, the protected peptide is water soluble and can undergo an enzyme-mediated transformation other than, or in addition to, deacylation.

In one embodiment, "water soluble" refers to the peptide being substantially completely water soluble. In another embodiment, "water soluble" refers to the peptide being sufficiently water soluble such that any reaction that consumes the peptide in an aqueous system enables the previously insoluble portion of peptide to dissolve in water, and thus, may cause the reaction to be driven to completion. In one embodiment, the protecting group has a sufficient number and/or type of acidic substituents to confer water solubility to the protected peptide.

In one embodiment, the protected peptide is water soluble and can be administered as a prodrug (vide infra).

New peptide compounds can be prepared from polymyxin A, polymyxin B (e.g., polymyxin B$_1$, polymyxin B$_2$, and polymyxin B$_3$), [Ile$^7$]-polymyxin B$_1$, polymyxin C, polymyxin D, polymyxin E (also called colistin), polymyxin F, polymyxin M (also called mattacin), polymyxin P, polymyxin S, polymyxin T (e.g., polymyxin T$_1$), circulin A, octapeptin A (e.g., octapeptin A$_1$, octapeptin A$_2$, and octapeptin A$_3$), octapeptin B (e.g., octapeptin B$_1$, octapeptin B$_2$, and octapeptin B$_3$), octapeptin C (e.g., octapeptin C$_1$), and octapeptin D.

In one embodiment, the peptide is naturally occurring. Peptides having the common heptapeptide cyclic core of structure (A) can be isolated from *Bacillus* spp. (e.g., *Bacillus circulans*, *Bacillus polymyxa*, *Bacillus colistinus*), *Aerohacter aerogenes*, *Paenibacillus kobensis* M, and other bacterial species (Refs. 30-31). For example, polymyxins can be isolated from the fermentation of *Bacillus polymyxa* according to procedures described in Ref. 14.

In another embodiment, the peptide is chemically synthesized. Chemical synthesis of peptides is well known to those of ordinary skill in the art, and is described in, e.g., *Fmoc Solid Phase Peptide Synthesis: A Practical Approach*, Chan et al., Eds., Oxford University Press: New York, 2000; Bodanszky *Principles of Peptide Synthesis*, Springer Verlag: New York, 1993; Lloyd-Williams et al. *Chemical Approaches to the Synthesis of Peptides and Proteins*, CRC Press: Boca Raton, Fla., 1997; and the Novabiochem® (San Diego, Calif.) Catalog.

In one embodiment, the deacylating agent is an enzymatic deacylating agent. One example of an enzyme useful for deacylation of the protected peptide is produced by certain microorganisms of the genus family Actinoplanaceae. Some of the known species and varieties of this family include *Actinoplanes philippinensis, Actinoplanes armeniacus, Actinoplanes utahensis, Actinoplanes missouriensis, Spirillospora albida, Streptosporangium roseum, Streptosporangium vulgare, Streptosporangium roseum var hollandensi, Streptosporangium album, Streptosporangium viridialbum, Amorphosphorangium auranticolor, Ampullariella regularis, Ampullariella campanulata, Ampullariella lobata, Ampullariella digitata, Pilimelia terevasa, Pimelia anulata, Planomonospora parontospora, Planomonospora venezuelensis, Planobispora longispora, Planobispora rosea, Dactylosporangium aurantiacum*, and *Dactylosporangium thailandende*. All natural and artificial variants and mutants which are obtained from the Actinoplanacea family and which produce the enzyme may be used in this invention.

Suitable methods for enzymatic deacylation can be found in U.S. Pat. Nos. 4,524,135, 4,537,717, 4,482,487, RE 32,310, RE 32,311, 5,039,789, and 5,028,590, International Publication Nos. WO03/014147, WO 01/44272, WO 01/44274, and WO 01/44271, the disclosures of which are incorporated herein by reference.

The deacylase enzyme can be obtained as a water-soluble freeze-dried solid. In one embodiment, the deacylase is obtained by fermenting *Actinoplanes utahensis*, separating the cells from the fermentation medium, washing the cells with water, extracting the cells with basic buffer at pH 8-11 for about 20 minutes, adjusting the extract to pH 7-8 and freeze-drying. The powdered form of the enzyme resulting from this process can be relatively stable and can be readily re-dissolved in water for use. Further purification can be obtained by gel filtration or other types of chromatography. This enzyme can deacylate, for example, N-[(2-sulfo)-9-fluorenylmethoxycarbonyl]$_5$ polymyxin B to obtain the protected polymyxin B decapeptide (protected deacylated PBpeptide-3). In other embodiments, the enzyme from *Actinoplanes utahensis* can be used as the whole broth from the fermentation or as the washed cells.

The enzyme from *Actinoplanes utahensis* can also be used as a water-solubilized preparation. The water-solubilized enzyme preparation can be obtained by a relatively strong basic extraction of the washed cells, followed by adjustment of the pH of the clear extract to pH 7-8. This water-solubilized enzyme preparation can be freeze-dried to a solid form.

Deacylation of the protected peptide provides a free amino terminus that can be modified by reaction with an addition reagent (Scheme IIa).

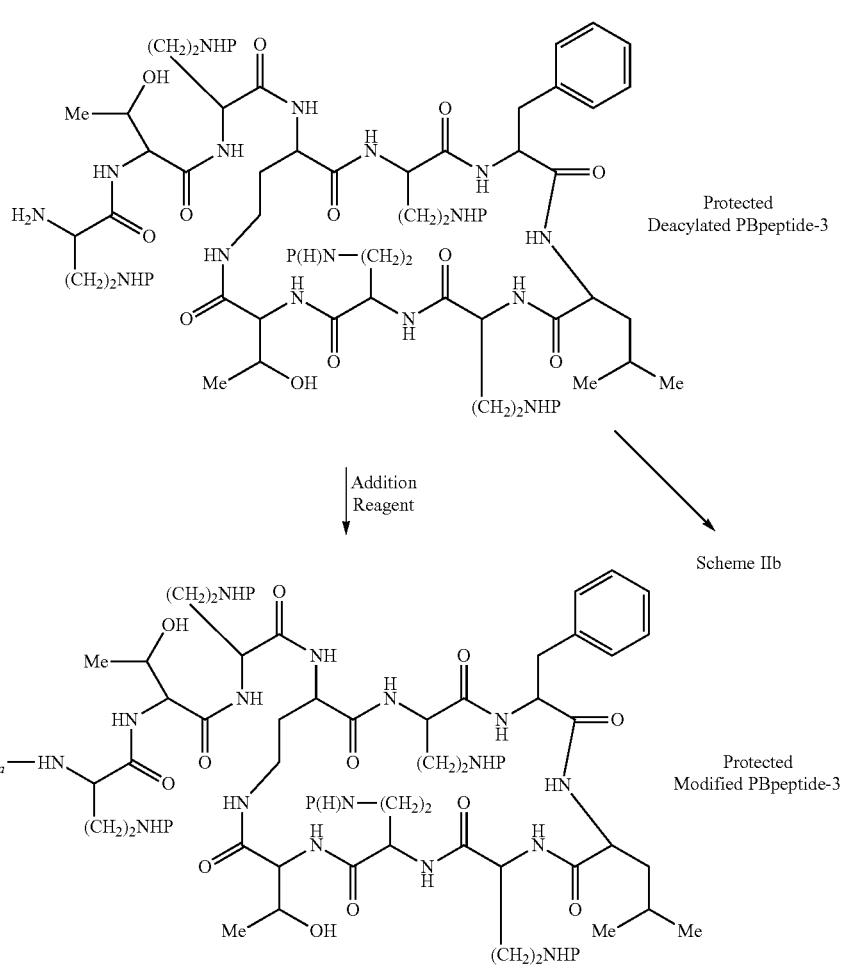

Scheme IIa illustrates the direct modification of the deacylated PBpeptide-3. Treatment of the deacylated PBpeptide-3 with an addition agent results in the formation of protected modified PBpeptide-3 compound. The reaction of an amine with an addition reagent, as defined herein, is well known to those skilled in the art. For example, treatment of deacylated protected PBpeptide-3 with an isocyanate gives compounds in which $R_a$—NH— is ureido. Similarly, treatment of deacylated protected PBpeptide-3 with an activated ester, lactone or acid chloride yields compounds in which $R_a$—NH— is acylamino. Treatment of deacylated protected PBpeptide-3 with a sulfonyl chloride or activated sulfonamide results compounds in which $R_a$—NH— is a sulfonamino. Treatment of deacylated protected PBpeptide-3 with an activated heterocycle results in a compound in which $R_a$—NH— is a heterocyclyl amino. Treatment of deacylated protected PBpeptide-3 with an activated heteroaryl results in a compound in which $R_a$—NH— is a heteroaryl amino. Treatment of deacylated protected PBpeptide-3 with a carbonate, chloroformate, or cyanoformate gives compounds in which $R_a$—NH— is a carbamate. Treatment of deacylated protected PBpeptide-3 with a thioacylester gives compounds in which $R_a$—NH— is thioacylamino. Treatment of deacylated protected PBpeptide-3 with a phosphoryl chloride or phosphoramidate, gives compounds in which $R_a$—NH— is phosphonamino. Treatment of deacylated protected PBpeptide-3 with an imidate or a ketenamine ($R''_2C$=$C$=$NH$) gives compounds in which $R_a$—NH— is iminoamino. Treatment of deacylated protected PBpeptide-3 with an isocyanate gives compounds in which $R_a$—NH— is ureido. Treatment of deacylated protected PBpeptide-3 with a thioisocyanate gives compounds in which $R_a$—NH— is thioureido. Treatment of deacylated protected PBpeptide-3 with an aldehyde or ketone under reductive conditions gives compounds in which $R_a$—NH— is a monosubstituted amino group or a disubstituted amino group. Nonlimiting examples of reducing agents include $H_2$/Ni (cat.), Zn/HCl, $NaBH_3CN$, $NaBH(OAc)_3$, $NaBH_4$, $BH_3$.pyridine, and formic acid. Treatment of deacylated protected PBpeptide-3 with a guanidinylating agent such as

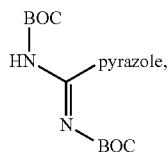

provides compounds in which $R_a$—NH— is guanidino.

It will be understood by those skilled in the art that if an addition agent contains substituents that are incompatible with the reaction conditions under which the protected modified PBpeptide is formed, said substituents can be protected prior to use in the reaction. Suitable protecting groups and methods of making them can be found in Greene (vide supra).

In another embodiment, one or more N-terminal amino acids may be removed from the exocyclic chain of the deacylated protected peptide. For example, a sequence of N-terminal amino acid hydrolyses, e.g., Edman degradations, modified Edman degradations or enzymatic reactions (e.g., catalyzed by an aminopeptidase), can be used to obtain the protected forms of other peptides, designated as the "peptide-0," "peptide-1," or "peptide-2," which contain zero, one or two amino acids, respectively, in the exocyclic chain.

The Edman degradation is a well-established reaction known to those skilled in the art (see, for example, P. Edman, 1950, *Acta Chem. Scan.* 4: 283-93 and P. Edman, 1956, *Acta Chem. Scan.* 10: 761-768). Exemplary methods for performing N-terminal amino acid hydrolyses are described in Voet et al., *Biochemistry*, 2nd Edition, John Wiley & Sons, New York, 1995, pp. 107-109, Creighton et al., *Proteins*, 2nd Edition, W.H. Freeman, New York, 1993, pp. 31-35, and Loudon et al., *Organic Chemistry*, 2nd Edition, Benjamin/Cummings, Menlo Park, Calif., 1988, pp. 1154-1161, the disclosures of which are incorporated herein by reference.

The Edman degradation can be carried out under a variety of conditions. In the first step of the Edman degradation, an isothiocyanate reacts with the terminal amine under neutral to mildly basic (pH<9.5) conditions in solvents such as, but not limited to, tetrahydrofuran, N,N'-dimethylformamide, dichloromethane, dioxane or ethanol to form a thiourea derivative of the peptide. A variety of isothiocyanates can be used (see K. K. Han et al. *Biochemie* 1977, 59: 557-576).

Upon treatment with acid or base, the thiourea peptide undergoes a cyclization reaction, giving a thiohydantoin and a peptide shorter by one amino acid residue. Subsequent cyclization and cleavage can be accomplished under a variety of conditions. Typically, anhydrous trifluoroacetic acid, heptafluorobutyric acid (see, for example, W. F. Brandt et al., 1976, *Z. Physiol. Chem.* 357: 1505-1508) or concentrated hydrochloric acid (see, for example, G. E. Tarr, 1977, *Methods Enzymol.* 47: 335-337) are used. Mild basic conditions such as triethylamine or N,N-dimethylallylamine/acetic acid (pH ~9) can also be used (see G. C. Barrett et al., 1985, *Tetrahedron Lett.* 26(36): 4375-4378). For a review of this reaction see K. K. Han, 1985, *Int. J. Biochem.* 17(4): 429-445). In one embodiment, cyclization and cleavage are accomplished under basic conditions.

In another embodiment, Scheme IIa illustrates modification of the protected deacylated PBpeptide-3 directly, for example, where the addition reagent is an acylamino reagent selected from R'—(C=O)-LG and R'—$SO_2$-LG, where LG is a leaving group. In some embodiments, an addition reagent may be an activated amino acid, or an amino acid and a peptide coupling reagent, such as, e.g., PyBOP® (benzotriazole-1-yl-oxy-tris-pyrrolidino-phosphonium hexafluorophosphate), HBtU (2-(1H-benzotriazole-1-yl)-1,1,3,3-tetramethyluronium hexafluorophosphate), HBtU/HOBt (2-(1H-benzotriazole-1-yl)-1,1,3,3-tetramethyluronium hexafluorophosphate/N-hydroxybenzotriazole), or DCC (dicyclohexylcarbodiimide). In one embodiment, R' and R'' are selected from alkyl, cycloalkyl, alkenyl, aryl, heteroaryl, and heterocyclyl. Nonlimiting examples of R'—(C=O)-LG include acyl halides, such as acyl chlorides, acyl cyanides, esters (e.g., succinimidyl esters), acyl azides, lactones, and anhydrides. Nonlimiting examples of R'—$SO_2$-LG include sulfonyl chlorides. When $R_a$ is an imine, R'—(C=NH)—, a modified PBpeptide-3 containing an iminoamino group may be formed by reacting deacylated PBpeptide-3 with a ketenamine $R''_2C$=$C$=$NH$, where R'' is selected from R' and hydrogen. When $R_a$ is an amide R'—NH—(C=O)— or a thioamide R'—NH—(C=S)—, a modified PB peptide 3 containing a urea or thiourea may be formed by reacting deacylated PB peptide 3 with an isocyanate or a isothiocyanate, respectively. When $R_a$ is a substituted alkyl, R'-alkyl-, a modified PBpeptide 3 containing the substituted alkyl may be formed by reacting deacylated PBpeptide 3 with R'C(O)R'' and a reducing agent. Nonlimiting examples of reducing agents include $H_2$/Ni (cat.), Zn/HCl, $NaBH_3CN$, NaBH $(OAc)_3$, $NaBH_4$, $BH_3$.pyridine, and formic acid.

Schemes IIb, III, and IV, schematically depict how "peptide-0," "peptide-1," or "peptide-2" versions of polymyxin B can be prepared (vide infra). Scheme IIb shows removal of an amino acid to convert protected deacylated PBpeptide-3 to protected deacylated PBpeptide-2. The protected deacylated PBpeptide-2 can then be chemically modified with the procedures described for $R_a$ above to install the $R_b$ substituent.

Scheme IIb

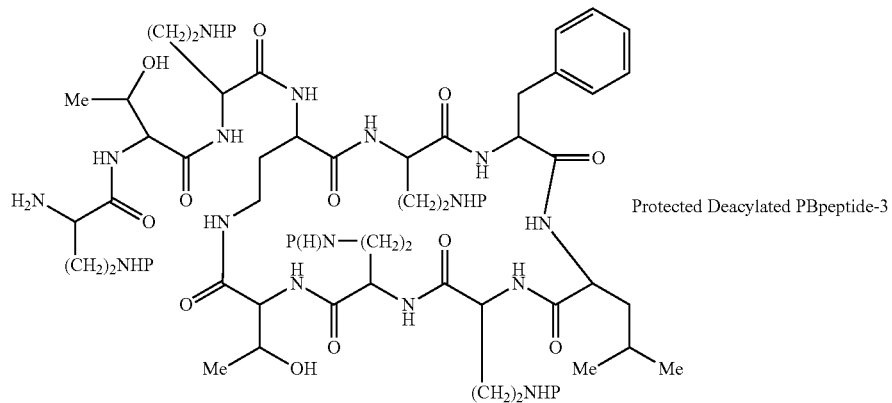

Protected Deacylated PBpeptide-3

| N-terminal amino acids hydrolysis

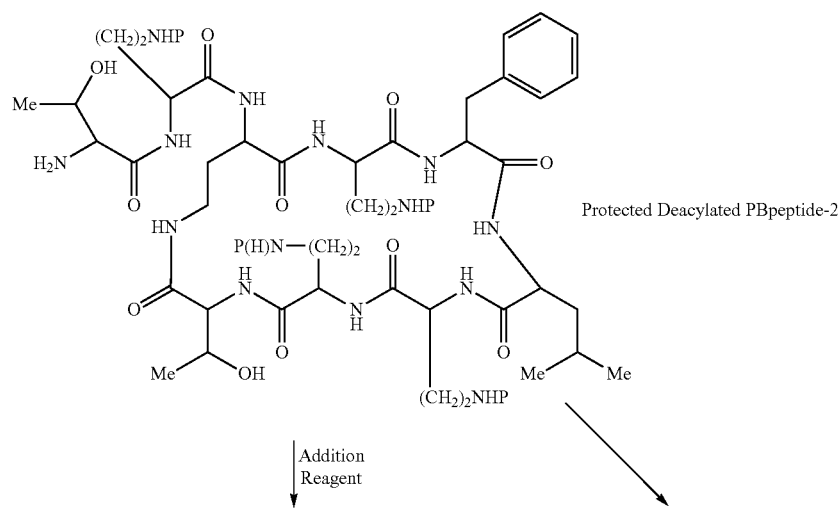

Protected Deacylated PBpeptide-2

| Addition Reagent

Scheme III

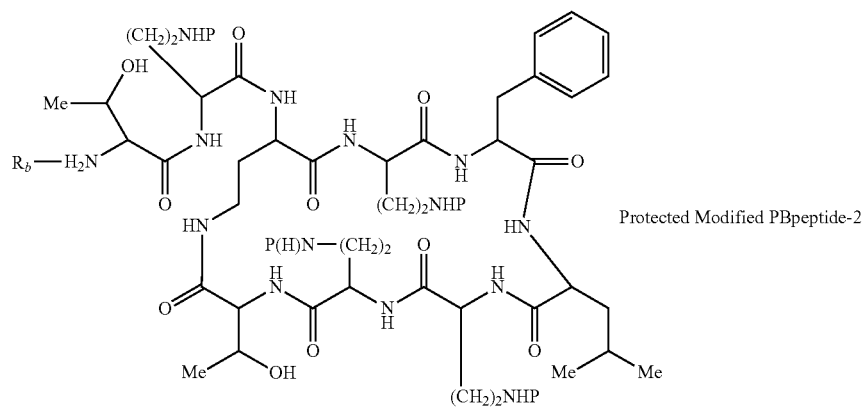

Protected Modified PBpeptide-2

Scheme III similarly shows conversion of protected deacylated PBpeptide-2 to protected deacylated PBpeptide-1, which can then be chemically modified with addition reagents, as described above, to install the $R_c$ substituent.

Scheme III

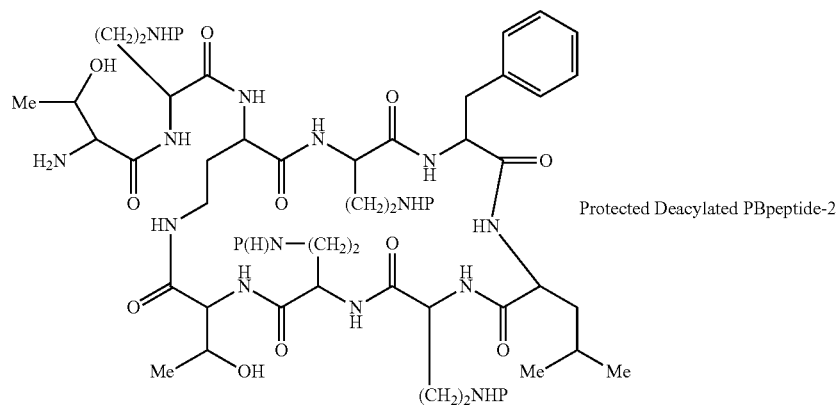

Protected Deacylated PBpeptide-2

↓ N-terminal amino acids hydrolysis

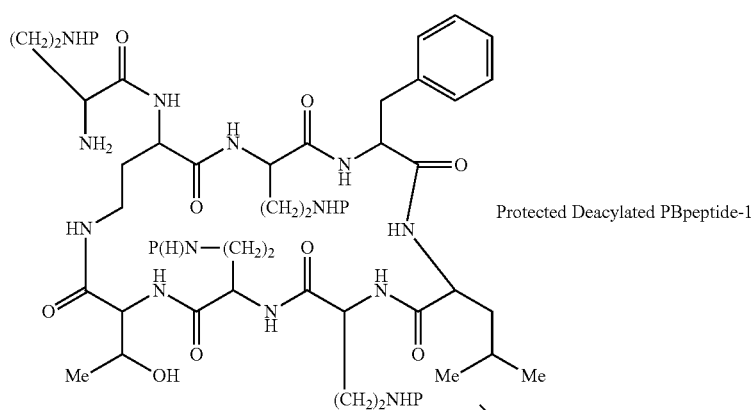

Protected Deacylated PBpeptide-1

↓ Addition Reagent

Scheme IV

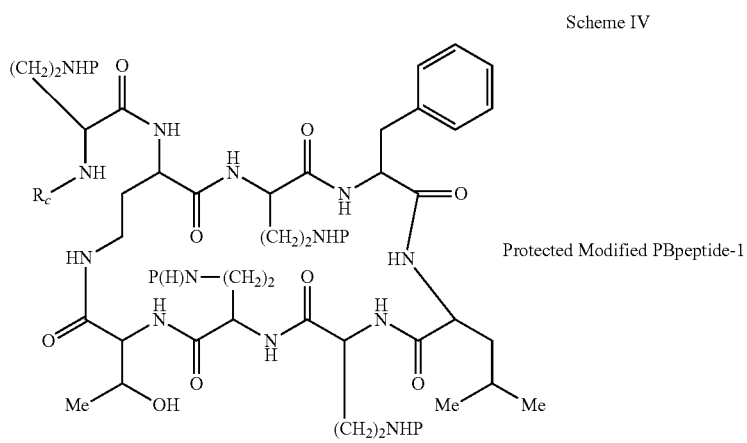

Protected Modified PBpeptide-1

Alternatively, deacylated protected PBpeptide-1 can be subjected to another N-terminal amino acid hydrolysis reaction (Scheme IV), to form deacylated protected PBpeptide-0, which does not contain an exocyclic peptide chain.

Scheme IV

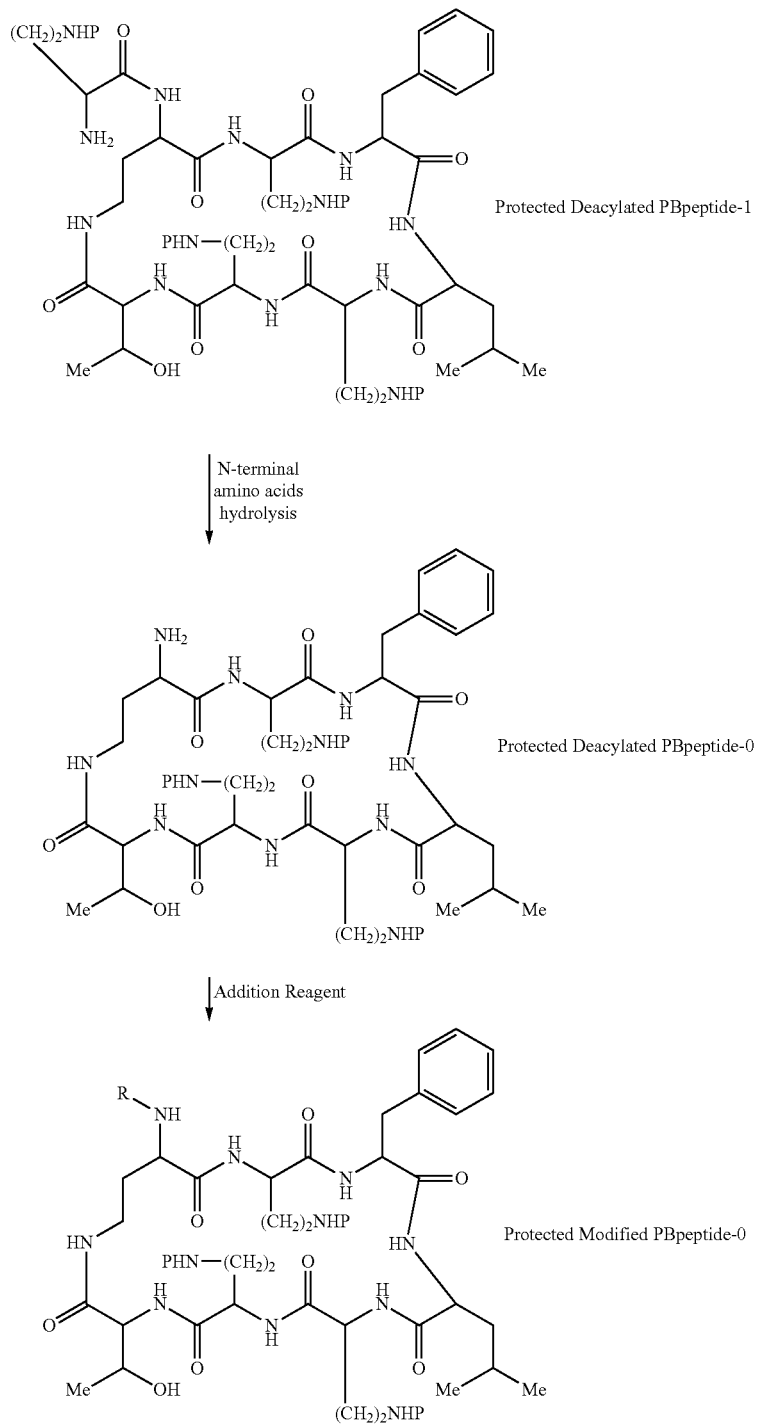

Although the Schemes above illustrate reactions involving polymyxin B derivatives, one of ordinary skill in the art can appreciate that these methods are equally applicable to any of the peptides disclosed herein.

One of ordinary skill in the art can appreciate that the hydrolysis/chemical modification steps need not strictly occur in separate reactions. For example, the hydrolysis and chemical modification steps can occur nearly simultaneously or can be performed in a one-pot reaction mixture.

Each of the protected peptides, such as the protected deacylated PBpeptide-2, can be used to make new peptides having antibacterial activity. For example, reagents that form the tail, e.g., alkyl or aromatic acids, can be converted to activated species and then coupled to the protected peptides, followed by deprotection to give new peptides, such as compounds 1, 2, 6, 7, 11, and 12 in Table 3. The protected peptides can also be treated directly with alkyl or aromatic isocyanates or isothiocyanates to give the corresponding ureas and thioureas, and the products deprotected to give another new series of novel peptides, as represented by compound 35. Ureas can also be prepared by treatment with N-carbonyloxysuccinimidyl derivatives of the appropriate amines. The latter derivatives are readily prepared from the reaction of amines and disuccinimidyl carbonate.

One embodiment provides a method for preparing a compound, comprising:

(a) treating a peptide having at least one side chain comprising an amino group with an amino protecting group reagent to form a protected peptide, wherein the peptide comprises a cyclic heptapeptide attached to an exocyclic peptide chain comprising an acyl group, and the protecting group comprises at least one acidic substituent; and (b) treating the protected peptide with a deacylating agent to form a protected, deacylated peptide.

In one embodiment, the peptide in step (a) has a structure of formula (A):

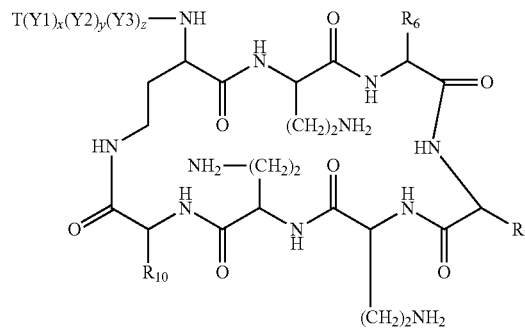

(A)

wherein:

Y1, Y2, and Y3 are each independently selected from amino acid residues; T is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; and $R_6$, $R_7$, and $R_{10}$ are each independently chosen from isopropyl, benzyl, isobutyl, sec-butyl, 1-hydroxy-1-ethyl, and hydroxymethyl. In another embodiment, $R_6$ and $R_7$ are each independently chosen from isopropyl, benzyl, isobutyl, sec-butyl, 1-hydroxy-1-ethyl, and hydroxymethyl and $R_{10}$ is chosen from isopropyl, isobutyl, sec-butyl, 1-hydroxy-1-ethyl, and hydroxymethyl. In another embodiment, Y1, Y2, and Y3 are each independently selected from 2,4-diaminobutanoic acid residue, threonine residue, and serine residue. In a further embodiment, T is chosen from 6-methyloctanoyl, 6-methylheptanoyl, octanoyl, heptanoyl, nonanoyl, and 3-hydroxy-6-methyloctanoyl.

In another embodiment, the peptide in step (a) is selected from polymyxin A, polymyxin B, [Ile$^7$]-polymyxin B, polymyxin C, polymyxin D, colistin, polymyxin F, polymyxin M, polymyxin P, polymyxin S, polymyxin T, circulin A, octapeptin A, octapeptin B, octapeptin C, and octapeptin D. In another embodiment, the peptide in step (a) is selected from polymyxin B, polymyxin A, polymyxin D, [Ile$^7$]-polymyxin B, colistin, circulin A, octapeptin B, and octapeptin C. In a further embodiment, the peptide in step (a) is selected from polymyxin A, polymyxin D, [Ile$^7$]-polymyxin B, colistin, circulin A, octapeptin B, and octapeptin C. In another embodiment, the peptide in step (a) is polymyxin B.

In one embodiment, the at least one acidic substituent is selected from carboxy, carboxylate, sulfo, sulfate, phosphonate, and salts thereof. Another embodiment provides a protecting group comprising an aryl or heteroaryl substituted with the at least one acidic substituent. In a further embodiment, the protecting group is a sulfonic acid of 9-fluorenylmethoxycarbonyl, such as 2-sulfo-9-fluorenylmethoxycarbonyl.

In one embodiment, the deacylating agent is an enzyme. The source of the enzyme is *Actinoplanes utahensis* in another embodiment.

In one embodiment, the method for preparing a compound further comprises step (c): forming from the protected deacylated peptide compounds having the following formulae:

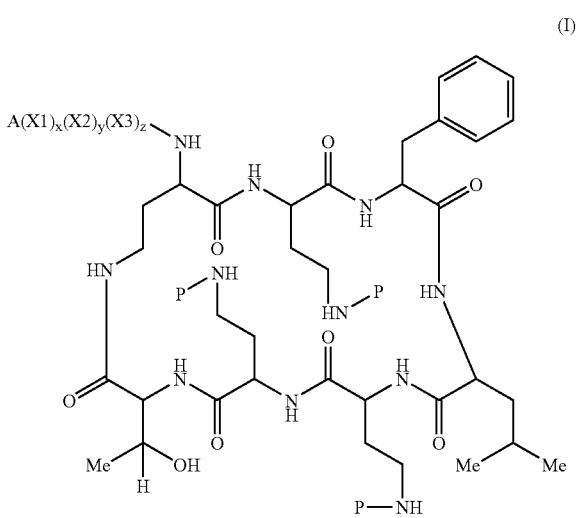

(I)

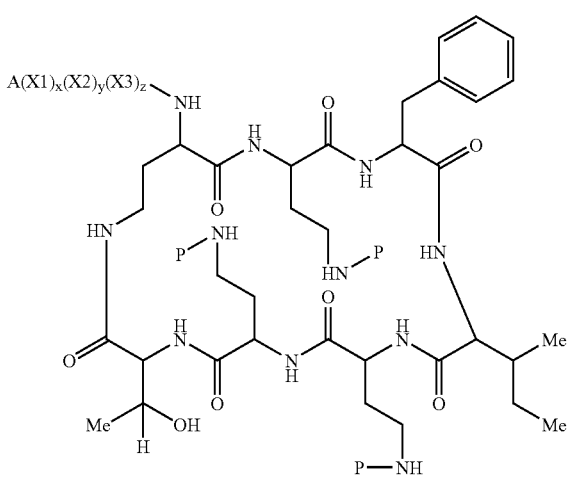

(II)

(III)

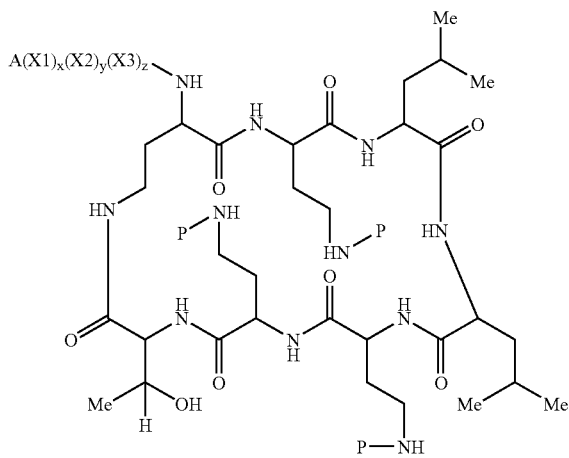

(IV)

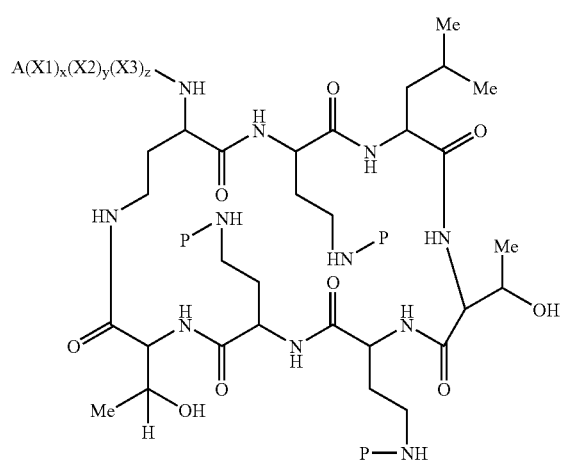

(V)

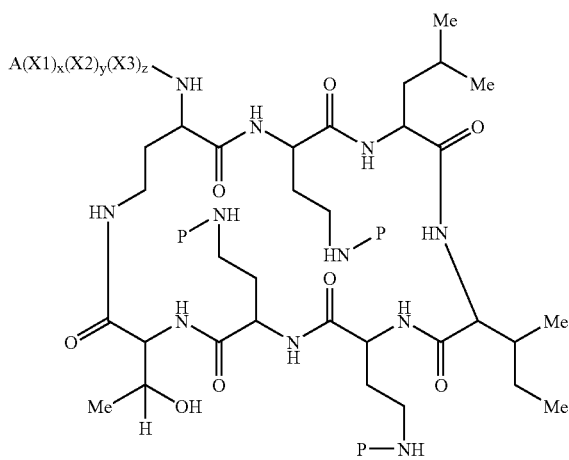

(VI)

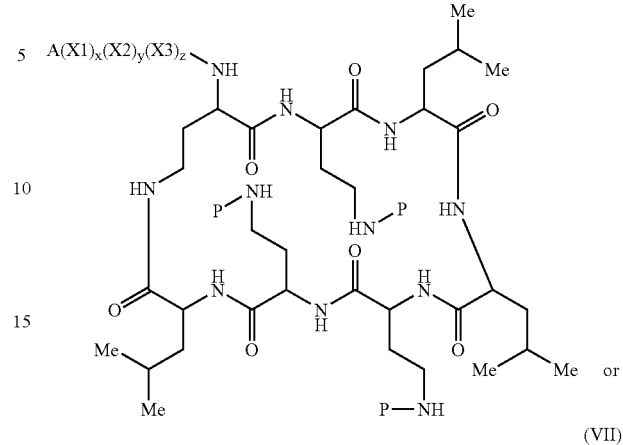

or (VII)

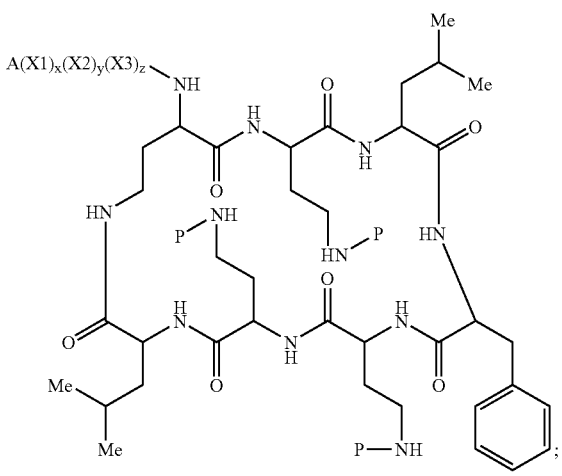

;

wherein A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; x, y, and z are integers independently selected from 0 and 1; and P is the protecting group containing at least one acidic substituent.

In another embodiment, the forming comprises treating the protected peptide with a reagent having the formula A-LG, wherein LG is a leaving group. In another embodiment, the forming comprises treating the protected peptide with a reagent selected from isocyanate, thioisocyanate, lactone, an activated heterocycle, an activated heteroaryl, imidate, ketenamine, an aldehyde and a reducing agent, and a ketone and a reducing agent. In a further embodiment, the forming comprises treating the protected peptide with an acylating reagent selected from acyl halides, acyl cyanides, esters, lactones, and anhydrides. In another embodiment, the forming comprises treating the protected peptide with a sulfonating reagent selected from sulfonyl chloride and activated sulfonamides.

In one embodiment, the forming comprises subjecting the protected deacylated peptide to an N-terminal amino acid hydrolysis reaction such that x is 0 and each of y and z is independently 1. In another embodiment, the forming comprises subjecting the protected deacylated peptide to a second N-terminal amino acid hydrolysis reaction such that each of x and y is independently 0 and z is 1. Another embodiment includes subjecting the protected deacylated peptide to a third N-terminal amino acid hydrolysis reaction such that each of x, y and z is 0.

One embodiment discloses a method for preparing a compound, comprising:

(a) treating a peptide having at least one side chain comprising an amino group with an amino protecting group reagent to form a protected peptide, wherein the peptide comprises a cyclic heptapeptide attached to an exocyclic peptide chain comprising an acyl group, and the protected peptide is water soluble; and (b) treating the protected peptide with a deacylating agent to form a protected, deacylated peptide.

One embodiment provides new protected peptides having a structure chosen from formulae (I)-(VII):

(I)
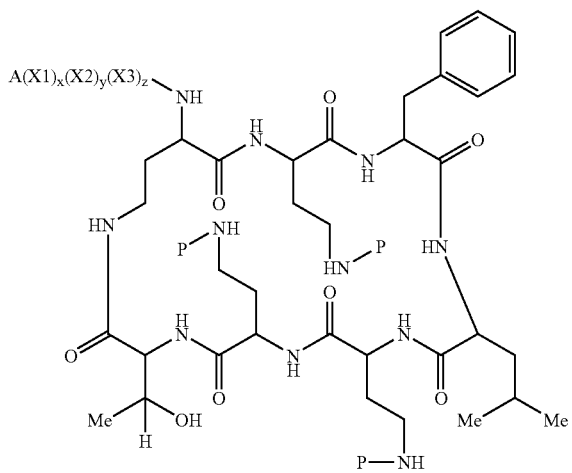

(II)
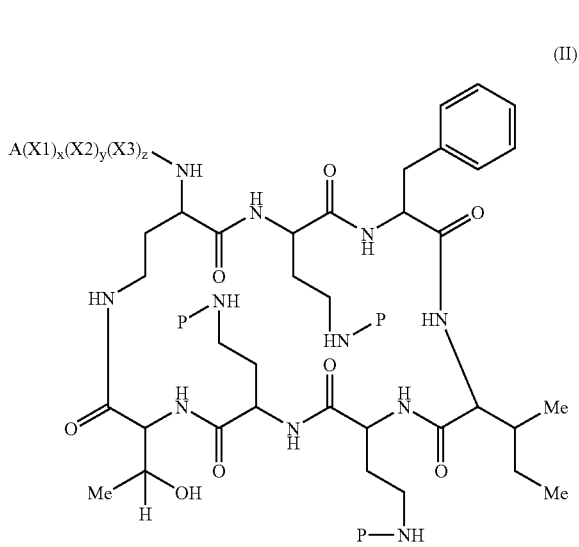

(III)
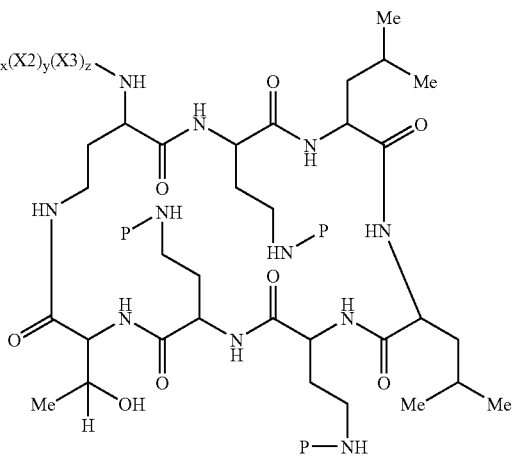

(IV)
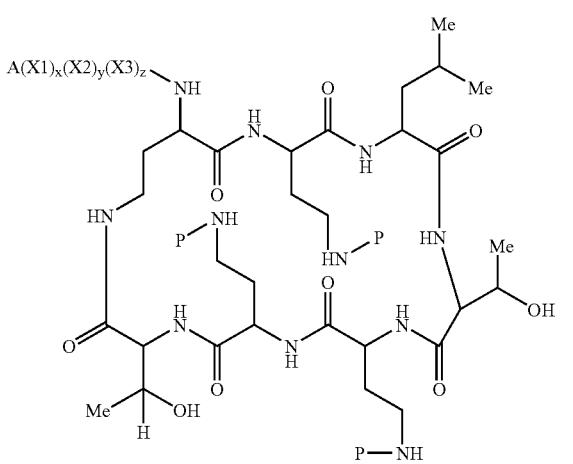

(V)
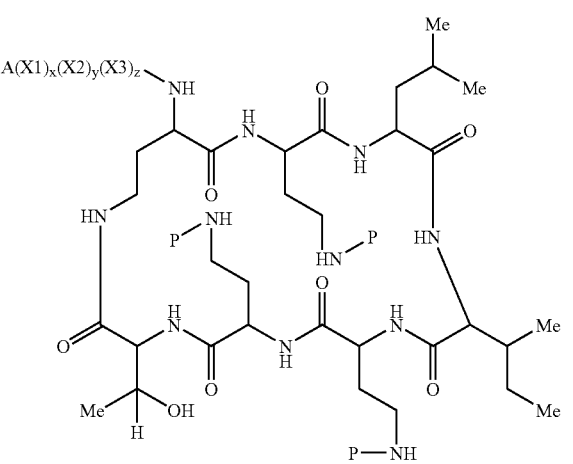

(VI)

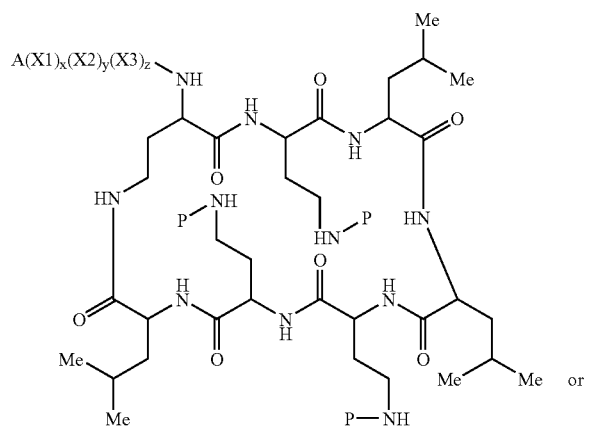

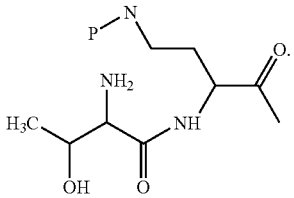

(VII)

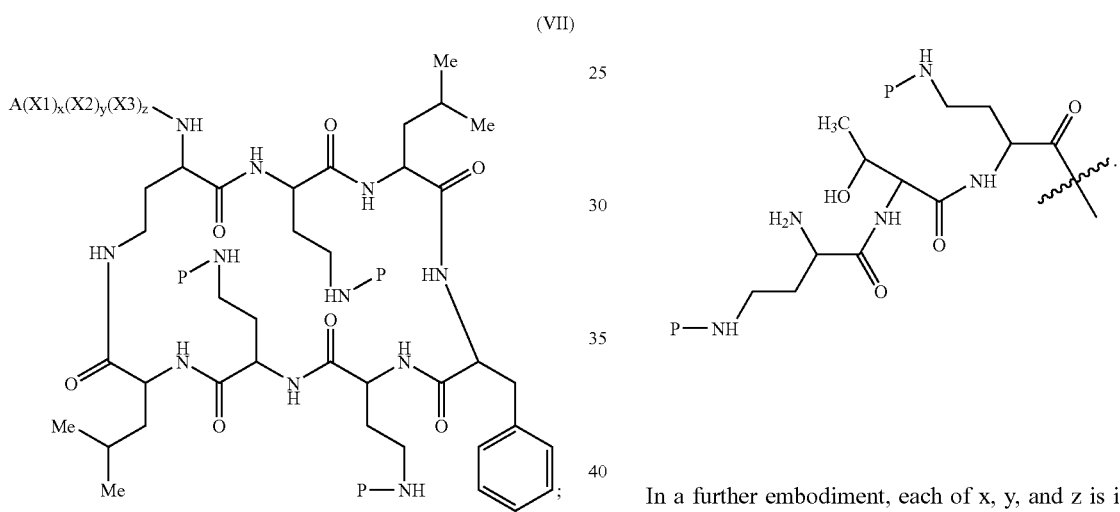

wherein A is selected from R'—(C═O)—, R'—SO₂—, R'—(C═NH)—, R'—NH—(C═S)—, R'—NH—(C═O)—, R'—NH—(C═NH)—, R'—O—(C═O)—, R'—O—(C═S)—, R'—P(O)OH—, R'—(C═S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; x, y, and z are integers independently selected from 0 and 1; and P is a protecting group containing at least one acidic substituent. In another embodiment, P is a 9-fluorenylmethoxycarbonyl group substituted with at least one acidic substituent, such as a 2-sulfo-9-fluorenylmethoxycarbonyl group. Another embodiment discloses the compound where x and y are each independently 0, z is 1, and X3 is:

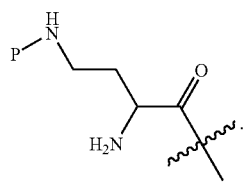

A further embodiment includes the compound where x is 0, each of y and z is independently 1, and X2-X3 is:

Another embodiment provides the compound where x, y, and z are each independently 1, and X1-X2-X3 is:

In a further embodiment, each of x, y, and z is independently 0 and A is hydrogen. In another embodiment, the compound is a prodrug.

One embodiment discloses a compound having a structure chosen from formulae (I)-(VII):

(I)

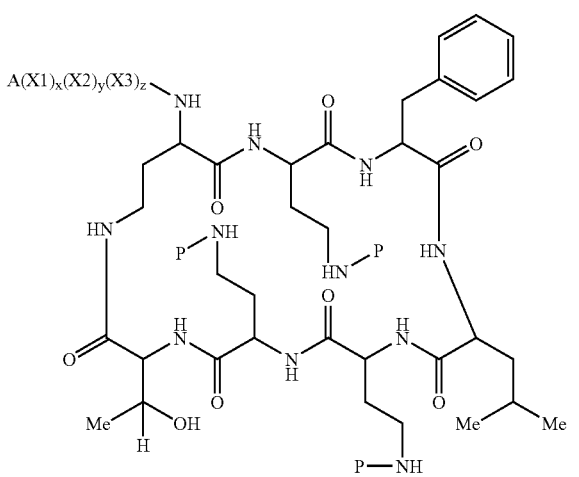

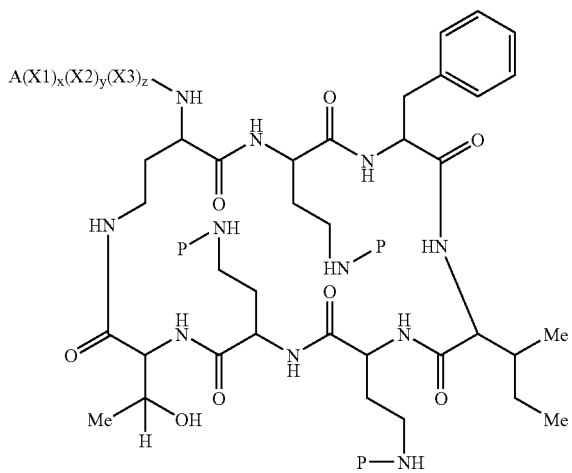
(II)

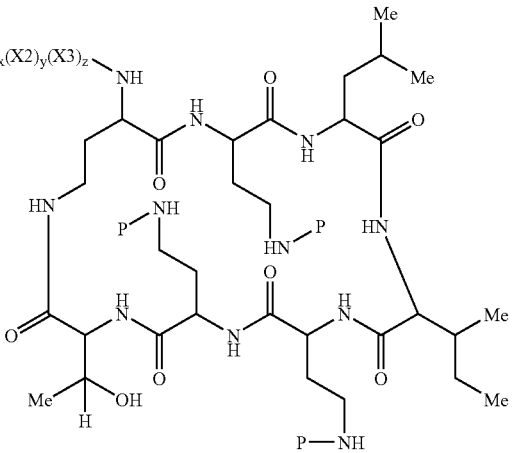
(V)

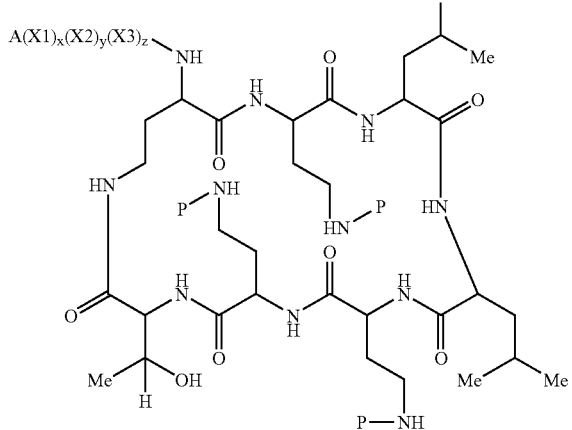
(III)

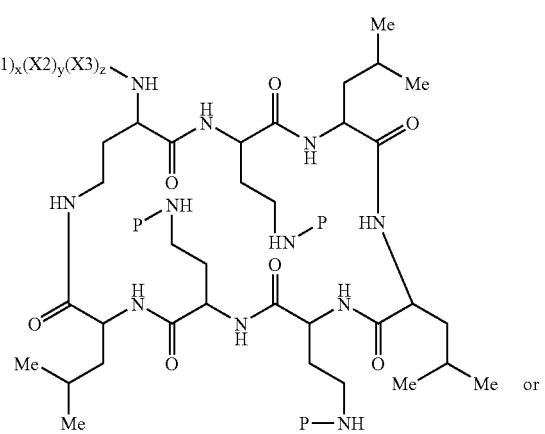
(VI)

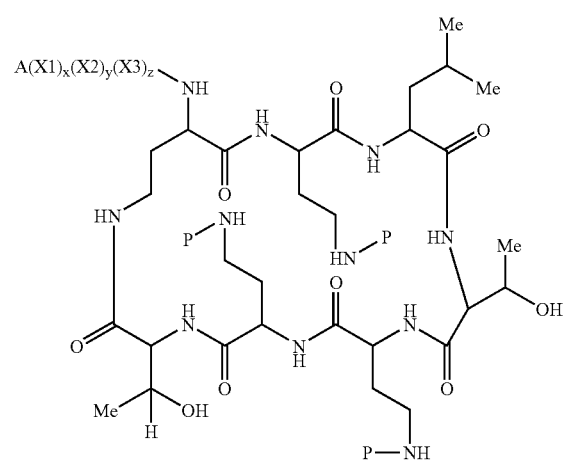
(IV)

or (VII)

wherein A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; x, y, and z are integers independently selected from 0 and 1; P is a protecting group; and the compound having a structure chosen from formulae (I)-(VII) is water-soluble.

Nonlimiting examples of amino acid residues for X1, X2, and X3 include those derived from the twenty encoded amino acids and derivatives thereof, other α-amino acids, β-amino acids, γ-amino acids, δ-amino acids, and ω-amino acids. X1, X2, and X3 may have either R or S chirality at any chiral atom. In one embodiment, X1, X2, and X3 are chosen from alanine, β-alanine, α-aminoadipic acid, α-aminobutanoic acid, γ-aminobutanoic acid, ε-aminocaproic acid, 1-aminocyclopentanecarboxylic acid, ε-aminohexanoic acid, 2-aminoheptanedioic acid, 7-aminoheptanoic acid, α-aminoisobutyric acid, aminomethylpyrrole carboxylic acid, 8-amino-3,6-dioxa-octanoic acid, aminopiperidinecarboxylic acid, 3-amino-propionic acid, aminoserine, aminotetrahydropyran-4-carboxylic acid, arginine, asparagine, aspartic acid, azetidine carboxylic acid, benzothiazolylalanine, butylglycine, carnitine, 4-chlorophenylalanine, citrulline, cyclohexylalanine, cyclohexylstatine, cysteine, diaminobutanoic acid, diaminopropionic acid, dihydroxyphenylalanine, dimethylthiazolidine carboxylic acid, glutamic acid, glutamine, glycine, histidine, homoserine, hydroxyproline, isoleucine, isonipecotic acid, leucine, lysine, methanoproline, methionine, norleucine, norvaline, ornithine, p-aminobenzoic acid, penicillamine, phenylalanine, phenylglycine, piperidinylalanine, piperidinylglycine, proline, pyrrolidinylalanine, sarcosine, selenocysteine, serine, statine, tetrahydropyranglycine, thienylalanine, threonine, tryptophan, tyrosine, valine, allo-isoleucine, allo-threonine, 2,6-diamino-4-hexanoic acid, 2,6-diaminopimelic acid, 2,3-diaminopropionic acid, dicarboxidine, homoarginine, homocitrulline, homocysteine, homocystine, homophenylalanine, homoproline, and 4-hydrazinobenzoic acid.

X1 and X2; X2 and X3; and X3 and the N-terminal residue of the cyclic heptapeptide may be joined by amide bonds. For example, in the embodiment wherein X1, X2, and X3 are α-amino acids, X1, X2, and X3 (having side chains R1, R2, and R3, respectively) may be connected as depicted below.

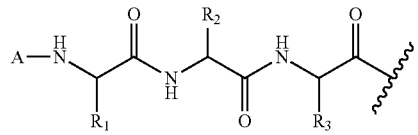

In some embodiments, X1 and X2 and/or X2 and X3 may be joined by ester bonds, as depicted below in the embodiment wherein X3 is serine.

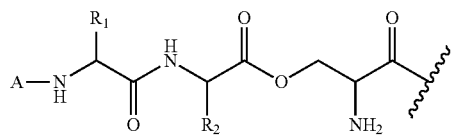

In embodiments wherein X1 or X2 has a side chain amino group, X1 and X2 and/or X2 and X3 may be connected through a side chain amide, as depicted below in the embodiment wherein X2 is ornithine.

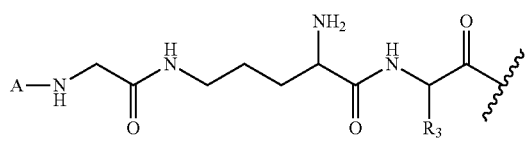

In one embodiment, the tail of the new peptide is depicted as "AB", where the "tail-exocyclic chain" portion has the formula $AB(X1)_x(X2)_y(X3)_z$—. In one embodiment, AB is selected from R'—(C=O)—, R'—SO$_2$—, R'—(C=NH)—, R'—NH—(C=S)—, R'—NH—(C=O)—, R'-alkyl, and hydrogen wherein R' is selected from alkyl, cycloalkyl, alkenyl, aryl, heteroaryl, and heterocyclyl.

In one embodiment, new compounds can be formed by removing the protecting groups from the protected peptide, i.e., by deprotection, by the methods described in "Protective Groups in Organic Synthesis" by Theodora W. Greene, John Wiley and Sons, New York, 1991, the disclosure of which is incorporated herein by reference.

Removal of amino protecting groups can be accomplished according to procedures described in Greene (vide supra). As those skilled in the art will recognize, the choice of amino protecting group employed in the first step of the process will dictate the reagents and procedures used in removing said amino protecting group.

When the reagent for the chemical modification contains one or more protecting group(s), those protecting group(s) must also be removed. The choice of the protecting group(s) utilized on the chemical modifying agent substituent(s) will dictate the reagents and procedures used in removing said protecting group(s). When the protecting group(s) utilized on the modifying agent substituent(s) and the protecting group utilized for the protected peptide are compatible, the protecting groups may be removed in a single step. However, when the protecting group(s) are incompatible multiple steps may be required to remove all of the protecting groups.

In one embodiment, the deprotected peptides are purified by gel filtration, chromatography, or reverse-phase HPLC.

One embodiment includes a compound of formula (1):

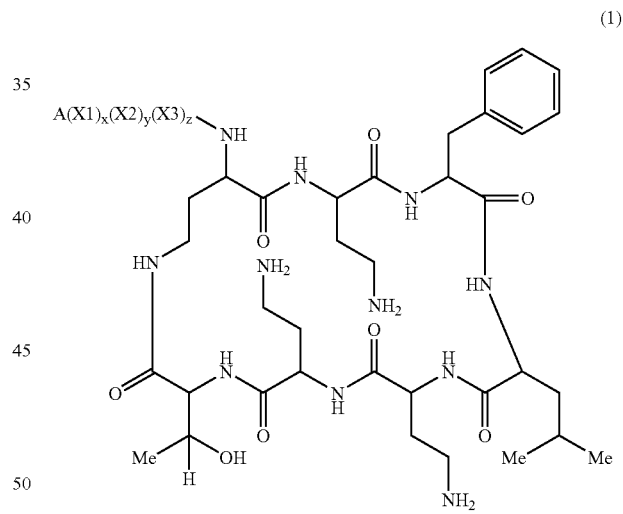

(1)

wherein A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; and x, y, and z are integers independently selected from 0 and 1, with the proviso that:
1) A does not comprise at least one amino acid residue;
2) if X3 is 2,4-diaminobutanoic acid, each of x and y is independently selected from 0 and 1, and A is R'—(C=O)—, then R' is selected from unsubstituted alkyl having at least 9 carbon atoms, cycloalkyl, alkenyl, aryl, heteroaryl, heterocyclyl, and substituted alkyl, wherein at least one hydrogen is replaced by a substituent group selected from acyl, acylamino, acyloxy, alkenyl, alkoxy, alkynyl, amino, aryl, aryloxy, carbamoyl, carboalkoxy, carboxy, carboxyamido, carboxyamino, cyano, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, and ureido, provided that the substituted alkyl is not selected from alkyl-CHOH—CH$_2$—, phenyl-CH$_2$—, adamantyl-CH$_2$—, substituted aryloxy-CH$_2$—, and CH$_3$—CHQ-CH$_2$—CH$_2$— wherein Q is the structure:

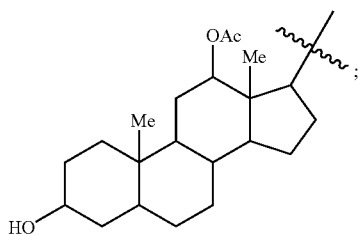

(Q)

3) if x, y and z are each 1, X1 is 2,4-diaminobutanoic acid, X2 is threonine, X3 is 2,4-diaminobutanoic acid, A is R'—(C=O)— and R' is aryl, then the aryl is not a 6-membered ring having three hydroxy substituents; and 4) if each of x, y, and z is independently 0 and A is R'—(C=O)—, then R' is selected from C$_{8-20}$-alkyl, cycloalkyl, alkenyl, aryl, heteroaryl, and heterocyclyl.

In another embodiment, if X3 is 2,4-diaminobutanoic acid, x and y are independently selected from 0 and 1, and A is R'—(C=O)—, then R' is selected from C$_{9-20}$ unsubstituted alkyl, cycloalkyl, alkenyl, aryl, heteroaryl, heterocyclyl and substituted alkyl, wherein at least one hydrogen is replaced by a substituent group selected from acyl, acylamino, acyloxy, alkenyl, alkoxy, alkynyl, amino, substituted aryl, carbamoyl, carboalkoxy, carboxy, carboxyamido, carboxyamino, cyano, disubstituted amino, formyl, guanidino, halo, heteroaryl, heterocyclyl, iminoamino, monosubstituted amino, nitro, oxo, phosphonamino, sulfinyl, sulfonamino, sulfonyl, thio, thioacylamino, thioureido, and ureido.

One embodiment provides a compound of formula (2):

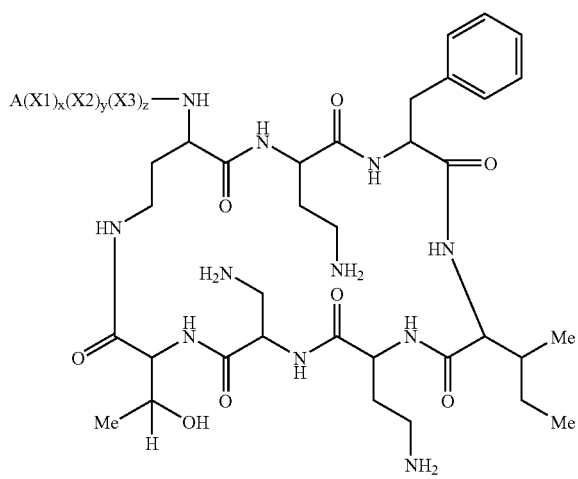

(2)

wherein A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; and x, y, and z are integers independently selected from 0 and 1, with the proviso that:

1) A does not comprise at least one amino acid residue; and 2) if each of x, y and z is independently 1, X1 is 2,4-diaminobutanoic acid, X2 is threonine, X3 is 2,4-diaminobutanoic acid, and A is R'—(C=O)—, then R' is not branched C$_8$-alkyl.

One embodiment discloses a compound selected from formulae (I)-(VII), (1) and (2), wherein X1 is 2,4-diaminobutanoic acid, X2 is threonine, X3 is 2,4-diaminobutanoic acid, A is R'—O—(C=O)— and R' is phenyl. Another embodiment provides a compound selected from formulae (I)-(VII), (1) and (2), wherein X1 is 2,4-diaminobutanoic acid, X2 is threonine, X3 is 2,4-diaminobutanoic acid, A is R'—(C=O)— and R' is n-C$_9$-alkyl. Another embodiment provides a compound selected from formulae (I)-(VII), (1) and (2), wherein X1 is 2,4-diaminobutanoic acid, X2 is threonine, X3 is 2,4-diaminobutanoic acid, A is R'—(C=O)— and R' is an alkyl substituted with a group selected from N—(C$_{1-10}$-alkyl)-4-aminophenyl and a benzyloxy group. A further embodiment includes a compound selected from formulae (I)-(VII), (1) and (2), wherein X1 is 2,4-diaminobutanoic acid, X2 is threonine, X3 is 2,4-diaminobutanoic acid, A is R'—NH—(C=O)— and R' is selected from n-C$_8$-alkyl, C$_2$-alkyl substituted with a 3-indolyl group, cyclohexyl, unsubstituted phenyl, benzyl, 4'-biphenyl, and phenyl substituted with a group selected from 4-C$_{10}$-alkyl, 4'-phenyloxy, and 4-chloro.

Another embodiment provides a compound selected from formulae (I)-(VII), (1) and (2), wherein X1 is 2,4-diaminobutanoic acid, X2 is threonine, X3 is 2,4-diaminobutanoic acid, A is R'—NH—(C=S)— and R' is phenyl. Another embodiment discloses a compound selected from formulae (I)-(VII), (1) and (2), wherein X1 is 2,4-diaminobutanoic acid, X2 is threonine, X3 is 2,4-diaminobutanoic acid, A is R'—(C=O)— and R' is selected from phenyl, 4-pyridinyl, and alkyl substituted with a 2-naphthoxy group. A further embodiment provides a compound selected from formulae (I)-(VII), (1) and (2), wherein X1 is 2,4-diaminobutanoic acid, X2 is threonine, X3 is 2,4-diaminobutanoic acid, A is R'—SO$_2$— and R' is 4-methylphenyl. Another embodiment includes a compound selected from formulae (I)-(VII), (1) and (2), wherein x is 0, each of y and z is independently 1, X2 is threonine, X3 is 2,4-diaminobutanoic acid, A is R'—NH—(C=O)— and R' is n-C$_8$-alkyl.

Another embodiment provides a compound selected from formulae (I)-(VII), (1) and (2), wherein x is 0, y and z are each 1, X2 is threonine, X3 is 2,4-diaminobutanoic acid, A is R'—NH—(C=S)— and R' is phenyl. A further embodiment includes a compound selected from formulae (I)-(VII), (1) and (2), wherein each of x and y is independently 0, z is 1, X3 is 2,4-diaminobutanoic acid, A is R'—NH—(C=O)— and R' is n-C$_9$-alkyl. Another embodiment discloses a compound selected from formulae (I)-(VII), (1) and (2), wherein X1 is glycine, X2 is threonine, X3 is 2,4-diaminobutanoic acid, A is R'—SO$_2$— and R' is n-C$_{10}$-alkyl. Another embodiment provides a compound selected from formulae (I)-(VII), (1) and (2), wherein X1 is lysine, X2 is threonine, X3 is 2,4-diaminobutanoic acid, A is R'—(C=O)— and R' is n-C$_9$-alkyl. A further embodiment includes a compound selected from formulae (I)-(VII), (1) and (2), wherein X1 is phenylalanine, X2 is threonine, X3 is 2,4-diaminobutanoic acid, A is R'—(C=O)— and R' is n-C$_9$-alkyl.

One embodiment provides a compound of formula (3):

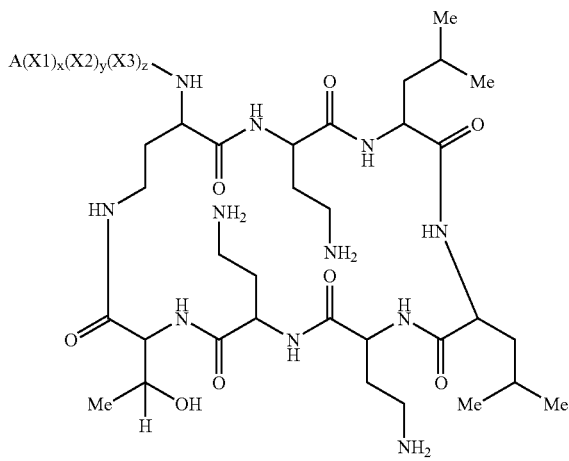

(3)

wherein A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; and x, y, and z are integers independently selected from 0 and 1, with the proviso that:

1) A does not comprise at least one amino acid residue;

2) if x is selected from 0 or 1, each of y and z is independently 1, X1 is an amino acid residue, X2 is threonine, X3 is 2,4-diaminobutanoic acid and A is R'—(C=O)—, then R' is selected from unbranched unsubstituted $C_{1-4}$-alkyl, cycloalkyl, alkenyl, aryl, heteroaryl and heterocyclyl, provided that: a) the alkenyl is not furanyl-CH=CH—, b) the aryl is not selected from naphthyl and 4-nitrophenyl, and c) the heteroaryl is not 2-thiophenyl; and 3) if x is selected from 0 or 1, each of y and z is independently 1, X1 is an amino acid residue, X2 is threonine, X3 is 2,4-diaminobutanoic acid and A is R'—SO$_2$—, then R' is selected from $C_{1-7}$-alkyl, $C_{9-20}$-alkyl, cycloalkyl, alkenyl, heteroaryl, and heterocyclyl.

Another embodiment includes a compound of formula (3), wherein if x is selected from 0 or 1, y and z are each 1, X1 is an amino acid residue, X2 is threonine, X3 is 2,4-diaminobutanoic acid and A is R'—(C=O)—, then R' is selected from unbranched unsubstituted $C_{1-4}$ alkyl, cycloalkyl, and heterocyclyl. Another embodiment provides a compound of formula (3), wherein X1 is 2,4-diaminobutanoic acid, X2 is threonine, X3 is 2,4-diaminobutanoic acid, A is R'—NH—(C=O)— and R' is n-$C_8$-alkyl. A further embodiment discloses a compound of formula (3), wherein X1 is 2,4-diaminobutanoic acid, X2 is threonine, X3 is 2,4-diaminobutanoic acid, A is R'—SO$_2$— and R' is 4-methylphenyl.

One embodiment provides a compound of formula (4):

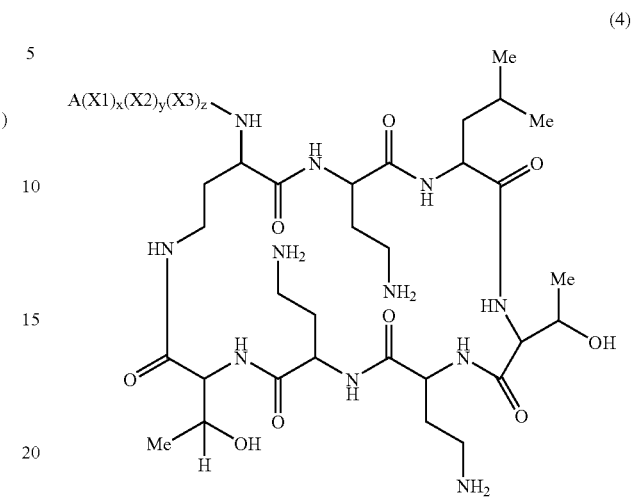

(4)

wherein A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; and x, y, and z are integers independently selected from 0 and 1, with the proviso that if x, y and z are each 1, X1 is 2,4-diaminobutanoic acid, X2 is threonine, X3 is 2,4-diaminobutanoic acid, and A is R'—(C=O)—, then R' is not branched $C_{8-9}$-alkyl. In another embodiment, A does not comprise at least one amino acid residue.

One embodiment includes a compound of formula (5):

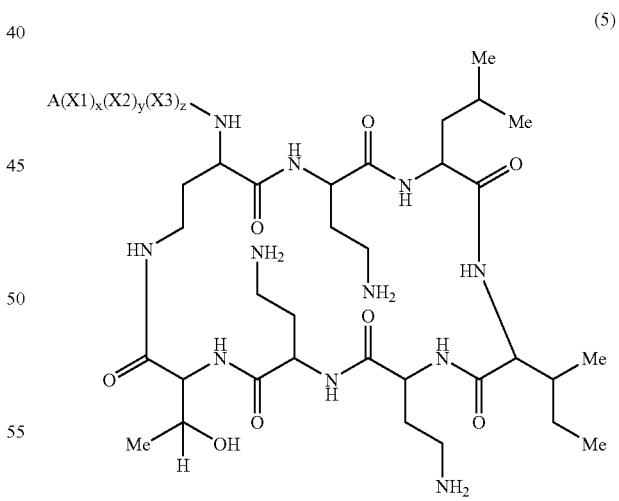

(5)

wherein A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; and x, y, and z are integers independently selected from 0 and 1, with the proviso that if x, y and z are each 1, X1 is 2,4-diaminobutanoic acid, X2 is threonine, X3 is 2,4-diaminobutanoic acid, and A is R'—(C=O)—, then R' is not branched $C_{7-8}$-alkyl. In another embodiment, A does not comprise at least one amino acid residue.

One embodiment provides a compound of formula (6):

(6)

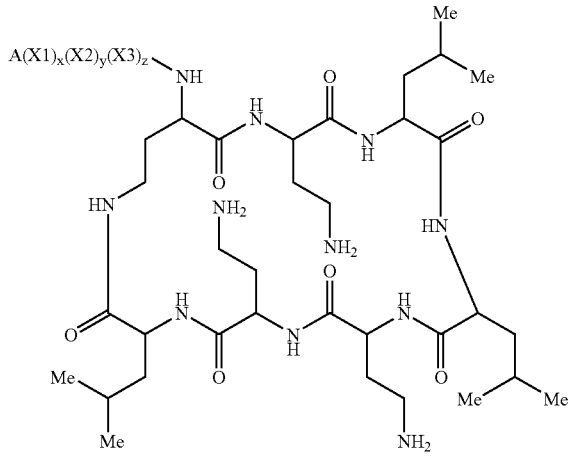

wherein A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; and x, y, and z are integers independently selected from 0 and 1, with the proviso that if each of x and y is independently 0, z is 1, X3 is 2,4-diaminobutanoic acid, and A is R'—(C=O)—, then R' is selected from substituted alkyl, cycloalkyl, alkenyl, aryl, heteroaryl, and heterocyclyl, provided that the substituted alkyl a) is not substituted with an oxazolidine, or b) is not of the formula alkyl-CHOH—CH$_2$—. In another embodiment, A does not comprise at least one amino acid residue.

One embodiment discloses a compound of formula (6):

(6)

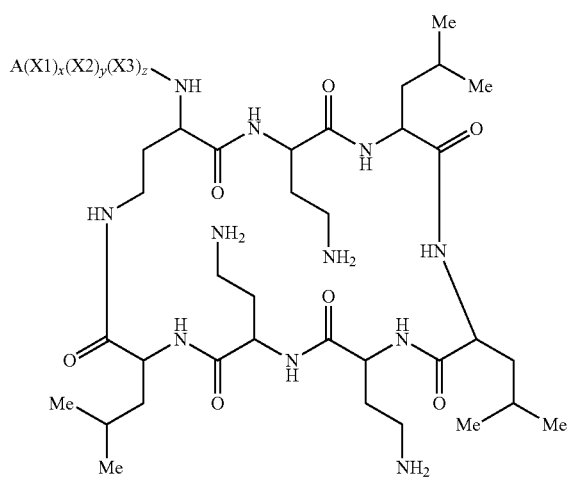

wherein A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; and x, y, and z are integers independently selected from 0 and 1, with the proviso that if each of x and y is independently 0, z is 1, X3 is 2,4-diaminobutanoic acid, and A is R'—(C=O)—, then R' is selected from substituted alkyl, cycloalkyl, alkenyl, aryl, heteroaryl, and heterocyclyl, provided that the substituted alkyl a) is not substituted with an oxazolidine, or b) is not of the formula alkyl-CHOH—CH$_2$—. In another embodiment, A does not comprise at least one amino acid residue. In a further embodiment, if each of x and y is independently 0, z is 1, X3 is 2,4-diaminobutanoic acid, and A is R'—(C=O)—, then R' is selected from substituted $C_{1-7}$-alkyl, substituted $C_{12-20}$-alkyl, cycloalkyl, alkenyl, aryl, heteroaryl, and heterocyclyl.

One embodiment provides a compound of formula (7):

(7)

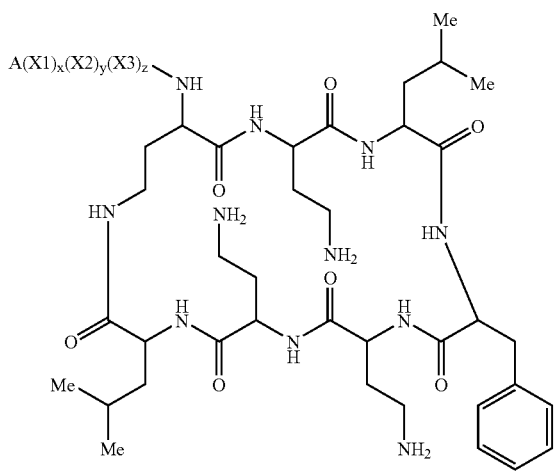

wherein A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; and each of x, y, and z is an integer independently selected from 0 and 1, with the proviso that if each of x and y is independently 0, z is 1, X3 is 2,4-diaminobutanoic acid, and A is R'—(C=O)—, then R' is not branched $C_{9-11}$-alkyl with a hydroxyl substituent. In another embodiment, A does not comprise at least one amino acid residue.

One embodiment includes a compound of formula (1):

(1)

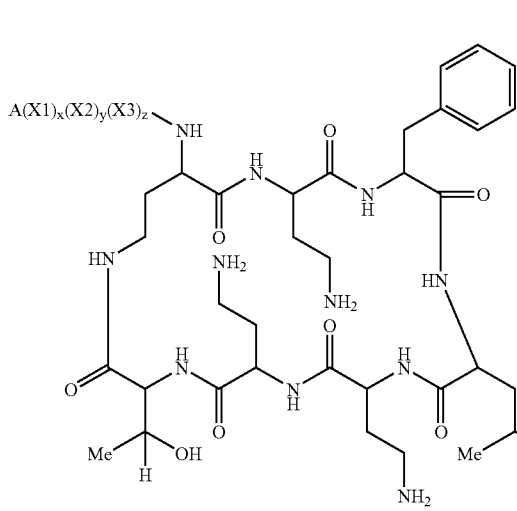

wherein A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; and x, y, and z are integers independently selected from 0 and 1, with the proviso that:

1) if X3 is 2,4-diaminobutanoic acid, each of x and y is independently selected from 0 and 1, and A is R'—(C=O)—, then R' is selected from unsubstituted alkyl having at least 9 carbon atoms, cycloalkyl, alkenyl, aryl, heteroaryl, heterocyclyl, and substituted alkyl, wherein at least one hydrogen is replaced by a substituent group selected from acyl, acylamino, acyloxy, alkenyl, alkoxy, alkynyl, amino, aryl, aryloxy, carbamoyl, carboalkoxy, carboxy, carboxyamido, carboxyamino, cyano, disubstituted amino, formyl, guanidino, halo, heteroaryl, heterocyclyl, hydroxy, iminoamino, monosubstituted amino, nitro, oxo, phosphonamino, sulfinyl, sulfonamino, sulfonyl, thio, thioacylamino, thioureido, and ureido, provided that the substituted alkyl is not selected from alkyl-CHOH—CH$_2$—, phenyl-CH$_2$—, adamantyl-CH$_2$—, substituted aryloxy-CH$_2$—, and CH$_3$—CHQ-CH$_2$—CH$_2$— wherein Q is the structure:

Q

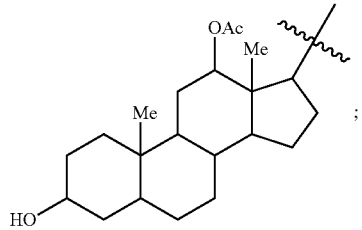

2) if x, y and z are each 1, X1 is 2,4-diaminobutanoic acid, X2 is threonine, X3 is 2,4-diaminobutanoic acid, A is R'—(C=O)— and R' is aryl, then the aryl is not a 6-membered ring having three hydroxy substituents; and 3) if each of x, y, and z is independently 0, then A is selected from C$_{8-20}$-alkyl, cycloalkyl, alkenyl, aryl, heteroaryl, and heterocyclyl.

Another embodiment provides a compound selected from formulae (I)-(VII) and (1), wherein X1 is 2,4-diaminobutanoic acid, X2 is threonine, X3 is 2,4-diaminobutanoic acid, and A is an N$^\alpha$-(n-C$_9$-alkanoyl)lysine.

One embodiment includes a compound of formula (2):

(2)

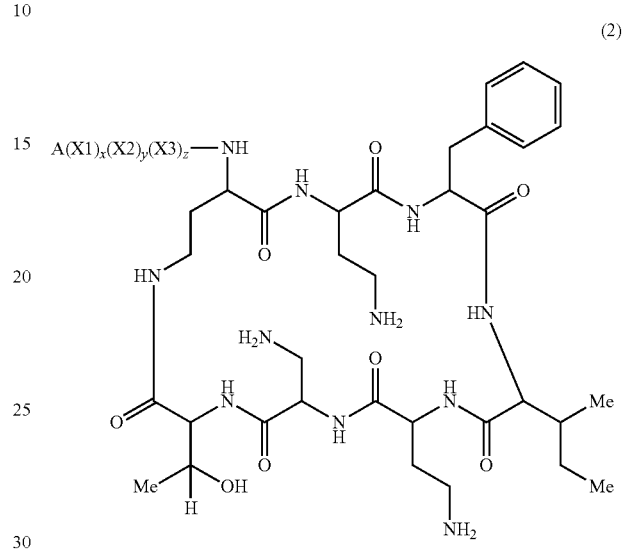

wherein A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; and x, y, and z are integers independently selected from 0 and 1, with the proviso that if each of x, y and z is independently 1, X1 is 2,4-diaminobutanoic acid, X2 is threonine, X3 is 2,4-diaminobutanoic acid, and A is R'—(C=O)—, then R' is not branched C$_8$-alkyl.

One embodiment discloses a compound of formula (3):

(3)

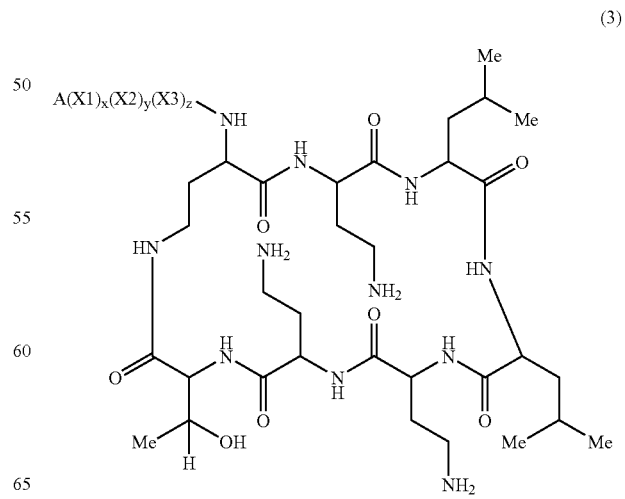

wherein:

A is selected from R'—(C=O)—, R'—SO$_2$—, R'—(C=NH)—, R'—NH—(C=S)—, R'—NH—(C=O)—, R'—NH—(C=NH)—, R'—O—(C=O)—, R'—O—(C=S)—, R'—P(O)OH—, R'—(C=S)—, R'-alkyl-, R'—, and hydrogen; R' is selected from alkyl, cycloalkyl, alkenyl, aryl, heteroaryl, and heterocyclyl; X1, X2, and X3 are each independently selected from amino acid residues; and x, y, and z are integers independently selected from 0 and 1, with the proviso that:

1) if x is selected from 0 or 1, each of y and z is independently 1, X1 is an amino acid residue, X2 is threonine, X3 is 2,4-diaminobutanoic acid and A is R'—, then R' is selected from N$^\alpha$-alkanoylphenylalanine, N$^\alpha$-alkenoylphenylalanine, N$^\alpha$-arylcarbonylphenylalanine, N$^\alpha$-heteroarylcarbonylphenylalanine;

2) if x is selected from 0 or 1, each of y and z is independently 1, X1 is an amino acid residue, X2 is threonine, X3 is 2,4-diaminobutanoic acid and A is R'—(C=O)—, then R' is selected from unbranched unsubstituted cycloalkyl, alkenyl, aryl, heteroaryl and heterocyclyl, provided that: a) the alkenyl is not furanyl-CH=CH—, b) the aryl is not selected from naphthyl and 4-nitrophenyl, and c) the heteroaryl is not 2-thiophenyl; and 3) if x is selected from 0 or 1, each of y and z is independently 1, X1 is an amino acid residue, X2 is threonine, X3 is 2,4-diaminobutanoic acid and A is R'—SO$_2$—, then R' is selected from C$_{1-7}$-alkyl, C$_{9-20}$-alkyl, cycloalkyl, alkenyl, heteroaryl, and heterocyclyl.

Another embodiment includes a compound selected from formulae (I)-(VII) and (1)-(3), wherein X1 is 2,4-diaminobutanoic acid, X2 is threonine, X3 is 2,4-diaminobutanoic acid, A is R'—(C=O)— and R' is an N$^\alpha$-(n-C$_9$-alkanoyl)phenylalanine.

One embodiment includes a method for treating an infection in a subject by administering a therapeutically-effective amount of a pharmaceutical composition comprising a compound selected from formulae (I)-(VII) and (1)-(7) and a pharmaceutically acceptable carrier.

Antibacterial Activity

The antibacterial activities of certain new compounds are indicated in Table 4 as their minimum inhibitory concentrations (MICs) against *Escherichia coli*, *Staphylococcus aureus*, and *Pseudomonas aeruginosa*. MICs can be determined by the conditions disclosed in Table 4, as well as in Jarolmen, H. et al., "Activity of Minocycline Against R-Factor Carrying Enterobacteriaceae," *Infectious Immunity*, Vol. 1, No. 4, pp. 321-326, 1970, the disclosure of which is incorporated herein by reference.

Pro-Drugs

In one embodiment, pro-drugs of disclosed peptides are provided. Peptides having the heptapeptide structure of formula (B) and protected with HSO$_3$-Fmoc and/or other amino protecting groups comprising at least one acidic group are antibacterial pro-drugs. The HSO$_3$-Fmoc group is cleaved after introduction into an animal, such as, e.g., a mammal, including a human, liberating the biologically active peptide. Administration of a biologically active peptide as the protected pro-drug may result in a slow release mechanism for the antibacterial compound. A discussion of pro-drugs is provided in Refs. 32-33.

Pharmaceutical Compositions

Also disclosed are pharmaceutical compositions or formulations comprising compounds disclosed herein, or salts thereof.

The pharmaceutical compositions can be formulated for oral, intravenous, intramuscular, subcutaneous or parenteral administration for the therapeutic or prophylactic treatment of diseases, such as bacterial infections.

The pharmaceutical preparations disclosed herein may be prepared in accordance with standard procedures and are administered at dosages that are selected to reduce, prevent or eliminate infection (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of the methods for administering various antimicrobial agents for human therapy).

The pharmaceutical compositions can comprise one or more of the compounds disclosed herein in association with one or more nontoxic, pharmaceutically-acceptable carriers and/or diluents and/or adjuvants and/or excipients. As used herein, the phrase "pharmaceutically-acceptable carrier" refers to any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. Nonlimiting examples of carriers and excipients include corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral or parenteral administration, compounds of the present invention can be mixed with conventional pharmaceutical carriers and excipients and used in the form of tablets, capsules, elixirs, suspensions, syrups, wafers and the like. The compositions comprising a compound of this invention may contain from about 0.1% to about 99% by weight of the active compound, such as from about 10% to about 30%.

For oral use, solid formulations such as tablets and capsules are useful. Sustained release or enterically coated preparations may also be devised. For pediatric and geriatric applications, one embodiment provides suspensions, syrups and chewable tablets. For oral administration, the pharmaceutical compositions are in the form of, for example, a tablet, capsule, suspension or liquid.

The pharmaceutical compositions may be made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs, preparations of the invention may contain conventional additives such as suspending agents, emulsifying agents, non-aqueous agents, preservatives, coloring agents and flavoring agents. Nonlimiting examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, the pharmaceutical composition can be dissolved or suspended in any of the commonly used intravenous fluids and administered by infusion. Intravenous fluids include, without limitation, physiological saline or Ringer's solution. Intravenous administration may be accomplished by using, without limitation, syringe, minipump or intravenous line.

Pharmaceutical compositions of this invention for parenteral injection comprise pharmaceutically-acceptable aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, benzyl alcohol, polyols (such as glycerol, propylene glycol, and polyethylene glycol), and suitable mixtures thereof, vegetable oils (such as corn oil or olive oil), and injectable organic esters such as ethyl oleate. Proper fluidity can be maintained, for example, by the use of coating materials such as lecithin, by the maintenance of the required particle size in the case of dispersions, and by the use of surfactants. The compositions can include various buffers.

These compositions may also contain adjuvants such as preservatives, wetting agents, emulsifying agents, and dispersing agents. They may also contain taggants or other anticounterfeiting agents, which are well known in the art. Prevention of the action of microorganisms may be ensured by the inclusion of various antibacterial and antifungal agents, for example, paraben, chlorobutanol, and phenol sorbic acid. It may also be desirable to include isotonic agents such as sugars and sodium chloride. Prolonged absorption of the injectable pharmaceutical form may be brought about by the inclusion of agents which delay absorption, such as aluminum monostearate and gelatin.

Injectable depot forms can be made by forming microencapsulating matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations can also be prepared by entrapping the drug in liposomes or microemulsions, which are compatible with body tissues.

The injectable formulations can be sterilized, for example, by filtration through a bacterial-retaining filter, or by incorporating sterilizing agents in the form of sterile solid compositions, which can be dissolved or dispersed in sterile water or other sterile injectable medium just prior to use.

Solid dosage forms for oral administration include capsules, tablets, pills, powders, and granules. Such forms may include forms that dissolve or disintegrate quickly in the oral environment. In such solid dosage forms, the active compound can be mixed with at least one inert, pharmaceutically-acceptable excipient or carrier. Suitable excipients include, for example, (a) fillers or extenders such as starches, lactose, sucrose, glucose, mannitol, and silicic acid; (b) binders such as cellulose and cellulose derivatives (such as hydroxypropylmethylcellulose, hydroxypropylcellulose, and carboxymethylcellulose), alginates, gelatin, polyvinylpyrrolidone, sucrose, and acacia; (c) humectants such as glycerol; (d) disintegrating agents such as sodium starch glycolate, croscarmellose, agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents, such as cetyl alcohol and glycerol monostearate, fatty acid esters of sorbitan, poloxamers, and polyethylene glycols; (h) absorbents such as kaolin and bentonite clay; (i) lubricants such as talc, calcium stearate, magnesium stearate, solid polyethylene glycols, sodium lauryl sulfate, and mixtures thereof; and (j) glidants such as talc, and silicone dioxide. Other suitable excipients include, for example, sodium citrate or dicalcium phosphate. The dosage forms may also comprise buffering agents.

Solid dosage forms, including those of tablets, dragees, capsules, pills, and granules, can be prepared with coatings and shells such as functional and aesthetic enteric coatings and other coatings well known in the pharmaceutical formulating art. They may optionally contain opacifying agents and colorants. They may also be in a form capable of controlled or sustained release. Examples of embedding compositions that can be used for such purposes include polymeric substances and waxes.

The pharmaceutical compositions can be delivered using controlled (e.g., capsules) or sustained release (e.g., bioerodable matrices) delivery systems. Exemplary delayed release delivery systems for drug delivery that are suitable for administering the pharmaceutical compositions are described in U.S. Pat. Nos. 4,452,775 (issued to Kent), 5,239,660 (issued to Leonard), and 3,854,480 (issued to Zaffaroni).

In some cases, in order to prolong the effect of the drug, it may be desirable to slow the absorption of the drug following subcutaneous or intramuscular injection. This may be accomplished by the use of a liquid suspension of crystalline or amorphous material with poor water solubility. Amorphous material may be used alone or together with stabilizers as necessary. The rate of absorption of the drug then depends upon its rate of dissolution, which in turn, may depend upon crystal size and crystalline form Alternatively, delayed absorption of a parenterally administered drug form can be accomplished by dissolving or suspending the drug in an oil vehicle.

For intramuscular preparations, a sterile formulation of a compound of the present invention, or a suitable soluble salt form of the compound, for example the hydrochloride salt, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular, or parental formulation of a compound of the present invention may be administered as a bolus or by slow infusion. A bolus is a dose that is administered in less than 30 minutes. In one embodiment, a bolus is administered in less than 15 or less than 10 minutes. In another embodiment, a bolus is administered in less than 5 minutes. In yet another embodiment, a bolus is administered in one minute or less. An infusion is a dose that is administered at a rate of 30 minutes or greater. In one embodiment, the infusion is one hour or greater. In another embodiment, the infusion is substantially constant.

For topical use the pharmaceutical compositions can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the pharmaceutical composition can be presented in liquid or semiliquid form formulated in hydrophobic or hydrophilic bases as ointments, creams, lotions, paints or powders.

For rectal administration, the pharmaceutical compositions can be administered in the form of suppositories admixed with conventional carriers such as cocoa butter, polyethylene glycol or a suppository wax or other glyceride that are solid at room temperature but liquid at body temperature and therefore melt in the rectum or vaginal cavity and release the active compound.

Alternatively, the pharmaceutical compositions can be in powder form for reconstitution in the appropriate pharmaceutically acceptable carrier at the time of delivery. In another embodiment, the unit dosage form of the compound can be a solution of the compound, or a salt thereof, in a suitable diluent in sterile, hermetically sealed ampoules or sterile syringes. The concentration of the compound in the unit dosage may vary, e.g. from about 1 percent to about 50 percent, depending on the compound used and its solubility and the dose desired by the physician. If the compositions contain dosage units, each dosage unit can contain from 1-500 mg of the active material. For adult human treatment, the dosage employed can range from 5 mg to 10 g, per day, depending on the route and frequency of administration.

The pharmaceutical compositions disclosed herein can be placed in a pharmaceutically acceptable carrier and are delivered to a recipient subject (e.g., a human) in accordance with known methods of drug delivery. In general, the methods of delivering the pharmaceutical compositions in vivo utilize art-recognized protocols for delivering the agent with the only substantial procedural modification being the substitution of the compounds of the present invention for the drugs in the art-recognized protocols. Likewise, methods for using the claimed compositions for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the present invention for the drugs in the art-recognized protocols.

Methods of Use

In one embodiment, the invention provides a method for treating an infection in a subject by administering a therapeutically-effective amount of a compound or composition of the invention. In one embodiment, the method comprises administering to a subject in need thereof a pharmaceutical composition comprising at least one of the compounds described herein. In one embodiment, the pharmaceutical composition can comprise any one of the compounds described herein as the sole active compound or in combination with another compound, composition, or biological material.

The terms "treatment," "therapeutic method," and their cognates refer to both therapeutic treatment and prophylactic/preventative measures. Those in need of treatment may include individuals already having a particular medical disease as well as those at risk for the disease (i.e., those who are likely to ultimately acquire the disorder). A therapeutic method results in the prevention or amelioration of symptoms or an otherwise desired biological outcome and may be evaluated by improved clinical signs, delayed onset of disease, reduced/elevated levels of lymphocytes and/or antibodies, etc.

In one embodiment, the pharmaceutical is therapeutically effective in humans while not being not cross resistant with aminoglycosides, β-lactams, and fluoroquinolones.

Exemplary procedures for delivering an antibacterial agent are described in U.S. Pat. No. 5,041,567, and PCT patent application number EP94/02552 (publication no. WO 95/05384), the disclosures of which are incorporated herein by reference in their entirety. As used herein, the phrases "therapeutically effective dose" and "therapeutically-effective amount" refer to an amount of a compound of the present invention that prevents the onset, alleviates the symptoms, stops the progression of a bacterial infection, or results in another desired biological outcome such as, e.g., improved clinical signs or reduced/elevated levels of lymphocytes and/or antibodies. The term "treating" is defined as administering, to a subject, a therapeutically-effective amount of a compound of the invention both to prevent the occurrence of an infection and to control or eliminate an infection. The term "subject," as used herein, refers to a mammal, a plant, a lower animal, or a cell culture. In one embodiment, a subject is a human or other animal patient in need of antibacterial treatment.

The present invention also provides methods of administering a compound disclosed herein or a pharmaceutical composition thereof to a subject in need thereof in an amount that is efficacious in reducing or eliminating the bacterial infection. The pharmaceutical compositions of this invention can be administered to humans and other animals orally, rectally, parenterally, intracisternally, intravaginally, intraperitoneally, topically (as by powders, ointments, or drops), buccally, as an oral or nasal spray, or by an implanted reservoir, external pump or catheter. The compositions may also be administered through the lungs by inhalation. The term "parenteral administration" as used herein, refers to modes of administration, which include intravenous, intramuscular, intraperitoneal, intracisternal, subcutaneous and intraarticular injection and infusion. The compound or composition may be prepared for opthalmic or aerosolized uses.

In one embodiment, the pharmaceutical composition is an antibacterial agent, antibiotic, or antifungal agent.

In one embodiment, the method of the instant invention may be used to treat a subject having a bacterial infection in which the infection is caused or exacerbated by any type of bacteria, such as gram-negative or gram-positive bacteria. In one embodiment, the bacterial infection may be caused or exacerbated by gram-negative bacteria. These gram-negative bacteria include, but are not limited to, *Acinetobacter* spp. (including *Acinetobacter baumannii*), *Citrobacter* spp., *Enterobacter* spp., *Escherichia* spp. (including *Escherichia coli*), *Haemophilus influenzae*, *Morganella morganii*, *Pseudomonas aeruginosa*, *Klebsiella* spp. (including *Klebsiella pneumoniae*), *Salmonella* spp., *Shigella* spp., *Yersinia pseudotuberculosis*, and all species of *Enterobacter, Pasteurella, Brucella, Bordetella, Proteus, Serratia, Providencia*, and *Edwardsiella*.

In one embodiment, the bacterial infection may be caused or exacerbated by gram-positive bacteria. These gram-positive bacteria include, but are not limited to, methicillin-susceptible and methicillin-resistant staphylococci (including *Staphylococcus aureus, S. epidermidis, S. haemolyticus, S. hominis, S. saprophyticus*, and coagulase-negative staphylococci), glycopeptide intermediary-susceptible *S. aureus* (GISA), vancomycin-resistant *Staphylococcus aureus* (VRSA), penicillin-susceptible and penicillin-resistant streptococci (including *Streptococcus pneumoniae, S. pyogenes, S. agalactiae, S. avium, S. bovis, S. lactis, S. sangius* and *Streptococci* Group C, *Streptococci* Group G and viridans streptococci), enterococci (including vancomycin-susceptible and vancomycin-resistant strains such as *Enterococcus faecalis* and *E. faecium*), *Clostridium difficile, C. clostridiiforme, C. innocuum, C. perfringens, C. ramosum, Haemophilus influenzae, Listeria monocytogenes, Corynebacterium jeikeium, Bifidobacterium* spp., *Eubacterium aerofaciens, E. lentum, Lactobacillus acidophilus, L. casei, L. plantarum, Lactococcus* spp., *Leuconostoc* spp., *Pediococcus* spp., *Peptostreptococcus anaerobius, P. asaccarolyticus, P. magnus, P. micros, P. prevotii, P. productus, Propionibacterium acnes, Actinomyces* spp., and *Moraxella* spp. (including *M. catarrhalis*).

In one embodiment, the antibacterial activity of the compounds disclosed herein against classically "resistant" strains is comparable to that against classically "susceptible" strains in in vitro experiments. In one embodiment, a compound according to this invention or a pharmaceutical composition thereof is administered according to the methods of this invention to a patient in need of rapidly acting antibiotic therapy.

The method of the instant invention may be used for any bacterial infection of any organ or tissue in the body. In one embodiment, the bacterial infection is caused by gram-negative bacteria. These organs or tissue include, without limitation, skeletal muscle, skin, bloodstream, kidneys, heart, lung and bone. The method of the invention may be used to treat, without limitation, skin and soft tissue infections, bacteremia and urinary tract infections. The method of the invention may be used to treat community acquired respiratory infections, including, without limitation, otitis media, sinusitis, chronic bronchitis and pneumonia, including pneumonia caused by drug-resistant *S. pneumoniae* or *H. influenzae*. The method of the invention also may be used to treat mixed infections that comprise different types of gram-negative bacteria, or which comprise both gram-positive and gram-negative bacteria. These types of infections include intra-abdominal infections and obstetrical/gynecological infections. The method of the invention also may be used to treat an infection including, without limitation, endocarditis, nephritis, septic arthritis, intra-abdominal sepsis, bone and joint infections and osteomyelitis. In one embodiment, any of the above-described diseases may be treated using compounds according to this invention or pharmaceutical compositions thereof.

The method of the present invention may also be practiced while concurrently administering one or more other antimicrobial agents, such as antibacterial agents (antibiotics) or antifungal agents. In one aspect, the method may be practiced by administering more than one compound according to this invention. In another embodiment, the method may be practiced by administering a compound according to this invention with another peptide compound described herein, or peptide compounds described, for example in International Patent Applications WO 01/44272; WO 01/44274; and WO 01/44271.

Antibacterial agents and classes thereof that may be co-administered with a compound of the present invention include, without limitation, penicillins and related drugs, carbapenems, cephalosporins and related drugs, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, evernimomicin, glycopeptide, glycylcycline, ketolides, oxazolidinone; imipenen, amikacin, netilmicin, fosfomycin, gentamicin, ceftriaxone, ZIRACIN® (56-deacetyl-57-demethyl-45-O-de(2-methyl-1-oxopropyl)-12-O-(2,3,6-trideoxy-3-C-methyl-4-O-methyl-3-nitro-alpha-L-arabino-hexopyranosyl)flambamycin), LY 333328, CL 331002, HMR 3647 ZYVOX® (linezolid), SYNERCID® (dalfopristin-quinupristin), Aztreonam, Metronidazole, Epiroprim, OCA-983, GV-143253, Sanfetrinem sodium, CS-834, Biapenem, A-99058.1, A-165600, A-179796, KA 159, Dynemicin A, DX8739, DU 6681; Cefluprenam, ER 35786, Cefoselis, Sanfetrinem celexetil, HGP-31, Cefpirome, HMR-3647, RU-59863, Mersacidin, KP 736, Rifalazil; Kosan, AM 1732, MEN 10700, Lenapenem, BO 2502A, NE-1530, K130, OPC 20000, OPC 2045, Veneprim, PD 138312, PD 140248, CP 111905, Sulopenem, ritipenam acoxyl, RO-65-5788, Cyclothialidine, Sch-40832, SEP-132613, micacocidin A, SB-275833, SR-15402, SUN A0026, TOC 39, carumonam, Cefozopran, Cefetamet pivoxil, and T 3811.

Antifungal agents that may be co-administered with a compound according to the invention include, without limitation, Caspofungen, Voriconazole, Sertaconazole, IB-367, FK-463, LY-303366, Sch-56592, Sitafloxacin, DB-289, polyenes, such as Amphotericin, Nystatin, Primaricin; azoles, such as Fluconazole, Itraconazole, and Ketoconazole; allylamines, such as Naftifine and Terbinafine; and anti-metabolites such as Flucytosine. Other antifungal agents include without limitation, those disclosed in Fostel et al., *Drug Discovery Today* 5:25-32 (2000), herein incorporated by reference. Fostel et al. discloses antifungal compounds including Corynecandin, Mer-WF3010, Fusacandins, Artrichitin/LL 15G256, Sordarins, Cispentacin, Azoxybacillin, Aureobasidin and Khafrefungin.

The compounds of the present invention can be administered as an aerosol for the treatment of pneumonia or other lung-based infections. In one embodiment, the aerosol delivery vehicle is an anhydrous or dry powder inhaler. The compounds or pharmaceutical compositions thereof may also be directly injected or administered into an abscess, ventricle or joint. Parenteral administration includes subcutaneous, intravenous, intramuscular, intra-articular, intra-synovial, cisternal, intrathecal, intrahepatic, intralesional and intracranial injection or infusion. In another embodiment, the compounds of the present invention are administered intravenously, subcutaneously or orally. In yet another embodiment, the compound or composition is administered to a cell culture, such as by administering in a nutrient medium.

Dosing

Actual dosage levels of active ingredients in the pharmaceutical compositions of this invention may be varied so as to obtain a therapeutically effective amount of the active compounds) to achieve the desired therapeutic response for a particular patient, compositions, and mode of administration. The effective amount can be determined as described herein. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. In one embodiment, the data obtained from the assays can be used in formulating a range of dosage for use in humans.

The method can also comprise administering to the subject an effective dose of a compound of the present invention. An effective dose can range from about 0.1 to about 100 mg/kg of a compound of the invention or a pharmaceutically acceptable salt thereof. In one embodiment, the dose ranges from about 0.1 to about 50 mg/kg of a compound of the invention or a pharmaceutically acceptable salt thereof. In another embodiment, the dose ranges from about 1 to 25 mg/kg of a compound of the invention or a pharmaceutically acceptable salt thereof. An effective dose for cell culture can range from 0.1 to 1000 pg/mL, such as from 0.1 to 200 µg/mL.

Generally dosage levels of about 0.1 µg/kg to about 50 mg/kg, such as a level ranging from about 5 to about 20 mg of active compound per kilogram of body weight per day, can be administered topically, orally or intravenously to a mammalian patient. Other dosage levels range from about 1 µg/kg to about 20 mg/kg, from about 1 µg/kg to about 10 mg/kg, from about 1 µg/kg to about 1 mg/kg, from 10 µg/kg to 1 mg/kg, from 10 µg/kg to 100 µg/kg, from 100 µg to 1 mg/kg, and from about 500 µg/kg to about 5 mg/kg per day. If desired, the effective daily dose may be divided into multiple doses for purposes of administration, e.g., two to four separate doses per day. In one embodiment, the pharmaceutical composition can be administered once per day.

Compositions containing the compounds of the invention can be administered as a single daily dose or in multiple doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the compound and the microorganism or microorganisms involved in the infection.

A compound of the present invention may also be administered in the diet or feed of a patient or animal. If administered as part of a total dietary intake, the amount of compound employed can be less than 1% by weight of the diet, such as no more than 0.5% by weight. The diet for animals can be normal foodstuffs to which the compound can be added or it can be added to a premix.

Other embodiments disclosed herein include:

1. A method for preparing an intermediate for use in the synthesis of a new peptide antibiotic, including the steps of:

(a) Protecting the amino groups of the polymyxin B, colistin, [Ile$^7$]-polymyxin B$_1$, circulin, and an octapeptin with (2-sulfo)-9-fluorenyl methoxy-carbonyl or another acidic derivative of 9-fluorenylmethoxycarbonyl;

(b) Treating the product from the reaction of step (a) with a deacylase to provide a protected peptide intermediate; and (c) Using a modified Edman degradation method or peptidase enzymatic reaction to obtain another protected intermediate by reducing, by one to three amino acids, in the side chain of the protected peptide intermediate; and (d) Purifying the protected peptide intermediate by chromatography.

Another embodiment discloses:

2. A method for producing an antibiotic active against gram-negative and gram-positive bacteria, including strains resistant to clinically used antibiotics, comprising the steps of:

(a) Protecting the amino groups of the polymyxins or other related antibiotics chosen from the group consisting of colistin, [Ile7]-polymyxin B$_1$, circulin, and an octapeptin, with (2-sulfo)-9-fluorenylmethoxycarbonyl or another acidic derivative of 9-fluorenylmethoxycarbonyl;

(b) Treating the product from the reaction of step (a) with a deacylase to provide a protected peptide intermediate;

(c) Using a modified Edman degradation method of peptidase enzymatic reaction to obtain another protected intermediate peptide by reducing in size by one to three amino acids, the exocyclic peptide side chain of the protected peptide.

(d) Chemically modifying the intermediate to produce a protected antibacterial derivative; and (e) Removing the acidic protecting groups to produce the antibiotic.

Another embodiment discloses:

3. An intermediate, which is a chemically protected form of a peptide derived from the polymyxins, [Ile7]-polymyxin B$_1$, octapeptins, colistin, circulins, or related antibiotics and selected from a group consisting of the following, or their corresponding salts:

1) H—(X1) (X2) (X3)-peptide-[(2-sulfo)-9-Fmoc]$_n$

2) H—(X2) (X3)-peptide-[(2-sulfo)-9-Fmoc]$_n$

3) H—(X3)-peptide-[(2-sulfo)-9-Fmoc]$_n$

4) H-peptide-[(2-sulfo)-9-Fmoc]$_3$ wherein for Case 1) H—(X1)(X2)(X3)-peptide-[(2-sulfo) Fmoc]$_n$: H is hydrogen, X1 is L-Dab or another amino acid, X2 is L-Thr or another amino acid, X3 is L-Dab or D-Dab or another amino acid and n=3-6;

for Case 2) H—(X2)(X3)-peptide-[(sulfo)-9-Fmoc]$_n$: H is hydrogen, X2 is L-Thr or another amino acid, X3 is L-Dab or D-Dab or another amino acid, an n=3-5;

for Case 3) H—(X3)-[peptide-[(2-sulfo)-9-Fmoc]$_n$: H is hydrogen, X3 is L-Dab or D-Dab or another amino acid and n=3-4; and for Case 4) H-peptide-[(sulfo)-9-Fmoc]$_n$: H is hydrogen.

Another embodiment discloses:

4. Acidic protected peptide intermediates, derived from the corresponding protected polymyxin B, which can be used to synthesize new peptide antibiotics or their prodrugs where the protecting group is preferably (2-sulfo)-9-Fmoc and the protected peptide intermediates have the structure:

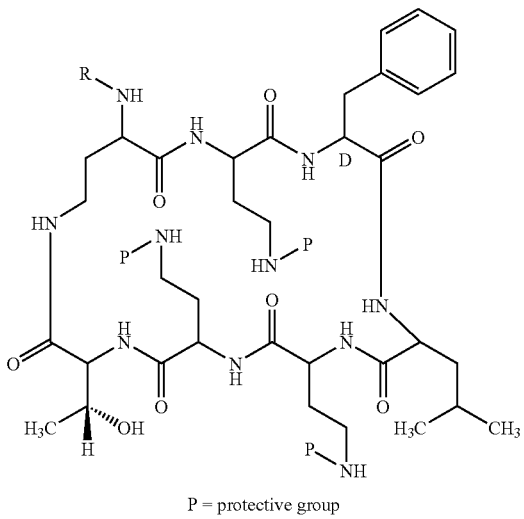

P = protective group protected PBpeptide: R = H

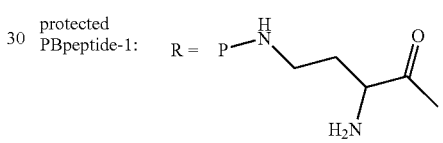

protected PBpeptide-1: R =

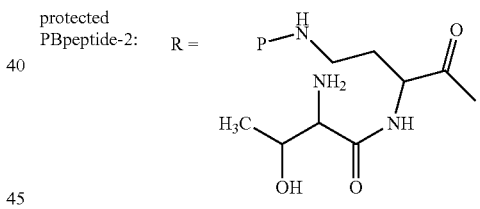

protected PBpeptide-2: R =

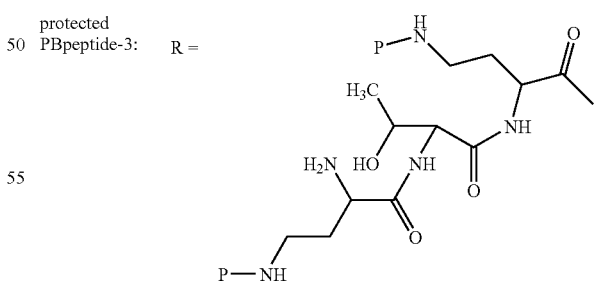

protected PBpeptide-3: R =

Another embodiment discloses:

5. Acidic protected peptide intermediates, derived from the corresponding protected [Ile7]-polymyxin B$_1$, which can be used to synthesize new peptide antibiotics or their prodrugs where the protecting group is preferably (2-sulfo)-9-Fmoc and the protected peptide intermediates have the structure:

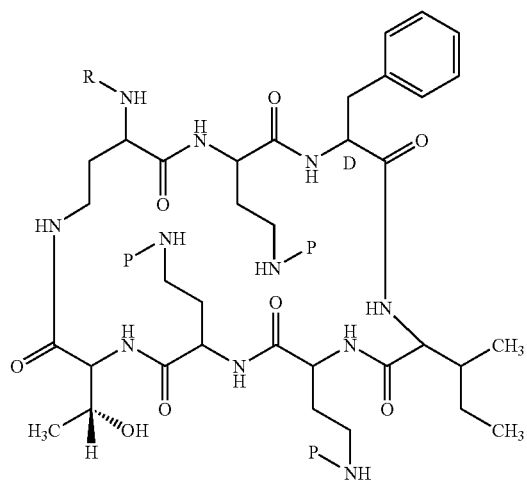

P = protective group protected ILpeptide: R = H

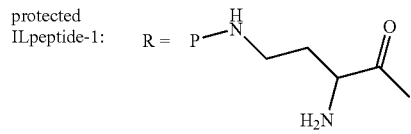

protected ILpeptide-1: R =

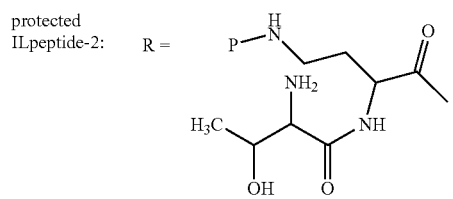

protected ILpeptide-2: R =

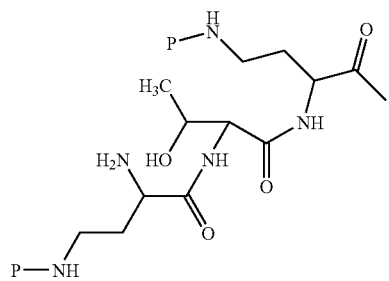

protected ILpeptide-3: R =

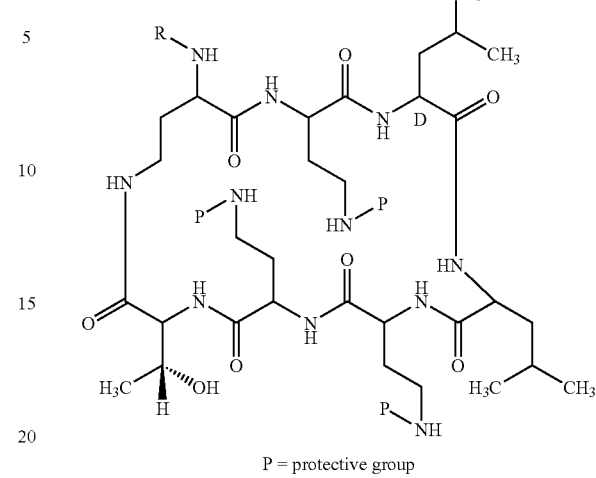

P = protective group protected Cpeptide: R = H

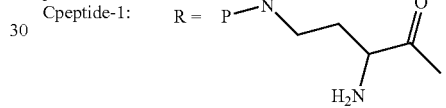

protected Cpeptide-1: R =

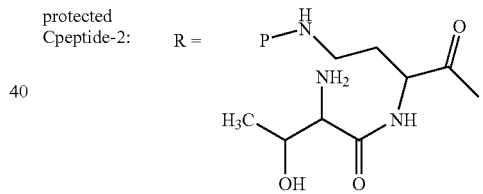

protected Cpeptide-2: R =

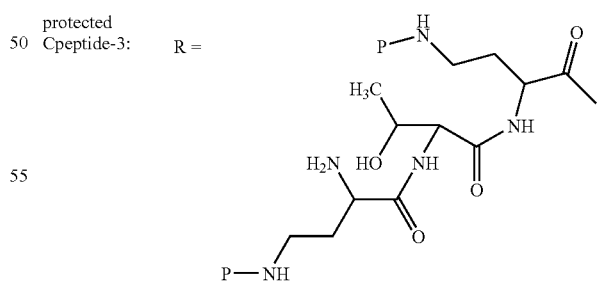

protected Cpeptide-3: R =

Another embodiment discloses:

6. Acidic protected peptide intermediates, derived from the corresponding protected colistin, which can be used to synthesize new peptide antibiotics or their prodrugs where the protecting group is preferably (2-sulfo)-9-Fmoc and the protected peptide intermediates have the structure:

Another embodiment discloses:

7. Acidic protected peptide intermediates, derived from the corresponding protected circulin A, which can be used to synthesize new peptide antibiotics or their prodrugs where the protecting group is preferably (2-sulfo)-9-Fmoc and the protected intermediates have the structure:

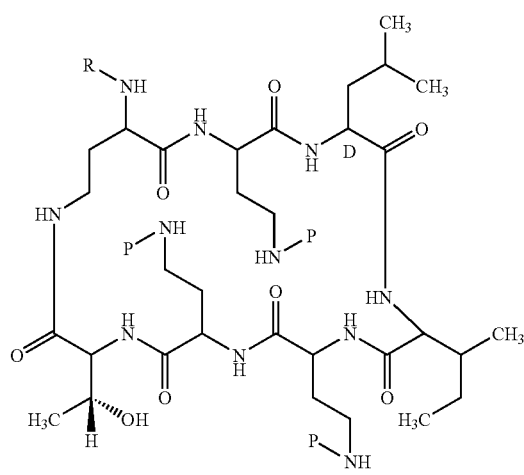

P = protective group protected CApeptide:   R = H protected CApeptide-1:   R = 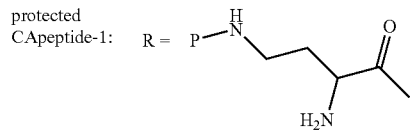

protected CApeptide-2:   R = protected CApeptide-3:   R = 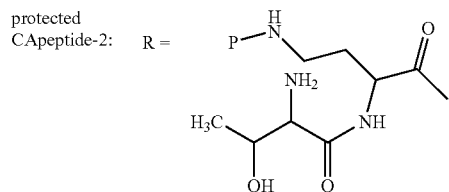

Another embodiment discloses:

8. Acidic protected peptide intermediates, derived from the corresponding protected octapeptin, which can be used to synthesize new peptide antibiotics or their prodrugs where the protecting group is preferably (2-sulfo)-9-Fmoc and the protected peptide intermediates have the structure:

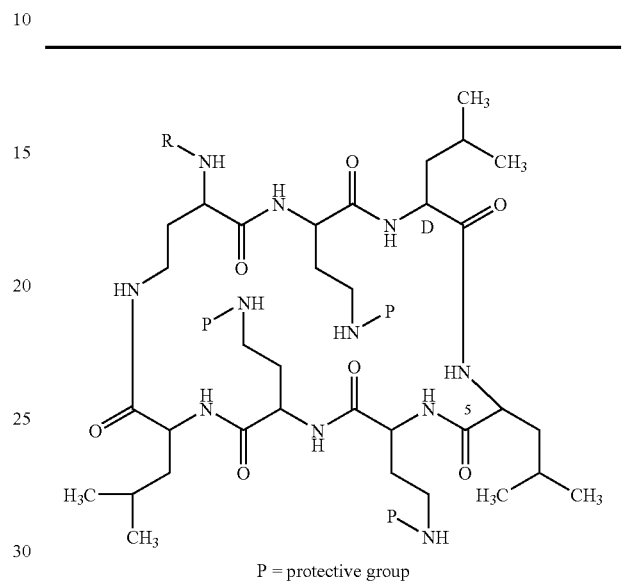

P = protective group protected octapeptin peptide:   R = H protected octapeptin peptide-1:   R = 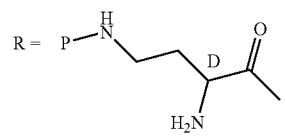

Another embodiment discloses:

9. A protected peptide intermediate, derived from the corresponding octopeptin, wherein another component of the octapeptin antibiotic includes L-phenylalanine instead of L-leucine at the 5-position and wherein the component forms a similar, but alternative, protected peptide intermediate.

Another embodiment discloses:

10. An antibacterial compound or protected compound prepared from a chemically protected form of PBpeptides, Cpeptides or ILpeptides having the following structure where P equals the protective group (2-sulfo)-9-Fmoc or hydrogen:

TABLE 3
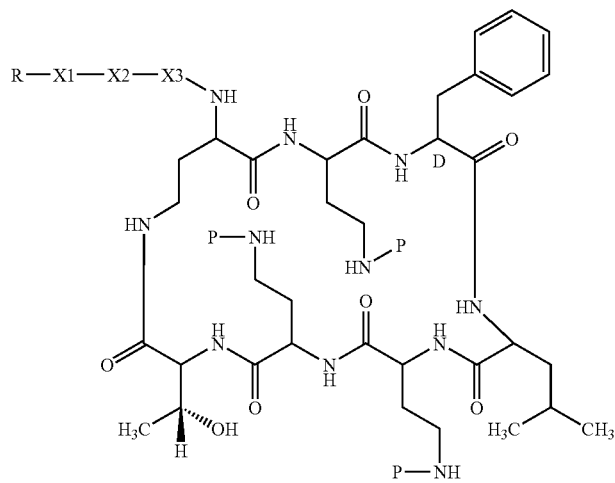
PBpeptide derivatives
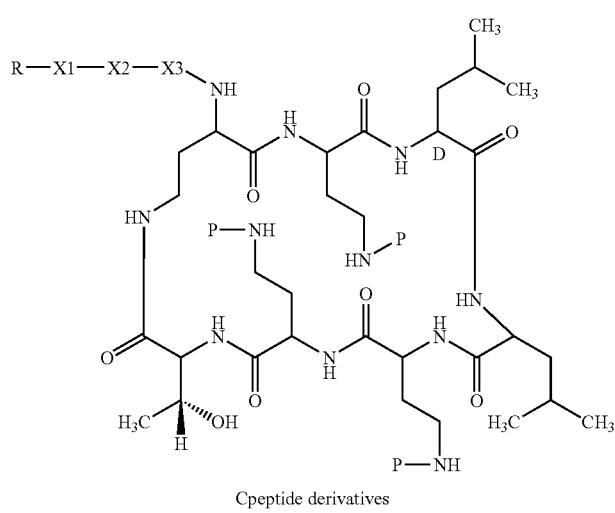
Cpeptide derivatives
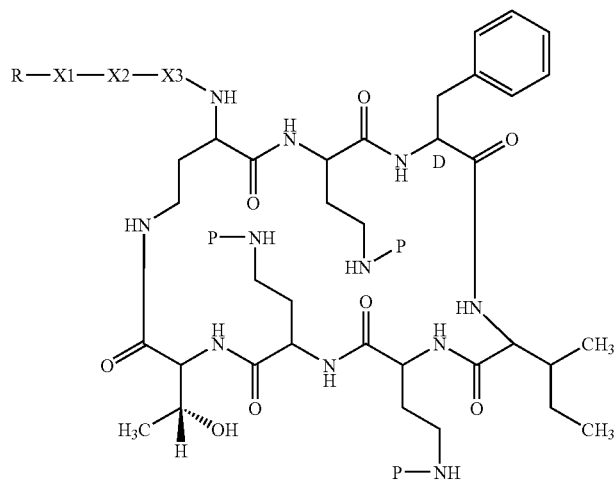
ILpeptide derivatives
| Compound | R | Peptide | X1* | X2 | X3* | P |
|---|---|---|---|---|---|---|
| (P)₅Polymyxin B | $C_8H_{17}CO-$ | PBpeptide | Dab-P | Thr | Dab-P | $HSO_3$-Fmoc- |
| 1 | n-$C_9H_{19}CO-$ | PBpeptide | Dab | Thr | Dab | H |
| 1P | n-$C_9H_{19}CO-$ | PBpeptide | Dab-P | Thr | Dab-P | $HSO_3$-Fmoc- |

TABLE 3-continued

| | | | | | | |
|---|---|---|---|---|---|---|
| 2 | n-C$_9$H$_{19}$CO-PAPA-** | PBpeptide | Dab | Thr | Dab | H |
| 2P | n-C$_9$H$_{19}$CO-PAPA-** | PBpeptide | Dab-P | Thr | Dab-P | HSO$_3$-Fmoc- |
| 3 | n-C$_8$H$_{17}$NHCO— | PBpeptide | Dab | Thr | Dab | H |
| 3P | n-C$_8$H$_{17}$NHCO— | PBpeptide | Dab-P | Thr | Dab-P | HSO$_3$-Fmoc- |
| 4 | phenyl-NHCS— | PBpeptide | Dab | Thr | Dab | H |
| 4P | phenyl-NHCS— | PBpeptide | Dab-P | Thr | Dab-P | HSO$_3$-Fmoc- |
| 5 | phenyl-NHCO— | PBpeptide | Dab | Thr | Dab | H |
| 5P | phenyl-NHCO— | PBpeptide | Dab-P | Thr | Dab-P | HSO$_3$-Fmoc- |
| 6 | phenyl-CO— | PBpeptide | Dab | Thr | Dab | H |
| 6P | phenyl-CO— | PBpeptide | Dab-P | Thr | Dab-P | HSO$_3$-Fmoc- |
| 7 | 2-naphthyl-OCH$_2$—CO— | PBpeptide | Dab | Thr | Dab | H |
| 7P | 2-naphthyl-OCH$_2$—CO— | PBpeptide | Dab-P | Thr | Dab-P | HSO$_3$-Fmoc- |
| 8 | 4-CH$_5$—C$_6$H$_4$—SO$_2$— | PBpeptide | Dab | Thr | Dab | H |
| 8P | 4-CH$_3$—C$_6$H$_4$—SO$_2$— | PBpeptide | Dab-P | Thr | Dab-P | HSO$_3$-Fmoc- |
| 9 | n-C$_8$H$_{17}$NHCO— | PBpeptide | — | Thr | Dab | H |
| 9P | n-C$_8$H$_{17}$NHCO— | PBpeptide | — | Thr | Dab-P | HSO$_3$-Fmoc- |
| 10 | n-C$_{10}$H$_{21}$SO$_2$— | PBpeptide | Gly | Thr | Dab | H |
| 10P | n-C$_{10}$H$_{21}$SO$_2$— | PBpeptide | Gly | Thr | Dab-P | HSO$_3$-Fmoc |
| 11 | n-C$_9$H$_{19}$CO— | PBpeptide | Lys | The | Dab | H |
| 11p | n-C$_9$H$_{19}$CO— | PBpeptide | Lys-P | Thr | Dab-P | HSO$_3$-Fmoc- |
| 12 | n-C$_9$H$_{19}$CO— | PBpeptide | Phe | Thr | Dab | H |
| 12P | n-C$_9$H$_{19}$CO— | PBpeptide | Phe | Thr | Dab-P | HSO$_3$-Fmoc- |
| 13 | iso-nicotinoyl- | PBpeptide | Dab | Thr | Dab | H |
| 13P | iso-nicotinoyl- | PBpeptide | Dab-P | Thr | Dab-P | HSO$_3$-Fmoc- |
| 14 | 3-indolylethylNHCO— | PBpeptide | Dab | Thr | Dab | H |
| 14P | 3-indolylethylNHCO— | PBpeptide | Dab-P | Thr | Dab-P | HSO$_3$-Fmoc- |
| 15 | N-Acetyl-PAPA- | PBpeptide | Dab | Thr | Dab | H |
| 15P | N-Acetyl-PAPA- | PBpeptide | Dab-P | Thr | Dab-P | HSO$_3$-Fmoc- |
| 16 | n-C$_9$H$_{19}$CO-Phe- | PBpeptide | Dab | Thr | Dab | H |
| 16P | n-C$_9$H$_{19}$CO-Phe- | PBpeptide | Dab-P | Thr | Dab-P | HSO$_3$-Fmoc- |
| 17 | p-(n-C$_{10}$H$_{21}$)-Phenyl-NHCO— | PBpeptide | Dab | Thr | Dab | H |
| 17P | p-(n-C$_{10}$H$_{21}$)-Phenyl-NHCO— | PBpeptide | Dab-P | Thr | Dab-P | HSO$_3$-Fmoc- |
| 18 | 4-biphenylNHCO— | PBpeptide | Dab | Thr | Dab | H |
| 18P | 4-biphenylNHCO— | PBpeptide | Dab-P | Thr | Dab-P | HSO$_3$-Fmoc- |
| 19 | C$_6$H$_5$CH$_2$OCH$_2$CO— | PBpeptide | Dab | Thr | Dab | H |
| 19P | C$_6$H$_5$CH$_2$OCH$_2$CO— | PBpeptide | Dab-P | Thr | Dab-P | HSO$_3$-Fmoc- |
| 20 | 4-(C$_6$H$_5$O)C$_6$H$_4$NHCO— | PBpeptide | Dab | Thr | Dab | H |
| 20P | 4-(C$_6$H$_5$O)C$_6$H$_4$NHCO— | PBpeptide | Dab-P | Thr | Dab-P | HSO$_3$-Fmoc- |
| 21 | 4-Cl-C$_6$H$_4$-NHCO— | PBpeptide | Dab | Thr | Dab | H |
| 21P | 4-Cl-C$_6$H$_4$-NHCO— | PBpeptide | Dab-P | Thr | Dab-P | HSO$_3$-Fmoc- |
| 22 | benzyl-NHCO— | PBpeptide | Dab | Thr | Dab | H |
| 22P | benzyl-NHCO— | PBpeptide | Dab-P | Thr | Dab-P | HSO$_3$-Fmoc- |
| 23 | cyclothexyl-NHCO— | PBpeptide | Dab | Thr | Dab | H |
| 23P | cyclothexyl-NHCO— | PBpeptide | Dab-P | Thr | Dab-P | HSO$_3$-Fmoc- |
| 24 | phenyl-NHCS— | PBpeptide | — | Thr | Dab | H |
| 24P | phenyl-NHCS— | PBpeptide | — | Thr | Dab-P | HSO$_3$-Fmoc- |
| 25 | n-C$_9$H$_{19}$CO— | PBpeptide | — | — | Dab | H |
| 25P | n-C$_9$H$_{19}$CO— | PBpeptide | — | — | Dab-P | HSO$_3$-Fmoc- |
| 26 | n-C$_9$H$_{19}$CO— | ILpeptide | Dab | Thr | Dab | H |
| 26P | n-C$_9$H$_{19}$CO— | ILpeptide | Dab-P | Thr | Dab-P | HSO$_3$-Fmoc- |
| 27 | n-C$_9$H$_{19}$CO-PAPA-** | ILpeptide | Dab | Thr | Dab | H |
| 27P | n-C$_9$H$_{19}$CO-PAPA-** | ILpeptide | Dab-P | Thr | Dab-P | HSO$_3$-Fmoc- |
| 28 | n-C$_8$H$_{17}$NHCO— | ILpeptide | Dab | Thr | Dab | H |
| 28P | n-C$_8$H$_{17}$NHCO— | ILpeptide | Dab-P | Thr | Dab-P | HSO$_3$-Fmoc- |
| 29 | phenyl-NHCS— | ILpeptide | Dab | Thr | Dab | H |
| 29P | phenyl-NHCS— | ILpeptide | Dab-P | Thr | Dab-P | HSO$_3$-Fmoc- |
| 30 | phenyl-NHCO— | ILpeptide | Dab | Thr | Dab | H |
| 30P | phenyl-NHCO— | ILpeptide | Dab-P | Thr | Dab-P | HSO$_3$-Fmoc- |
| 31 | phenyl-CO— | ILpeptide | Dab | Thr | Dab | H |
| 31P | phenyl-CO— | ILpeptide | Dab-P | Thr | Dab-P | HSO$_3$-Fmoc- |
| 32 | 2—naphthyl-OCH$_2$—CO— | ILpeptide | Dab | Thr | Dab | H |
| 32P | 2—naphthyl-OCH$_2$—CO— | ILpeptide | Dab-P | Thr | Dab-P | HSO$_3$-Fmoc- |
| 33 | 4-CH$_3$—C$_6$H$_4$—SO$_2$— | ILpeptide | Dab | Thr | Dab | H |
| 33P | 4-CH$_3$—C$_6$H$_4$—SO$_2$— | ILpeptide | Dab-P | Thr | Dab-P | HSO$_3$-Fmoc- |
| 34 | n-C$_8$H$_{17}$NHCO— | ILpeptide | — | Thr | Dab | H |
| 34P | n-C$_8$H$_{17}$NHCO— | ILpeptide | — | Thr | Dab-P | HSO$_3$-Fmoc- |
| 35 | n-C$_{10}$H$_{21}$SO$_2$— | ILpeptide | Gly | Thr | Dab | H |
| 35P | n-C$_{10}$H$_{21}$SO$_2$— | ILpeptide | Gly | Thr | Dab-P | HSO$_3$-Fmoc- |
| 36 | n-C$_9$H$_{19}$CO— | ILpeptide | Lys | Thr | Dab | H |
| 36P | n-C$_9$H$_{19}$CO— | ILpeptide | Lys-P | Thr | Dab-P | HSO$_3$-Fmoc- |
| 37 | n-C$_9$H$_{19}$CO— | ILpeptide | Phe | Thr | Dab | H |
| 37P | n-C$_9$H$_{19}$CO— | ILpeptide | Phe | Thr | Dab-P | HSO$_3$-Fmoc- |
| 38 | iso-nicotinoyl- | ILpeptide | Dab | Thr | Dab | H |
| 38P | iso-nicotinoyl- | ILpeptide | Dab-P | Thr | Dab-P | HSO$_3$-Fmoc- |
| 39 | 3-indolylethylNHCO— | ILpeptide | Dab | Thr | Dab | H |
| 39P | 3-indolylethylNHCO— | ILpeptide | Dab | Thr | Dab | HSO$_3$-Fmoc- |
| 40 | N-Acetyl-PAPA- | ILpeptide | Dab | Thr | Dab | H |
| 40P | N-Acetyt-PAPA- | ILpeptide | Dab-P | Thr | Dab-P | HSO$_3$-Fmoc- |
| 41 | n-C$_9$H$_{19}$CO-Phe- | ILpeptide | Dab | Thr | Dab | H |
| 41P | n-C$_9$H$_{19}$CO-Phe- | ILpeptide | Dab-P | Thr | Dab-P | HSO$_3$-Fmoc- |

TABLE 3-continued

| | | | | | |
|---|---|---|---|---|---|
| 42 | p-(n-$C_{10}H_{21}$)-Phenyl-NHCO— | ILpeptide | Dab | Thr | Dab | H |
| 42P | p-(n-$C_{10}H_{21}$)-Phenyl-NHCO— | ILpeptide | Dab-P | Thr | Dab-P | $HSO_3$-Fmoc- |
| 43 | 4-biphenylNHCO— | ILpeptide | Dab | Thr | Dab | H |
| 43P | 4-biphenylNHCO— | ILpeptide | Dab-P | Thr | Dab-P | $HSO_3$-Fmoc- |
| 44 | $C_6H_5CH_2OCH_2CO$— | ILpeptide | Dab | Thr | Dab | H |
| 44P | $C_6H_5CH_2OCH_2CO$— | ILpeptide | Dab-P | Thr | Dab-P | $HSO_3$-Fmoc- |
| 45 | 4-($C_6H_5O)C_6H_4$NHCO— | ILpeptide | Dab | Thr | Dab | H |
| 45P | 4-($C_6H_5O)C_6H_4$NHCO— | ILpeptide | Dab-P | Thr | Dab-P | $HSO_3$-Fmoc- |
| 46 | 4-Cl-$C_6H_4$—NHCO— | ILpeptide | Dab | Thr | Dab | H |
| 46P | 4-Cl-$C_6H_4$—NHCO— | ILpeptide | Dab | Thr | Dab | $HSO_3$-Fmoc- |
| 47 | benzyl-NHCO— | ILpeptide | Dab | Thr | Dab | H |
| 47P | benzyl-NHCO— | ILpeptide | Dab-P | Thr | Dab-P | $HSO_3$-Fmoc- |
| 48 | cyclohexyl-NHCO— | ILpeptide | Dab | Thr | Dab | H |
| 48P | cyclohexyl-NHCO— | ILpeptide | Dab-P | Thr | Dab-P | $HSO_3$-Fmoc- |
| 49 | phenyl-NHCS— | ILpeptide | — | Thr | Dab | H |
| 49P | phenyl-NHCS— | ILpeptide | — | Thr | Dab-P | $HSO_3$-Fmoc- |
| 50 | n-$C_9H_{19}$CO— | ILpeptide | — | — | Dab | H |
| 50P | n-$C_9H_{19}$CO— | ILpeptide | — | — | Dab-P | $HSO_3$-Fmoc- |
| 51 | n-$C_8H_{17}$NHCO— | Cpeptide | Dab | Thr | Dab | H |
| 51P | n-$C_8H_{17}$NHCO— | Cpeptide | Dab-P | Thr | Dab-P | $HSO_3$-Fmoc- |
| 52 | n-$C_9H_{19}$CO-Phe- | Cpeptide | Dab | Thr | Dab | H |
| 52P | n-$C_9H_{19}$CO-Phe- | Cpeptide | Dab-P | Thr | Dab-P | $HSO_3$-Fmoc- |
| 53 | 4-$CH_3$—$C_6H_4$—$SO_2$— | Cpeptide | Dab | Thr | Dab | H |
| 53-P | 4-$CH_3$—$C_6H_4$—$SO_2$— | Cpeptide | Dab-P | Thr | Dab-P | $HSO_3$-Fmoc- |
| 54 | n-$CH_9H_{19}$CO-Lys | PBpeptide | Dab | Thr | Dab | H |
| 54P | n-$CH_9H_{19}$CO-Lys | PBpeptide | Dab-P | Thr | Dab-P | $HSO_3$-Fmoc- |

*Dab-P is 4-N-($HSO_3$-Fmoc)-diaminobutyryl, Lys-P is 6-N-($HSO_3$-Fmoc)-lysyl
**PAPA is p-aminophenylacetyl
All amino acids are the L-isomers unless indicated otherwise.

Another embodiment discloses:

11. An antibiotic prepared from an intermediate, which is a chemically protected form of a peptide derived from the polymyxins, octapeptins, colistin, [Ile⁷]polymyxin $B_1$, said antibiotic selected from a group consisting of the following, or their corresponding salts:

| | |
|---|---|
| Case 1 | A-(X1) (X2) (X3) - Peptide |
| Case 2 | A-(X2) (X3) - Peptide |
| Case 3 | A-(X3) - Peptide |
| Case 4 | A-Peptide | wherein for Case 1) A-(X1) (X2) (X3)-Peptide: A=R'—(C=O)—, R'—$SO_2$—, R'—(C=NH)—, R'—NH—(C=S)—, R'—NH—(C=O)—, where R' is alkyl, cycloalkyl, alkenyl, aryl, heteroaryl, or heterocyclyl and X1 is L-Dab or another amino acid, X2 is L-Thr or another amino acid, and X3 is L-Dab or another amino acid;

for Case 2) A-(X2)(X3)-Peptide: "A" is the same as described for Case 1, X2 is L-Thr or another amino acid and X3 is L-Dab or another amino acid;

for Case 3) A-(X3)-peptide: "A" is the same as described in Case 1 and X3 is L-Dab or another amino acid;

for Case 4) A-peptide: "A" is the same as described for Case 1.

Another embodiment discloses:

12. Peptide antibiotics having the following structure and minimum inhibitory concentrations for use against gram-negative and gram-positive bacteria:

TABLE 4

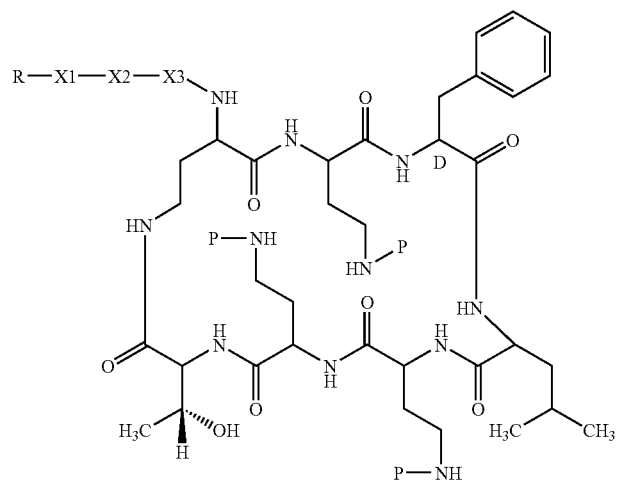

PBpeptide derivatives

TABLE 4-continued

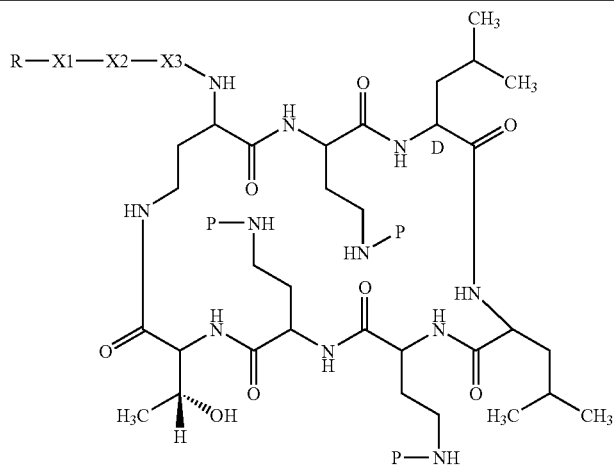

Cpeptide derivatives

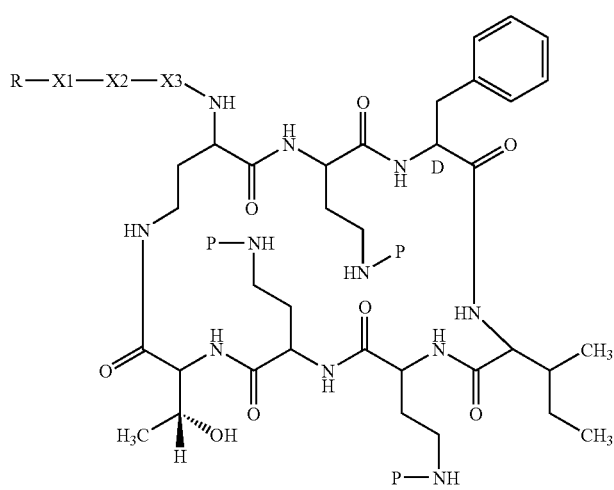

ILpeptide derivatives

| Compound | R | X1* | X2 | X3* | cyclic peptide | E. coli MIC* | Staph MIC* | Pseudo MIC* |
|---|---|---|---|---|---|---|---|---|
| Polymyxin B | C$_8$H$_{17}$CO— | Dab | Thr | Dab | PB | 0.6 | >10 | 0.6 |
| Polymyxin B$_1$ | C$_8$H$_{17}$CO— | Dab | Thr | Dab | PB | 0.6 | 10 | 0.6 |
| [Ile$^7$]-polymyxin B$_1$ | C$_8$H$_{17}$CO— | Dab | Thr | Dab | IL | 0.6 | 20 | 1.25 |
| Colistin | C$_8$H$_{17}$CO— | Dab | Thr | Dab | C | 0.6 | >20 | 0.6 |
| 1 | n-C$_9$H$_{19}$CO— | Dab | Thr | Dab | PB | 0.6 | | |
| 2 | n-C$_{10}$H$_{21}$CO-PAPA-** | Dab | Thr | Dab | PB | 1.25 | 2.5 | 1.25 |
| 3 | n-C$_8$H$_{17}$NHCO— | Dab | Thr | Dab | PB | 1.25 | 10 | 0.6 |
| 4 | phenyl-NHCS— | Dab | Thr | Dab | PB | 0.6 | >10 | 0.6 |
| 5 | phenyl-NHCO— | Dab | Thr | Dab | PB | 0.6 | >10 | 1.25 |
| 6 | phenyl-CO— | Dab | Thr | Dab | PB | 1.25 | >10 | 0.6 |
| 7 | 2-naphthyl-OCH$_2$—CO— | Dab | Thr | Dab | PB | 1.25 | >10 | 0.6 |
| 8 | 4-CH$_3$—C$_6$H$_4$—SO$_2$— | Dab | Thr | Dab | PB | 1.25 | >20 | 0.6 |
| 9 | n-C$_8$H$_{17}$NHCO— | — | Thr | Dab | PB | 2.5 | >10 | 1.25 |
| 10 | n-C$_{10}$H$_{21}$SO$_2$— | Gly | Thr | Dab | PB | 2.5 | 5 | 2.5 |
| 11 | n-C$_9$H$_{19}$CO— | Lys | Thr | Dab | PB | 2.5 | 10 | 1.25 |
| 12 | n-C$_9$H$_{19}$CO— | Phe | Thr | Dab | PB | 2.5 | 2.5 | 2.5 |
| 13 | iso-nicotinoyl- | Dab | Thr | Dab | PB | 5.0 | >20 | 1.25 |
| 14 | 3-indolylethylNHCO— | Dab | Thr | Dab | PB | 2.5 | >20 | 1.25 |
| 15 | N-Acetyl-PAPA- | Dab | Thr | Dab | PB | 2.5 | >20 | 2.5 |
| 16 | n-C$_9$H$_{19}$CO-Phe- | Dab | Thr | Dab | PB | 1.25 | 2.5 | 0.6 |
| 17 | 4-n-C$_{10}$H$_{21}$-Phenyl-NHCO— | Dab | Thr | Dab | PB | 5.0 | 2.5 | 2.5 |
| 18 | 4-biphenylNHCO— | Dab | Thr | Dab | PB | 2.5 | 2.5 | 1.2 |
| 19 | C$_6$H$_5$CH$_2$OCH$_2$—CO— | Dab | Thr | Dab | PB | 0.6 | >20 | 1.25 |
| 20 | 4-(C$_6$H$_5$O)C$_6$H$_4$NHCO— | Dab | Thr | Dab | PB | 0.6 | 5.0 | 1.25 |
| 21 | 4-Cl-C$_6$H$_4$—NHCO— | Dab | Thr | Dab | PB | 0.6 | 20 | 0.6 |
| 22 | benzyl-NHCO— | Dab | Thr | Dab | PB | 1.25 | >20 | 0.6 |
| 23 | cyclohexyl-NHCO— | Dab | Thr | Dab | PB | 0.6 | >20 | 0.6 |

TABLE 4-continued

| | | | | | | | | |
|---|---|---|---|---|---|---|---|---|
| 24 | phenyl-NHCS— | — | Thr | Dab | PB | >5.0 | >20 | 5.0 |
| 25 | n-$C_9H_{19}$CO— | — | — | Dab | PB | >5.0 | 10 | 1.25 |
| 48 | cyclohexyl-NHCO— | Dab | Thr | Dab | IL | 0.6 | | 0.6 |
| 51 | n-$C_9H_{17}$NHCO— | Dab | Thr | Dab | C | 1.25 | 20 | 0.6 |
| 52 | n-$C_9H_{19}$CO-Phe- | Dab | Thr | Dab | C | 1.25 | 2.5 | 2.5 |
| 53 | 4-$CH_3$—$C_6H_4$—$SO_2$— | Dab | Thr | Dab | C | 1.25 | >20 | 0.6 |
| 54 | n-$C_9H_{19}$CO-Lys- | Dab | Thr | Dab | PB | 0.6 | 2.5 | 0.6 |

*MIC values were determined by serial twofold broth dilution method using *Escherichia coli*, ATCC #26, *Staphylococcus aureus* Smith, and *Pseudomonas aeruginosa*, ATCC 27853, as assay organisms which were grown in Mueller Hinton broth.
**PAPA = p-aminophenylacetyl Another embodiment discloses:

A process for preparing a water-soluble, stable, solid form of a deacylase enzyme including the steps of:

(a) Fermenting a strain of *Actinoplanes utahensis* to obtain cells of the organism.

(b) Washing the cells with water to remove impurities.

(c) Extracting the washed cells with an aqueous base, pH 8-11.

(d) Adjusting the extract to pH 7-8 and freeze drying the solution to obtain the solid form of the enzyme.

Another embodiment discloses:

14. The process further comprises step (e):

(e) thereafter, further purifying said enzyme by use of chromatography.

A series of new antibiotics is represented by the sulfonyl derivatives (Table 3, compounds 8 and 10). The side chains from these compounds are not attached to the PBpeptides by an acyl group but instead by a sulfonyl group. Other linkers such as ureas or thioureas have been made and resulted in compounds with good bacterial activity. Potent activity was also shown with aromatic acyl exocyclic chains and aromatic groups linked through urea and thiourea linkages (compounds 4 and 5) as shown in Table 3.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

EXAMPLES

The polymyxin $B_1$ and the [$Ile^7$]-polymyxin $B_1$ (Table 3) were isolated from the polymyxin B complex. The new peptides derived from ILpeptide-3 could be prepared by purifying [$Ile^7$]-polymyxin $B_1$ from the polymyxin B complex and protecting this peptide, deacylating this protected product, adding back a new side chain and deprotecting. An alternative procedure involved protecting the polymyxin B complex, deacylating to obtain the protected PBpeptide-3 and ILpeptide-3 mixture, adding the new side chain, deprotecting, and then resolving the mixture to obtain new derivatives of both peptides. A summary of HPLC retention times observed for the new peptides derived from the PBpeptide and ILpeptide is given in Table 5.

TABLE 5

| Compound Numbers | Isocratic system % Acetonitrile | Respective Retention Times (minutes) |
|---|---|---|
| Polymyxin $B_1$, IL variant | 58 | 4.79, 4.16 |
| 1, 26 | 60 | 5.45, 4.85 |
| 2, 27 | 48 | 4.52, 4.20 |
| 3, 28 | 55 | 4.04, 3.64 |
| 4, 29 | 65 | 4.39, 3.75 |
| 5, 30 | 64 | 3.34, 2.94 |
| 6, 31 | 65 | 3.61, 3.16 |
| 7, 32 | 60 | 4.10, 3.64 |
| 8, 33 | 64 | 3.91, 3.40 |

TABLE 5-continued

| Compound Numbers | Isocratic system % Acetonitrile | Respective Retention Times (minutes) |
|---|---|---|
| 9, 34 | 53 | 4.80, 429 |
| 10, 35 | 60 | 4.23, 3.92 |
| 11, 36 | 54 | 3.89, 3.55 |
| 12, 37 | 60 | 6.23, 5.93 |
| 13, 38 | 70 | 3.88, 3.37 |
| 14, 39 | 64 | 5.52, 4.65 |
| 15, 40 | 68 | 4.15, 3.56 |
| 16, 41 | 48 | 5.38, 4.97 |
| 17, 42 | 43 | 5.74, 5.35 |
| 18, 43 | 58 | 4.79, 4.21 |
| 19, 44 | 64 | 4.34, 3.74 |
| 20, 45 | 57 | 4.14, 3.70 |
| 21, 46 | 62 | 4.64, 3.98 |
| 22, 47 | 65 | 4.08, 3.52 |
| 23, 48 | 65 | 5.03, 4.25 |
| 24, 49 | 60 | 3.68, 3.23 |
| 25, 50 | 53 | 3.80, 3.47 |

*HPLC analyses were performed using a reverse phase C8 column. Isocratic eluents were prepared from various ratios of Eluent B and Eluent C to give the % acetonitrile listed.
Eluent B: 0.05M $(NH_4)_2SO_4$ + 0.005M $H_2SO_4$ pH~2.44
Eluent C: 85% acetonitrile and 15% water Analysis by HPLC of peptides protected with at least one (2-Sulfo)-9-fluorenylmethoxycarbonyl group can be performed using a reverse phase C8 column using a gradient of 35% to 75% MeCN/0.2M $(NH_4)_3PO_4$ at pH 7.2. Analysis by HPLC of deprotected peptides can be performed using the conditions given in Table Unless otherwise noted, N-hydroxysuccinimide reagents were prepared according to the methods disclosed in Gershonov, E., Goldwaser, I., Fridkin, M., Schecter, Y, 2000, "A Novel Approach for a Water-Soluble Long-Acting Insulin Proprug: Design, Preparation, and Analysis of [(2-Sulfo)-9-Fluorenylmethoxycarbonyl]$_3$-Insulin," Journal of Medicinal Chemistry 43: (13), 2530-2537, and Schechter, Y. Tsudbery, H., Fridkin, M., 2002, N-[(2-Sulfo)-9-Fluorenylmethoxycarbonyl]$_3$-Gentamicin Is a Long-Acting Prodrug Derivative," Journal of Medicinal Chemistry 45: (19), 4264-4270.

Example 1

N-[(2-Sulfo)-9-fluorenylmethoxycarbonyl)]$_5$-polymyxin B

Polymyxin B sulfate (1.0 g., 0.841 mmol) was dissolved in a solution of 25 mL, saturated sodium bicarbonate, 25 mL of water, and 25 mL of tetrahydrofuran. Polymyxin B sulfate is commercially available, e.g., from Sigma (Milwaukee, Wis.). A solution of (2-sulfo)-9-fluorenylmethoxy-N-hydroxysuccinimide (2.0 g., 4.8 mmol) in 25 mL of tetrahydrofuran was added in several portions over 45 min. The reaction mixture was stirred at room temperature over night and diluted with 50 mL of water, then acidified with 25 mL of 6 N hydrochloric acid to give an oily precipitate. The mixture was chilled and the aqueous layer was decanted and the oily residue was dissolved in 100 mL of ethanol. The ethanol was evaporated under vacuum (35° C.) and the resulting solid was triturated with ethyl acetate, filtered and dried to afford 1.74 g. of product. HPLC with a gradient on a reverse phase C8 column showed a single peak, N-[2-(sulfo)-9-fluorenylmethoxycarbonyl)]$_5$-polymyxin B, $C_{131}H_{150}N_{16}O_{38}S_5$, when the column eluent was monitored at 215 nm. ESIMS: calc. m/z for $C_{131}H_{152}N_{16}O_{38}S_5$, $(M+2H)^{+2}$=1358.4. Found 1358.5

The above procedure can be used with polymyxin free base and 2(sulfo)-9-fluorenylmethoxycarbonyl chloride with similar results.

Example 2

Preparation of the Deacylase

The deacylase is produced by culturing Actinoplanes utahensis NRRL 12052 under submerged aerobic fermentation conditions. The fermentation protocol employed is known (Boeck, L. D. et al., Journal of Antibiotics 41:(8), 1085-1092). A stock culture of the NRRL 12052 variant, preserved in 20% glycerol at −70° C., was introduced into a 25×150 mm test tube with a glass rod and Morton closure containing 10 mL of a medium composed of sucrose 2.0%, pre-cooked oatmeal 2.0%, distiller's grains and solubles 0.5%, yeast extract 0.25%, $K_2HPO_4$ 0.1%, KCl 0.05%, $MgSO_4.7H_2O$ 0.05% and $FeSO_4.7H_2O$ 0.0002% in deionized water. After incubation at 30° C. for 72 hrs on a rotary shaker orbiting at 250 rpm the resulting mycelial suspension was transferred into 50 mL of PM3 medium in a 250-mL Erlenmeyer flask. This medium contained sucrose 2.0%, peanut meal 1.0%, $K_2HPO_4$ 0.12%, $KH_2PO_4$ 0.05% and $MgSO_4.7H_2O$ 0.025% in tap water. The flask was incubated at a temperature of 30° C. for a period of 60 to 90 hrs. The harvest time was determined by an assay which involved HPLC analyses of the deacylation of (2-Sulfo-9-fluorenlymethoxycarbonyl)]$_5$ polymyxin B by the whole broth at different times during the fermentation.

Because single-colony isolates from a lyophile of the culture were heterogeneous for both morphology and enzyme production capability, selections were made to recover a stable, high-producing variant. Initially, multiple fermentations were carried out using inocula prepared from strain 12052. Vegetative growth from the flask yielding the best deacylating activity was plated on a differential agar (CM). CM agar contained corn steep liquor 0.5%, Bacto peptone 0.5%, soluble starch 1.0%, NaCl 0.05%, $CaCl_2.2H_2O$ 0.05% and Bacto agar 2.0%. Colonies were then selected for further evaluation. Isolate No. 18 was selected as a small colony type and shown to be the best deacylase producer of all colonies selected. Comparison was based on conversion of protected polymyxin B to deacylated protected polymyxin B as determined by HPLC. This isolate was routinely used for the production of the deacylase enzyme.

Example 3

Deacylation of the Protected Polymyxin B by the Enzyme in Cells

Precipitation Method: Cells from 450 mL of deacylase enzyme from the original fermentation according to Example 2 were washed 3× with water, then brought back to original volume with 0.02 M ammonium phosphate buffer and adjusted to pH 8.0. N-[(2-Sulfo)-9-fluorenylmethoxycarbonyl)]$_5$-polymyxin B, 897 mg, was added and the mixture was placed on a shaker at 174 rpm and maintained at 30° C. After five hours the mixture was separated by centrifugation. The clear decant was adjusted to pH 2.3 with 1 N HCl solution to induce precipitation and allowed to stand at room temperature. The precipitate was separated from the mixture, slurried in 80 mL water, adjusted to pH 6.5 to obtain a clear solution, and freeze-dried to obtain 400 mg, the salt of the protected peptide, N-[(2-Sulfo)-9-fluorenlymethoxycarbonyl]$_5$-polymyxin peptide [(NaSO$_3$-Fmoc)$_5$-PBP-3] as a tan powder. The cells remaining after centrifugation were extracted with methanol/water to obtain additional material.

Resin Method: Cells from 1 liter of deacylase enzyme from the original fermentation according to Example 2 were washed 3× with water, brought back to original volume with 0.02 M ammonium phosphate buffer, and combined with 2.0 g of N-(2-sulfo)-9-fluorenlymethoxycarbonyl)]$_5$-polymyxin B. The mixture was placed on a shaker at 175 rpm and maintained at 30° C. for 17 hours. The mixture was then separated by centrifugation and the decant was combined with 20 mL of Amberchrom® CG-161m resin. The resin was washed with 150 mL water, 100 mL 10% $CH_3CN:H_2O$ (3×), and 100 mL 20% $CH_3CN:H_2O$ (2×). The peptide was then eluted 2× with 30% $CH_3CN:H_2O$, evaporated to remove $CH_3CN$, and freeze-dried to obtain 283 mg powder, the protected peptide $(HSO_3$-Fmoc)$_5$-PBP-3. A second amount of peptide was then eluted 3× with 100 mL 50% $CH_3CN:H_2O$. The eluates were combined, evaporated and freeze-dried to obtain 460 mg of the protected peptide as a powder.

A third amount of peptide was extracted from the cells remaining after centrifugation using MeOH: $H_2O$, 6×100 mL each. The extracts were combined, brought to four liters with water, adjusted to pH 2.1 with sulfuric acid and combined with Amberchrom® CG-161m resin. The resin was rinsed with water and then the peptide was eluted with 100 mL 35% $CH_3CN:H_2O$, which was evaporated and freeze-dried to obtain 94 mg of purified peptide. The remaining peptide was eluted with 50% $CH_3CN:H_2O$, evaporated to remove $CH_3CN$, and freeze-dried to obtain 539 mg of the protected peptide. The protected peptide [(2-Sulfo)-9-fluorenylmethoxycarbonyl)]$_5$ polymyxin B peptide[(HSO$_3$-Fmoc)$_5$-PBP-3)] was isolated from this procedure as tan powder, $C_{122}H_{134}N_{16}O_{37}S_5$. Materials prepared by both the resin method and the precipitation method were about 75% pure when analyzed by HPLC with the column eluent monitored at 215 nm. ESIMS: calc. m/z for $C_{122}H_{136}N_{16}O_{37}S_5$: $(M+2H)^{+2}$=1288.4. Found: 1288.

Example 4

Deacylation of the Protected Polymyxin B by the Solubilized Enzyme

Water washed cells from 250 mL of *Actinoplanes utahensis* fermentation as performed according to Example 2 were combined with 125 mL of 0.02 M ammonium phosphate buffer, adjusted to pH 10.1 and stirred thirty minutes. The solution containing the enzyme was separated by centrifuge and adjusted to pH 8.0. This solution was used directly for deacylations or freeze-dried to obtain a powder form for storage. The decant containing the solubilized enzyme at pH 8.0, was combined with 100 mg (HSO$_3$-Fmoc)$_5$-polymyxin B, dissolved in 10 mL of $CH_3CN:H_2O$ (1:1), and placed on a shaker at 175 rpm, 84° C. After two hours the completed reaction was removed from the shaker and adjusted to pH 2.0. The precipitate was mixed with 40 mL methanol and the soluble product was separated from a dark precipitate. The solution, containing 80 mg of the (HSO$_3$-Fmoc)$_5$-PBP-3, was evaporated to 2 mL and added to 10 mL of EtOAc to precipitate the (HSO$_3$-Fmoc)$_5$-PBP-3 as a tan powder.

Example 5

Purification of (NaSO$_3$-Fmoc)$_5$-PBP-3 (protected decapeptide)

(NaSO$_3$-Fmoc)$_5$-PBP-3, 143 mg, was prepared according to the procedure of Example 3. The protected decapeptide was dissolved in 40 mL of 20% $CH_3CN$ 0.05M in sodium phosphate at pH 6.7. Insolubles were removed by centrifugation. The decant was applied to a styrene-divinylbenzene resin cartridge (Supelco EnviChrom-P®, 25×35 mm) which had been slurry packed and rinsed with 20 mL 20% CH$_3$CN-0.05M pH 6.7 buffer. Flow rate was about 2 mL/min at RT. The cartridge was eluted with incrementally increasing concentrations of CH$_3$CN of about 0.05M in sodium phosphate at pH 6.7. Collected fractions were evaluated by analytical HPLC. The desired product was eluted with 33% and 40% CH$_3$CN eluents. Product-containing fractions were pooled and CH$_3$CN removed under vacuum. The product pool was desalted by adsorption onto a 0.5 g styrene-divinylbenzene cartridge (EnviChrom-P®) which was then rinsed with four 1.0 mL portions of distilled water. Product was eluted from the cartridge with 16 mL of 67% CH$_3$CN, the solvent evaporated under vacuum, the pH of the resulting aqueous solution adjusted to about 5.8 with dilute NaOH, then the product was freeze dried. Yield: 72 mg of a light tan solid, (NaSO$_3$-Fmoc)$_5$-PBP-3, C$_{122}$H$_{134}$N$_{16}$O$_{37}$S$_5$. ESIMS: calc. m/z for C$_{122}$H$_{136}$N$_{16}$O$_{37}$S$_5$: (M+2H)$^{+2}$=1288.4. Found: 1288.2.

Example 6

Preparation of N-Phenylthiocarbamyl-(NHaSO$_3$-Fmoc)$_5$-PBP-3 (Compound 4P)

Purified (NaSO$_3$-Fmoc)$_5$-PBP-3, 3.9 mg, was prepared according to the procedure of Example 5. The protected peptide was dissolved in 0.20 mL of 75% MeOH 0.25 M in pH 8.8 potassium borate, and 0.003 mL phenylisothiocyanate was added and stirred at RT. Phenylisothiocyanate is commercially available, e.g., from Aldrich (Milwaukee, Wis.). After about 90 min, the reaction mixture was diluted with 4 mL of 0.4 M ammonium phosphate at pH 7.2. The product solution was applied to a 0.5 g styrene-divinylbenzene resin cartridge (EnviChrom-P®) which was rinsed with 6 mL of 20% CH$_3$CN 0.10 M in sodium phosphate at pH 6.7. Product was eluted using 6 mL of 40% CH$_3$CN 0.05 M in sodium phosphate at pH 6.7. Solvent was evaporated under vacuum and the product was desalted using the procedure of Example 5. Yield: 3.5 mg of a white solid, N-phenylthiocarbamyl-(NaSO$_3$-Fmoc)$_5$-PBP-3, C$_{129}$H$_{137}$N$_{17}$O$_{37}$S$_6$. ESIMS: calc. m/z for C$_{129}$H$_{139}$N$_{17}$O$_{37}$S$_6$: (M+2H)$^{+2}$=1355.4. Found: 1355.6.

Example 7

Preparation of N-Phenylthiocarbamyl-PBP-3 (PTC-PBP-3, Compound 4)

N-Phenylthiocarbamyl-(NHaSO$_3$-Fmoc)$_5$-PBP-3, 8.4 mg, was prepared according to the procedure of Example 6. The protected peptide was dissolved in 0.20 mL dimethylformamide (DMF), 0.010 mL piperidine was added and stirred at RT for 60 min. The reaction mixture was diluted with 4 mL 0.10 M ammonium acetate-0.050 M acetic acid (pH 5.05), 0.006 mL acetic acid, and 4 mL MeOH. The clear solution was applied to a CM-Sepharose® column (10×20 mm, ca. 2 mL volume) which had been conditioned with 50% MeOH 0.05 M in ammonium acetate buffer at pH 5.0. The sample-loaded column was rinsed with 4 mL 50% MeOH-0.05 M ammonium acetate pH 5.0 then with 4 mL 0.05M ammonium acetate pH 5.0 buffer. Product was eluted with 8 mL of 0.27 M sodium sulfate at pH 2.3. The product was further purified by application onto a 0.5 g styrene-divinylbenzene cartridge (EnviChrom-P®) which was eluted with incrementally increasing concentrations of CH$_3$CN 0.05M in pH 2.3 sodium sulfate; product was eluted with 20% CH$_3$CN. Solvent was removed under vacuum from the product-containing fraction pool which was then desalted using the procedure of Example 5, pH adjusted to 6.3 then freeze dried. Yield: 2.7 mg of a white solid, PTC-PBP-3, C$_{54}$H$_{87}$N$_{17}$O$_{12}$S. FABMS: calc. for C$_{54}$H$_{88}$N$_{17}$O$_{12}$S: (M+H)$^+$=1198.7. Found: 1198.5 (M+H)$^+$, 1220.4 (M+Na)$^+$.

Example 8

(NHaSO$_3$-Fmoc)$_4$-PBP-2 (protected nonapeptide)

N-Phenylthiocarbamyl-(NHaSO$_3$-Fmoc)$_5$-PBP-3, 2.9 mg, was prepared according to the procedure of Example 6. The protected peptide was dissolved in 0.30 mL of anhydrous trifluoroacetic acid (TFA) and heated in a 50° C. water bath for 15 min. The TFA was evaporated with a stream of dry nitrogen and the residue was dissolved in 12 mL 0.20M ammonium phosphate at pH 7.2 and 6 mL CH$_3$CN containing 49 mg triglycine (as an acylating agent scavenger). To remove potentially reactive intermediates, the product solution was first applied to a 0.5 g styrene-divinylbenzene resin cartridge (EnviChrom-P®) which was eluted with 10 mL of 40% CH$_3$CN 0.04M in ammonium phosphate at pH 7.2. Product-containing fractions were pooled (~18 mL), diluted with 12 mL distilled water, then applied to a fresh 0.5 g EnviChrom-P® resin cartridge which was eluted with incrementally increasing concentrations of CH$_3$CN about 0.05M in ammonium phosphate at pH 7.2. Product-containing fractions were pooled (~12 mL), 8 mL of 0.54M sodium sulfate pH 2.3 buffer added, and the product was desalted using the procedure of Example 5. The solution pH was adjusted to 5.9 and the sample freeze dried. Yield: 1.8 mg of a white solid, (NaSO$_3$-Fmoc)$_4$-PBP-2, C$_{103}$H$_{116}$N$_{14}$O$_{31}$S$_4$. ESIMS: calc. m/z for C$_{103}$H$_{118}$N$_{14}$O$_{31}$S$_4$ (M+2H)$^{+2}$=1087.3. Found: 1087.0.

Example 9 n-Decanoyl-PBP-3 (Compounds 1 and 1P)

(NaSO$_3$-Fmoc)$_5$-PBP-3, 21.8 mg, was prepared according to the procedure of Example 3. The protected peptide was dissolved in 0.20 mL DMF, 0.020 mL distilled water, and 0.030 mL saturated NaHCO$_3$ (pH~8.9); 4.5 mg n-decanoyl-N-hydroxysuccinimide (activated ester) was added and stirred at RT for 55 min (about 82% conversion by HPLC). An additional 1.8 mg of activated ester was added; after 20 min at RT conversion to Compound 1P was at least 95%. To the reaction mix was added 0.010 mL piperidine. After 35 min at RT the reaction mixture was diluted with 4 mL 0.25 M ammonium sulfate at pH 2.3 yielding a very milky mixture at pH 3.0 which was extracted with 4 mL ethyl acetate; the product-containing aqueous phase was diluted with 4 mL distilled water. Product was initially isolated by size exclusion chromatography on a Sephadex® G-25 column (2.5×40 cm) eluted with 0.10 M ammonium sulfate at pH 2.3. Product-containing fractions were pooled and further purified on a 0.5 g styrene-divinylbenzene cartridge (EnviChrom-P®) by elution with incrementally increasing concentrations of CH$_3$CN about 0.05M in sodium phosphate at pH 6.7; product was eluted with 25% CH$_3$CN. Product was desalted and freeze dried using the procedure of Example 5. Yield: 2.5 mg of a white solid, Compound 1, C$_{57}$H$_{100}$N$_{16}$O$_{13}$. FABMS: calc. for C$_{57}$H$_{101}$N$_{16}$O$_{13}$, (M+H)$^+$=1217.8. Found: 1217 (M+H)$^+$, 1239 (M+Na)$^+$.

Example 10

N-(n-Decanoyl)-p-aminophenylacetyl-PBP-3 (Compounds 2 and 2P)

(NHaSO$_3$-Fmoc)$_5$-PBP-3, 18.5 mg, was prepared according to the procedure of Example 3. The protected peptide was dissolved in 0.20 mL DMF and 0.030 mL saturated NaHCO$_3$ (pH~8.9); 5.8 mg N-(n-decanoyl)-p-aminophenylacetyl-N-hydroxysuccinimide ($C_{10}$-PAPA-OSu) was added and stirred at RT for 50 min (about 69% conversion by HPLC). An additional 2.5 mg of $C_{10}$-PAPA-OSu was added; after 30 min at RT conversion to Compound 2P was about 87%. To the reaction mix was added 0.010 mL piperidine. After 25 min at RT the reaction mixture was diluted with 5 mL 0.20 M ammonium sulfate at pH 2.3 yielding a very milky mixture at pH 2.8 which was extracted with 5 mL ethyl acetate. Product was initially isolated by size exclusion chromatography on a Sephadex® G-25 column (2.5×40 cm) eluted with 0.10 M ammonium sulfate at pH 2.3. Product-containing fractions were pooled and further purified on a 0.5 g styrene-divinylbenzene cartridge (EnviChrom-P®) by elution with incrementally increasing concentrations of $CH_3CN$ about 0.10M in ammonium sulfate at pH 2.3; product was eluted with 30% $CH_3CN$. Further purification was achieved using size exclusion chromatography on a Sephadex® LH-20 column (2.5× 40 cm) eluted with 0.026 M ammonium acetate/0.053 M acetic acid in MeOH. Product-containing fractions were evaporated under vacuum to near dryness, the residue dissolved in 10 mL distilled water, then desalted and freeze dried using the procedure of Example 5. Yield: 2.5 mg of a white solid, Compound 2, $C_{65}H_{107}N_{17}O_{14}$. FABMS: calc. for $C_{65}H_{108}N_{17}O_{14}$, $(M+H)^+ = 1350.8$. Found: 1351 $(M+H)^+$, 1373 $(M+Na)^+$.

Example 11 n-Octanoylcarbamyl-PBP-3 (Compounds 3 and 3P)

$(NaSO_3$-Fmoc$)_5$-PBP-3, 10.2 mg, was prepared according to the procedure of Example 3. The protected peptide was dissolved in 0.20 mL DMF and 0.020 mL distilled water; 0.003 mL octyl isocyanate was added and stirred at RT for 60 min (about 31% conversion by HPLC). Octyl isocyanate is commercially available, e.g., from Aldrich (Milwaukee, Wis.). To the reaction mixture was added 0.020 mL saturated $NaHCO_3$ pH 8.9; after 20 min at RT conversion to Compound 3P was about 91%. After another 35 min at RT 0.010 mL piperidine was added. After 30 min at RT the reaction mixture was diluted with 4 mL 0.026 M ammonium acetate/0.053 M acetic acid in MeOH and the product was isolated by size exclusion chromatography on a Sephadex® LH-20 column as described in Example 10. Product-containing fractions were evaporated under vacuum to near dryness, the residue dissolved in 8 mL distilled water, then desalted and freeze dried using the procedure of Example 5. Yield: 2.3 mg of a white solid, Compound 3, $C_{56}H_{99}N_{17}O_{13}$. FABMS: calc. for $C_{56}H_{100}N_{17}O_{13}$, $(M+H)^+ = 1218.8$. Found: 1219 $(M+H)^+$, 1241 $(M+Na)^+$.

Example 12

Phenylcarbamyl-PBP-3 (Compounds 5 and 5P)

$(NaSO_3$-Fmoc$)_5$-PBP-3, 19.8 mg, (ca. 85% pure) was prepared according to the procedure of Example 3. The protected peptide was dissolved in 0.20 mL DMF and 0.020 mL saturated $NaHCO_3$ pH 8.7; 0.005 mL phenyl isocyanate was added and stirred at RT to obtain Compound 5P. Phenyl isocyanate is commercially available, e.g., from Aldrich (Milwaukee, Wis.). After 45 min 0.020 mL of piperidine was added to remove protecting groups. After 45 min at RT the reaction mixture was diluted with 4 mL 0.10 M ammonium acetate-0.05 M acetic acid, 0.012 mL acetic acid and 4 mL MeOH yielding a clear solution at apparent pH 6.2. The product was isolated on a CM-Sepharose® column as described in Example 7. The product was further purified on a 0.5 g styrene-divinylbenzene cartridge (EnviChrom-P®) using incrementally increasing concentrations of $CH_3CN$ 0.05 M in sodium sulfate at pH 2.3; product was eluted with 20% $CH_3CN$. Product-containing fractions were desalted and freeze dried using the procedure of Example 5. Yield: 4.4 mg of a white solid, Compound 5, $C_{54}H_{87}N_{17}O_{13}$. FABMS: calc. for $C_{54}H_{88}N_{17}O_{13}$, $(M+H)^+ = 1182.7$. Found: 1183 $(M+H)^+$, 1205 $(M+Na)^+$, 1221 $(M+K)^+$.

Example 13

Benzoyl-PBP-3 (Compounds 6 and 6P)

$(NaSO_3$-Fmoc$)_5$-PBP-3, 20.4 mg, (ca. 85% pure) was prepared according to the procedure of Example 3. The protected peptide was dissolved in 0.20 mL DMF and 0.020 mL saturated $NaHCO_3$ pH 8.0; 8.4 mg of benzoyl-N-hydroxysuccinimide was added and stirred at 29° C. to obtain Compound 6P. After 60 min 0.020 mL of piperidine was added. After 20 min at RT the reaction mixture was diluted with 4 mL 0.10 M ammonium acetate-0.05 M acetic acid, 0.013 mL acetic acid and 4 mL MeOH yielding a clear solution. The product was isolated on a CM-Sepharose® column as described in Example 7. The product was further purified by preparative HPLC using a Delta-Pak® C18 column (25×210 mm, Waters Corp.) eluted with an isopropanol gradient (18%-23% over 100 min, linear, at 5 mL/min) buffered with 0.05M sodium sulfate at pH 2.5. Product-containing fractions were pooled, solvent removed under vacuum, and product was desalted and freeze dried using the procedure of Example 5. Yield: 1.6 mg of a white solid, Compound 6, $C_{54}H_{86}N_{16}O_{13}$. FABMS: calc. for $C_{54}H_{87}N_{16}O_{13}$, $(M+H)^+ = 1166.7$. Found: 1167 $(M+H)^+$, 1189 $(M+Na)^+$.

Example 14 of 2-Naphthoxyacetyl-PBP-3 (Compounds 7 and 7P)

$(NaSO_3$-Fmoc$)_5$-PBP-3, 19.0 mg, was prepared according to the procedure of Example 3. The protected peptide was dissolved in 0.40 mL of 75% MeOH 0.25 M in pH 8.8 potassium borate; 6.3 mg of 2-naphthoxyacetyl-N-hydroxysuccinimide was added and stirred at RT to produce Compound 7P. After 35 min 0.020 mL piperidine was added. After 30 min at RT the reaction mixture was diluted and product isolated on a CM-Sepharose® column as in Example 7. Product was further purified on a 0.5 g styrene-divinylbenzene cartridge (EnviChrom-P®) using incrementally increasing concentrations of $CH_3CN$ about 0.05 M in sodium sulfate at pH 2.3; product was eluted with 25% $CH_3CN$. Product-containing fractions were pooled, diluted with an equal volume of distilled water, and product was desalted and freeze dried using the procedure of Example 5. Yield: 4.7 mg of a white solid, Compound 7, $C_{59}H_{90}N_{16}O_{14}$.
FABMS: calc. for $C_{59}H_{91}N_{16}O_{14}$, $(M+H)^+ = 1247.7$. Found: 1247 $(M+H)^+$, 1269 $(M+Na)^+$.

Example 15 p-Toluenesulfonyl-PBP-3 (Compounds 8 and 8P)

$(NaSO_3$-Fmoc$)_5$-PBP-3, 21.7 mg, was prepared according to the procedure of Example 3. The protected peptide was dissolved in 0.50 mL of 75% MeOH 0.25 M in pH 8.8 potassium borate; 5.1 mg of p-toluenesulfonyl chloride was added and stirred at RT to produce Compound 8P. p-Toluenesulfonyl chloride is commercially available, e.g., from Aldrich (Milwaukee, Wis.). After 60 min 0.020 mL piperidine was added. After 30 min at RT the reaction mixture was diluted and product isolated on a CM-Sepharose® column as described in Example 7. Product was further purified on a 0.5 g styrene-divinylbenzene cartridge (EnviChrom-P®) using incrementally increasing concentrations of $CH_3CN$ about 0.05 M in sodium sulfate at pH 2.3; product was eluted with 20% CH$_3$CN. Product-containing fractions were pooled, diluted with an equal volume of distilled water, and product was desalted and freeze dried using the procedure of Example 5. Yield: 4.9 mg of a white solid, Compound 8, C$_{54}$H$_{55}$N$_{16}$O$_{14}$S. FABMS: calc. for C$_{54}$H$_{59}$N$_{16}$O$_{14}$S (M+H)$^+$=1217.6. Found: 1217 (M+H)$^+$, 1239 (M+Na)$^+$.

Example 16 n-Octanoylcarbamyl-PBP-2 (Compounds 9 and 9P)

(NaSO$_3$-Fmoc)$_4$-PBP-2, 10.1 mg, was prepared according to the procedure of Example 8. The protected peptide was dissolved in 0.20 mL DMF and 0.020 mL saturated NaHCO$_3$ pH 8.7; 0.003 mL octyl isocyanate was added and stirred at RT to produce Compound 9P. Octyl isocyanate is commercially available, e.g., from Aldrich (Milwaukee, Wis.). After 45 min at RT 0.020 mL piperidine was added. After 40 min at RT the reaction mixture was diluted with 10 mL 20% CH$_3$CN containing 0.014 mL H$_2$SO$_4$. Product was isolated on a 0.5 g styrene-divinylbenzene cartridge (EnviChrom-P®) using incrementally increasing concentrations of CH$_3$CN about 0.05M in sodium sulfate at pH 2.3; product was eluted with 25% and 30% CH$_3$CN. Product-containing fractions were pooled, solvent removed under vacuum, 2 mL 1.0 M ammonium acetate pH 5.0 buffer was added, pH adjusted to 5.0 by addition of ca. 0.6 mL 1.5 M NH$_4$OH, and then diluted with an equal volume of MeOH. Product was isolated via CM-Sepharose® chromatography as described in Example 7. The product was further purified on a 0.5 g styrene-divinylbenzene cartridge as above but using eluents at pH 9.9 (0.10 M NH$_4$OH-0.01 M (NH$_4$)$_2$SO$_4$); product eluted with 30% CH$_3$CN. Product-containing fractions were pooled, solvent removed under vacuum, and product was desalted and freeze dried using the procedure of Example 5. Yield: 2.7 mg of a white solid, C$_{52}$H$_{92}$N$_{16}$O$_{11}$. FABMS: calc. for C$_{52}$H$_{93}$N$_{16}$O$_{11}$, (M+H)$^+$=1118.7. Found: 1119 (M+H)$^+$, 1141 (M+Na)$^+$, 1157 (M+K)$^+$.

Example 17

N-(n-Decylsulfonyl)glycyl-PBP-2 (Compounds 10 and 10P)

Purified (NaSO$_3$-Fmoc)$_4$-PBP-2, 9.7 mg, was prepared according to the procedure of Example 8. The protected peptide was dissolved in 0.20 mL DMF and 0.020 mL saturated NaHCO$_3$ pH 8.7; 5.2 mg of n-decylsulfonamidoglycyl-N-hydroxy succinimide was added and stirred at RT to produce Compound 10P. After 45 min 0.020 mL piperidine was added. After another 40 min at RT the reaction mixture was diluted and product isolated on a CM-Sepharose® column as described in Example 7. Product was further purified on a 0.5 g styrene-divinylbenzene cartridge (EnviChrom-P®) using incrementally increasing concentrations of CH$_3$CN about 0.05M in sodium sulfate at pH 2.3; product was eluted with 33% CH$_3$CN. Product-containing fractions were pooled, solvent removed under vacuum, and product was desalted and freeze dried using the procedure of Example 5. Yield: 1.5 mg of a white solid, Compound 10, C$_{55}$H$_{97}$N$_{15}$O$_{14}$S. FABMS: calc. for C$_{55}$H$_{98}$N$_{15}$O$_{14}$S, (M+H)$^+$=1224.7. Found: 1224.5 (M+H)$^+$, 1246.5 (M+Na)$^+$.

Example 18

2-N-(n-Decanoyl)lysyl-PBP-2 (Compounds 11 and 11P)

Purified (NaSO$_3$-Fmoc)$_4$-PBP-2, 10.3 mg, was prepared according to the procedure of Example 8. The protected peptide was dissolved in 0.20 mL of DMF and 0.020 mL of saturated NaHCO$_3$ pH 8.3; 8.7 mg of 6-N-Fmoc-2-N-(n-decanoyl)-lysyl-N-hydroxysuccinimide ester was added and stirred at RT to produce Compound 11P. After 50 min 0.020 mL piperidine was added to remove protecting groups. After 45 min at RT the reaction mixture was diluted and product isolated on a CM-Sepharose® column as described in Example 7. Product was further purified on a 0.5 g styrene-divinylbenzene cartridge (EnviChrom-P®) using incrementally increasing concentrations of CH$_3$CN about 0.05 M in sodium sulfate at pH 2.3; product was eluted with 25% CH$_3$CN. Product-containing fractions were pooled, diluted with an equal volume of distilled water, and product was desalted and freeze dried using the procedure of Example 5. Yield: 2.0 mg of a white solid, Compound 11, C$_{59}$H$_{104}$N$_{16}$O$_{13}$. FABMS: calc. for C$_{59}$H$_{105}$N$_{16}$O$_{13}$, (M+H)$^+$=1245.8. Found: 1245 (M+H)$^+$, 1267 (M+Na)$^+$.

Example 19

N-(n-Decanoyl)phenylalanyl-PBP-2 (Compounds 12 and 12P)

About 10 mg of purified (NaSO$_3$-Fmoc)$_4$-PBP-2 was prepared according to the procedure of Example 8. The protected peptide was dissolved in 0.40 mL of 75% MeOH 0.25M in pH 8.8 potassium borate; 6 mg of N-(n-decanoyl)-phenylalanyl-N-hydroxysuccinimide ester was added and stirred at RT to produce Compound 12P. After 50 min 0.020 mL piperidine was added. After 45 min at RT the reaction mixture was diluted and product isolated on a CM-Sepharose® column as in Example 7. Product was further purified on a 0.5 g styrene-divinylbenzene cartridge (EnviChrom-P®) using incrementally increasing concentrations of CH$_3$CN about 0.05M in sodium sulfate at pH 2.3; product was eluted with 33% CH$_3$CN. Product-containing fractions were pooled, diluted with an equal volume of distilled water, and product was desalted and freeze dried using the procedure of Example 5. Yield: 3.0 mg of a white solid, Compound 12, C$_{62}$H$_{101}$N$_{15}$O$_{13}$. FABMS: calc. for C$_{62}$H$_{102}$N$_{15}$O$_{13}$ (M+H)$^+$=1264.8. Found: 1265 (M+H)$^+$, 1287 (M+Na)$^+$.

Example 20

N-Phenylthiocarbamyl-(NaSO$_3$-Fmoc)$_4$PBP-2 (Compound 24P)

Purified (NaSO$_3$-Fmoc)$_4$-PBP-2, 90.2 mg, was prepared according to the procedure of Example 8. The protected peptide was dissolved in 2.0 mL reaction solvent as in Example 23; 0.050 mL of phenylisothiocyanate was added. Phenylisothiocyanate is commercially available, e.g., from Aldrich (Milwaukee, Wis.). After 87 min stirring at RT the reaction mixture was diluted with 50 mL of 20% CH$_3$CN 0.1M in pH 6.76 sodium phosphate buffer. This solution was applied to a 2.5 g EnviChrom-P® column which was eluted with incrementally increasing concentrations of CH$_3$CN about 0.05M in sodium phosphate at pH 6.76; product was eluted with 30-35% CH$_3$CN. The product was desalted on a 3.1 g EnviChrom-P® column and freeze dried using the procedure of Example 23. Yield: 85 mg of a white solid, Compound 24P.

Example 21

(NaSO$_3$-Fmoc)$_4$PBP-1 (Protected octapeptide)

N-phenylthiocarbamyl-(NaSO$_3$-Fmoc)$_4$-PBP-2 (70.0 mg) was prepared according to the procedure of Example 20. The protected peptide was dissolved in 0.70 mL of anhydrous trifluoroacetic acid (TFA) and heated in a 50° C. water bath for 15 min. TFA was removed using a stream of dry nitrogen. The residue was dissolved in 40 mL of 25% CH$_3$CN 0.05 M in sodium sulfate at pH 2.3. The product was purified by application onto a 2.06 g EnviChrom-P® column which was eluted with incrementally increasing concentrations of CH$_3$CN about 0.05 M in sodium sulfate at pH 2.3; product was eluted with 40% CH$_3$CN. Product-containing fractions were pooled and CH$_3$CN was removed under vacuum at 35° C. The product was desalted by adsorption onto a 3.1 g EnviChrom-P® column which was then rinsed with 8, 8 and 4 mL portions of distilled water. Product was stripped from the column with 40 mL of 60% CH$_3$CN, solvent evaporated under vacuum, and the aqueous solution was freeze dried. Yield: 60 mg of a white solid, protected octapeptide, C$_{99}$H$_{109}$N$_{13}$O$_{29}$S$_4$. ESIMS: calc. m/z for (M+2H)$^{+2}$=1036.8. Found: 1036.4 (M+2H)$^{+2}$.

Example 22

(NaSO$_3$-Fmoc)$_3$PBP (Protected heptapeptide)

(NaSO$_3$-Fmoc)$_4$-PBP-2 (0.35 mg) was prepared according to the procedure of Example 8. The protected peptide was dissolved in 0.40 mL of buffer (0.02M sodium citrate, 0.006M beta-mercaptoethylamine, adjusted to pH 5.5 with HCl).
Cathepsin C (Sigma product code C8511, dipeptidyl aminopeptidase, EC 3.4.14.1) was dissolved in the same buffer at a concentration of 10 units/mL. The cathepsin C solution (0.10 mL) was then added to 0.40 mL of the (NaSO$_3$-Fmoc)$_4$-PBP-2 solution and the mixture was incubated at 37° C. The reaction was monitored by HPLC at 3.0 hrs (about 43% conversion to protected heptapeptide) and at 24 hrs (about 90% conversion). The relative retention time and ultraviolet absorption spectrum of the product peak was consistent with the production of protected heptapeptide; the time-dependent appearance of a short retention time peak with characteristic Fmoc absorption spectrum is consistent with liberation of the N-terminal dipeptide H$_2$N-Thr-Dab(Fmoc)-CO$_2$H from the protected nonapeptide.

Example 23

Isonicotinoyl-PBP-3 (Compounds 13 and 13P)

(NaSO$_3$-Fmoc)$_5$-PBP-3 (20.5 mg) was prepared according to the procedure of Example 3. The protected peptide was dissolved in 0.40 mL of 75% MeOH 0.25M in pH 8.8 potassium borate; 8.7 mg of isonicotinoyl-N-hydroxysuccinimide ester was added. The solution was stirred 63 min at RT to form Compound 13P and then 0.030 mL piperidine was added to remove the protecting groups. After stirring 45 min at RT the reaction mixture was diluted with 10 mL 60% MeOH 0.04 M in pH 5.0 ammonium acetate and 0.019 mL acetic acid. The clear solution was applied to a CM-Sepharose column (10×20 mm, ca. 2 mL volume) which had been conditioned by rinsing with 20 mL of 60% MeOH 0.04M in pH 5.0 ammonium acetate buffer. The sample-loaded column was rinsed with 10 mL of 60% MeOH 0.04M in pH 5.0 ammonium acetate, and then with 4 mL of aqueous 0.05 M pH 5.0 ammonium acetate buffer. Product was eluted with 8 mL of 0.27 M sodium sulfate buffer at pH 2.3. Product was further purified by application onto a 0.5 g styrene-divinylbenzene cartridge (EnviChrom-P) which was eluted with incrementally increasing concentrations of CH$_3$CN about 0.05 M in sodium sulfate at pH 2.3; product was eluted with 15% CH$_3$CN. Product-containing fractions were pooled and CH$_3$CN was removed under vacuum at 35° C. The product solution was desalted by adsorption onto a 0.5 g styrene-divinylbenzene cartridge (EnviChrom-P) which was then rinsed with four 1.0 mL portions of distilled water. Product was stripped from the cartridge with 12 mL of 67% CH$_3$CN, solvent evaporated under vacuum, and the aqueous solution was freeze dried. Yield: 9.4 mg of a white solid, Compound 13, C$_{53}$H$_{85}$N$_{17}$O$_{13}$. FABMS: calc. for C$_{53}$H$_{85}$N$_{17}$O$_{13}$Na (M+Na)$^+$=1190.7. Found: 1190 (M+Na)$^+$.

Example 24

3-Indolylethylcarbamyl-PBP-3 (Compounds 14 and 14P)

(NaSO$_3$-Fmoc)$_5$-PBP-3 (22.5 mg) was prepared according to the procedure of Example 3. The protected peptide was dissolved in 0.30 mL of collidine/acetic acid/water (40:1:4); 18.6 mg of 3-indolylethylcarbamyl-N-hydroxysuccinimide, prepared according to the procedure of Example 43, was added in two increments. The solution was stirred 130 min at RT to form Compound 14P, the reaction mixture was flushed with argon, 0.050 mL piperidine was added to remove the protecting groups, and the mixture again flushed with argon. After stirring 25 min at RT the reaction mixture was diluted with 10 mL 60% MeOH 0.04 M in pH 5.0 ammonium acetate and 0.042 mL acetic acid. Product was isolated from the clear reaction dilution on a CM-Sepharose column as in Example 23. Product was further purified by application onto a 0.5 g styrene-divinylbenzene cartridge (EnviChrom-P) which was eluted with incrementally increasing concentrations of CH$_3$CN about 0.05M in sodium sulfate at pH 2.3; product was eluted with 20% CH$_3$CN. The product was desalted and freeze dried as in Example 23. Yield: 7.3 mg of a white solid, Compound 14, C$_{58}$H$_{92}$N$_{18}$O$_{13}$. FABMS: calc. for C$_{58}$H$_{93}$N$_{18}$O$_{13}$ (M+H)$^+$=1249.7. Found: 1250 (M+H)$^+$.

Example 25

N-Acetyl-p-aminophenylacetyl-PBP-3 (Compounds 15 and 15P)

(NaSO$_3$-Fmoc)$_5$-PBP-3 (20.7 mg) was prepared according to the procedure of Example 3. The protected peptide was dissolved as in Example 23; 5.8 mg of N-acetyl-p-aminophenylacetyl-N-hydroxysuccinimide was added. The solution was stirred 48 min at RT to obtain Compound 15P and then 0.020 mL piperidine was added to remove protecting groups. After stirring 30 min at RT the reaction mixture was diluted with 10 mL 50% MeOH 0.05 M in pH 5.0 ammonium acetate and 0.013 mL acetic acid. Product was isolated from the clear reaction dilution on a CM-Sepharose column in similar fashion as in Example 23. Product was further purified on a 0.5 g EnviChrom-P cartridge which was eluted with incrementally increasing concentrations of CH$_3$CN about 0.05 M in sodium sulfate at pH 2.3; product was eluted with 15% CH$_3$CN. The product was desalted and freeze dried as in Example 23. Yield: 3.2 mg of a white solid, Compound 15, C$_{57}$H$_{91}$N$_{17}$O$_{14}$. FABMS: calc. for C$_{57}$H$_{92}$N$_{17}$O$_{14}$ (M+H)$^+$=1238.7 Found: 1238 (M+H)$^+$.

Example 26

N-(n-Decanoyl)phenylalanyl-PBP-3 (Compounds 16 and 16P)

(NaSO$_3$-Fmoc)$_5$-PBP-3 (24.0 mg) was prepared according to the procedure of Example 3. The protected peptide was dissolved as in Example 24; 12.9 mg of N-(n-decanoyl)phenylalanyl-N-hydroxysuccinimide was added. The solution was stirred 48 min at RT to form compound 16P, and then 0.050 mL piperidine was added to remove protecting groups. After stirring 30 min at RT the reaction mixture was diluted and product was isolated on a CM-Sepharose column as in Example 24. Product was further purified on a 0.5 g EnviChrom-P cartridge eluted with incrementally increasing concentrations of CH$_3$CN about 0.05 M in sodium sulfate at pH 2.3; product was eluted with 30% $CH_3CN$. The product was desalted and freeze dried as in Example 23. Yield: 7.5 mg of a white solid, Compound 16, $C_{66}H_{109}N_{17}O_{14}$. FABMS: calc. for $C_{66}N_{110}N_{17}O_{14}$, $(M+H)^+=1364.8$. Found: 1365 $(M+H)^+$.

Example 27

4-n-Decylphenylcarbamyl-PBP-3 (Compounds 17 and 17P)

$(NaSO_3-Fmoc)_5$-PBP-3 (12.1 mg) was prepared according to the procedure of Example 3. The protected peptide was dissolved in 0.40 mL of collidine/acetic acid/water (20:1:2); 9.7 mg of 4-n-decylphenylcarbamyl-N-hydroxysuccinimide, prepared according to the procedure of Example 43, was added in two increments along with 0.030 mL of diisopropylethylamine and stirred about 2 hrs at RT to form Compound 17P. Piperidine, 0.055 mL was added to remove blocking groups. After stirring 40 min at RT the reaction mixture was diluted with 10 mL 60% MeOH 0.04 M in pH 5.0 ammonium acetate and 0.060 mL acetic acid. Product was isolated from the reaction dilution filtrate (PVDF membrane) on a CM-Sepharose column as in Example 23. The product was desalted and freeze dried as in Example 23. Yield: 5.0 mg of a white solid, Compound 17, $C_{64}H_{105}N_{17}O_{13}$. FABMS: calc. for $C_{64}H_{106}N_{17}O_{13}$ $(M+H)^+=1320.8$. Found: 1322 $(M+H)^+$.

Example 28

4-Biphenylcarbamyl-PBP-3 (Compounds 18 and 18P)

$(NaSO_3-Fmoc)_5$-PBP-3 (11.9 mg) was prepared according to the procedure of Example 3. The protected peptide was dissolved in 0.30 mL of collidine/acetic acid/water (20:1:2); 7.0 mg of 4-biphenyl isocyanate (commercially available, e.g., from Aldrich (Milwaukee, Wis.)) was added in two increments. After stirring about 2 hrs at RT to form Compound 18P, 0.050 mL piperidine was added to remove protecting groups. After stirring 32 min at RT the reaction mixture was diluted with 10 mL 60% MeOH 0.04M in pH 5.0 ammonium acetate and 0.035 mL acetic acid. Product was isolated from the reaction dilution filtrate (PVDF membrane) on a CM-Sepharose column as in Example 23. The product was desalted and freeze dried as in Example 23. Yield: 5.1 mg of a white solid, Compound 18, $C_{60}H_{91}N_{17}O_{13}$. FABMS: calc. for $C_{60}H_{92}N_{17}O_{13}$ $(M+H)^+=1258.7$. Found: 1258 $(M+H)^+$.

Example 29

Benzyloxyacetyl-PBP-3 (Compounds 19 and 19P)

$(NaSO_3-Fmoc)_5$-PBP-3 (23.5 mg) was prepared according to the procedure of Example 3. The protected peptide was dissolved as in Example 24; 12.5 mg of benzyloxyacetyl-N-hydroxysuccinimide ester was added and the solution was stirred 56 min at RT to form Compound 19P. Piperidine, 0.050 mL, was then added to remove protecting groups. After stirring 30 min at RT the reaction mixture was diluted and product was isolated on a CM-Sepharose column as in Example 24. Product was further purified on a 0.5 g EnviChrom-P cartridge eluted with incrementally increasing concentrations of $CH_3CN$ about 0.05 M in sodium sulfate at pH 2.3; product was eluted with 17.5% $CH_3CN$. The product was desalted and freeze dried as in Example 23. Yield: 7.7 mg of a white solid, Compound 19, $C_{56}H_{90}N_{16}O_{14}$. FABMS: calc. for $C_{56}H_{91}N_{16}O_{14}$, $(M+H)^+=1211.7$. Found: 1211 $(M+H)^+$.

Example 30

4-Phenyloxyphenylcarbamyl-PBP-3 (Compounds 20 and 20P)

$(NaSO_3-Fmoc)_5$-PBP-3 (16.6 mg) was prepared according to the procedure of Example 3. The protected peptide was dissolved as in Example 24; 7.7 mg of 4-phenyloxyphenyl isocyanate was added and the solution was stirred 85 min at RT to form Compound 20P. 4-phenyloxyphenyl isocyanate is commercially available, e.g., from Aldrich (Milwaukee, Wis.). Piperidine, 0.040 mL, was added to remove the protecting groups. After stirring 15 min at RT the reaction mixture was diluted and product was isolated on a CM-Sepharose column in similar fashion as in Example 24. Product was further purified on a 0.5 g EnviChrom-P cartridge eluted with incrementally increasing concentrations of $CH_3CN$ about 0.05 M in sodium sulfate at pH 2.3; product was eluted with 25% $CH_3CN$. The product was desalted and freeze dried as in Example 23. Yield: 5.1 mg of a white solid, Compound 20, $C_{60}H_{91}N_{17}O_{14}$. FABMS: calc. for $C_{60}H_{92}N_{17}O_{14}$, $(M+H)^+=1274.7$. Found: 1274 $(M+H)^+$.

Example 31

4-Chlorophenylcarbamyl-PBP-3 (Compounds 21 and 21P)

$(NaSO_3-Fmoc)_5$-PBP-3 (12.0 mg) was prepared according to the procedure of Example 3. The protected peptide was dissolved as in Example 24; about 8.2 mg of 4-chlorophenyl isocyanate was added in two increments. 4-Chlorophenylisocyanate is commercially available, e.g., from Aldrich (Milwaukee, Wis.). The solution was stirred 80 min at RT to form Compound 21P, and then 0.040 mL piperidine was added to remove protecting groups. The reaction mixture was stirred 27 min at RT and diluted as in Example 23. The product was isolated from the diluted reaction filtrate (PVDF membrane) on a CM-Sepharose column as in Example 23. Product was further purified on a 0.5 g EnviChrom-P cartridge eluted with incrementally increasing concentrations of $CH_3CN$ about 0.05 M in sodium sulfate at pH 2.3; product was eluted with 25% $CH_3CN$. The product was desalted and freeze dried as in Example 23. Yield: 3.6 mg of a white solid, Compound 21, $C_{54}H_{86}N_{17}O_{13}Cl$. FABMS: calc. for $C_{54}H_{87}N_{17}O_{13}Cl$, $(M+H)^+=1216.6$. Found: 1216 $(M+H)^+$.

Example 32

Benzylcarbamyl-PBP-3 (Compounds 22 and 22P)

$(NaSO_3-Fmoc)_5$-PBP-3 (12.2 mg) was prepared according to the procedure of Example 3. The protected peptide was dissolved as in Example 24; about 0.004 mL of benzyl isocyanate (commercially available, e.g., from Aldrich (Milwaukee, Wis.)) was added. The solution was stirred 45 min at RT to form Compound 22P, and then 0.040 mL piperidine was added to remove the protecting groups. After stirring 35 min at RT the reaction mixture was diluted as in Example 23 and product was isolated from the reaction dilution on a CM-Sepharose column as in Example 23. The product was desalted and freeze dried as in Example 23. Yield: 5.5 mg of a white solid, Compound 22, $C_{55}H_{89}N_{17}O_{13}$. FABMS: calc. for $C_{55}H_{90}N_{17}O_{13}$, $(M+H)^+=1196.7$. Found: 1196 $(M+H)^+$.

Example 33

Cyclohexylcarbamyl-PBP-3 (Compounds 23 and 23P)

$(NaSO_3-Fmoc)_5$-PBP-3 (19.3 mg) was prepared according to the procedure of Example 3. The protected peptide was dissolved as in Example 24; 0.008 mL of cyclohexyl isocyanate was added. Cyclohexyl isocyanate is commercially available, e.g., from Aldrich (Milwaukee, Wis.). The solution was stirred 30 min at RT to form Compound 23P, and then 0.050 mL piperidine was added to remove protecting groups. The reaction mixture was stirred 35 min at RT and diluted. Product was isolated on a CM-Sepharose column as in Example 24 and then further purified on a 0.5 g EnviChrom-P cartridge eluted with incrementally increasing concentrations of $CH_3CN$ about 0.05 M in sodium sulfate at pH 2.3; product was eluted with 18% $CH_3CN$. The product was desalted and freeze dried as in Example 23. Yield: 5.1 mg of a white solid, Compound 23, $C_{54}H_{93}N_{17}O_{13}$. FABMS: calc. for $C_{54}H_{94}N_{17}O_{13}$, $(M+H)^+=1188.7$. Found: 1189 $(M+H)^+$.

Example 34

Phenylthiocarbamyl-PBP-2 (Compound 24)

Purified phenylthiocarbamyl-$(NaSO_3$-Fmoc$)_4$-PBP-2 (13.7 mg, compound 24P from Example 20) was dissolved in 0.20 mL of DMF and 0.010 mL of piperidine. After stirring 15 min at RT the reaction mixture was diluted with 8 mL 50% MeOH 0.05M in pH 5.0 ammonium acetate and 0.006 mL of acetic acid. Product was isolated from the reaction dilution on a CM-Sepharose column in similar fashion as in Example 23. The product was desalted and freeze dried as in Example 23. Yield: 6.9 mg of a white solid, Compound 24, $C_{50}H_{80}N_{15}O_{11}S$ FABMS: calc. for $C_{50}H_{81}N_{15}O_{11}S$ $(M+H)^+=1098.6$. Found: 1099 $(M+H)^+$.

Example 35 n-Decanoyl-PBP-1 (Compounds 25 and 25P)

$(NaSO_3$-Fmoc$)_4$-PBP-1 (16.2 mg) was prepared according to example to Example 20. The protected peptide was dissolved as in Example 24; 12.6 mg of n-decanoyl-N-hydroxysuccinimide ester was added in two increments. The solution was stirred about 2 hrs at RT to form Compound 25P and then 0.050 mL of piperidine was added to remove the protecting groups. After stirring 37 min at RT the reaction mixture was diluted and product was isolated on a CM-Sepharose column as in Example 24. The product was further purified on a 0.5 g EnviChrom-P cartridge eluted with incrementally increasing concentrations of $CH_3CN$ about 0.05 M in sodium sulfate at pH 2.3; product was eluted with 24% $CH_3CN$. The product was desalted and freeze dried as in Example 23. Yield: 2.6 mg of a white solid, Compound 25, $C_{49}H_{85}N_{13}O_{10}$. FABMS: calc. for $C_{49}H_{86}N_{13}O_{10}$, $(M+H)^+=1016.7$. Found: 1017 $(M+H)^+$.

Example 36 n-Octylcarbamyl-colistin decapeptide (Compounds 51 and 51P)

$(NaSO_3$-Fmoc$)_5$-colistin decapeptide (20.2 mg), prepared according to the procedure of Example 45, was dissolved as in Example 24; 0.006 mL of n-octyl isocyanate was added. Ocyl isocyanate is commercially available, e.g., from Aldrich (Milwaukee, Wis.). The solution was stirred 48 min at RT to form Compound 51P, and then 0.050 mL piperidine was added to remove the protecting groups. After stirring 25 min at RT the reaction mixture was diluted and filtered through a PVDF-membrane. The product was isolated from the filtrate on a CM-Sepharose column as in Example 24. Product was further purified on a 0.5 g EnviChrom-P cartridge eluted with incrementally increasing concentrations of $CH_3CN$ about 0.05M in sodium sulfate at pH 2.3; product was eluted with 22% $CH_3CN$. The product was desalted and freeze dried as in Example 23. Yield: 3.0 mg of a white solid, Compound 51, $C_{53}H_{101}N_{17}O_{13}$. FABMS: calc. for $C_{53}H_{102}N_{17}O_{13}$, $(M+H)^+=1184.8$. Found: 1185 $(M+H)^+$.

Example 37

N-(n-Decanoyl)phenylalanyl-colistin decapeptide (Compounds 52 and 52P)

$(NaSO_3$-Fmoc$)_5$-colistin decapeptide (20.7 mg), prepared according to the procedure of Example 45, was dissolved as in Example 24; 9.5 mg of N-(n-decanoyl)phenylalanyl-N-hydroxysuccinimide ester was added. The solution was stirred 46 min at RT to form Compound 52P, and then 0.050 mL piperidine was added to remove protecting groups. The reaction mixture was stirred 25 min at RT and diluted. Product was isolated on a CM-Sepharose column as in Example 24 and further purified on a 0.5 g EnviChrom-P cartridge eluted with incrementally increasing concentrations of $CH_3CN$ about 0.05 M in sodium sulfate at pH 2.3; product was eluted with 30.5% $CH_3CN$. The product was desalted and freeze dried as in Example 23. Yield: 2.5 mg of a white solid, Compound 52, $C_{63}H_{111}N_{17}O_{14}$. FABMS: calc. for $C_{63}H_{112}N_{17}O_{14}$, $(M+H)^+=1330.9$. Found: 1331 $(M+H)^+$.

Example 38

P-Toluenesulfonyl-Colistin decapeptide (Compounds 53 and 53P)

$(NaSO_3$-Fmoc$)_5$-colistin decapeptide (20.8 mg), prepared according to the procedure of Example 45, was dissolved as in Example 24; 6.8 mg of p-toluenesulfonyl chloride (commercially available, e.g., from Aldrich (Milwaukee, Wis.)) was added. The reaction was stirred 51 min at RT to form Compound 53P and then 0.050 mL piperidine was added to remove protecting groups. After stirring 47 min at RT the reaction mixture was diluted and product was isolated on a CM-Sepharose column as in Example 24. Product was further purified on a 0.5 g EnviChrom-P cartridge eluted with incrementally increasing concentrations of $CH_3CN$ about 0.05 M in sodium sulfate at pH 2.3; product was eluted with 20% $CH_3CN$. The product was desalted and freeze dried as in Example 23. Yield: 1.1 mg of a white solid, Compound 53, $C_{51}H_{90}N_{16}O_{14}S$. FABMS: calc. for $C_{51}H_{91}N_{16}O_{14}S$, $(M+H)^+=1183.7$. Found: 1184 $(M+H)^+$.

Example 39

Isolation of [Ile$^7$]-Polymyxin B$_1$ and [Leu$^7$]-Polymyxin B$_1$

Commercial polymyxin B sulfate (46 mg) was dissolved in 10 mL of 0.05 M sodium sulfate pH 2.3 buffer. About 9 mL of the sample solution was injected onto a Waters Delta-Pak® C-18 Radial-Pak column (2.5×21 cm) which was eluted at room temperature at 5.0 mL/min with a 22% to 32% $CH_3CN$ linear gradient over 120 min; eluents were buffered with about 0.04 M sodium sulfate at pH 2.3. UV absorption of the eluate was monitored at 225 nm. The [Ile$^7$] variant eluted at about 65 min and the major component, polymyxin B$_1$ ([Leu$^7$]-polymyxin B$_1$), eluted at about 77 min. As determined by analytical HPLC, fractions containing the desired products were separately pooled, $CH_3CN$ was evaporated under vacuum at 35° C., and the aqueous solutions were desalted and freeze dried as in Example 23. Yields: 3.8 mg of a white solid, [Ile$^7$]-polymyxin B$_1$, $C_{56}H_{98}N_{16}O_{13}$. FABMS: calc. for $C_{56}H_{99}N_{16}O_{13}$, $(M+H)^+=1203.8$. Found: 1204 $(M+H)^+$; 18 mg of a white solid, [Leu$^7$]-polymyxin B$_1$, $C_{56}H_{98}N_{16}O_{13}$. FABMS: calc. for $C_{56}H_{99}N_{16}O_{13}$, $(M+H)^+=1203.8$. Found: 1204 $(M+H)^+$. About 2 mg each of the products were separately dissolved in 1.0 mL of 6M HCl and heated at about 120° C. for 22 hrs. The solvent was removed by evaporation under vacuum at 50° C. and the residues were dissolved in 1.0 mL of distilled water. The samples were derivatized with Fmoc chloride in pH 10.1 sodium borate buffered aqueous $CH_3CN$ for 5 min at 50° C. Amino acid Fmoc derivatives were separated at pH 6.7 on an analytical reversed phase column (C18, 15 cm) eluted with a $CH_3CN$ gradient at 40° C. Peak areas were integrated at 264 nm and amino acids were identified by correspondence of retention times to reference Fmoc amino acids.

| | | Mole Ratios (Phe = 1.00) | | | |
|---|---|---|---|---|---|
| | | [Ile$^7$]-PB$_1$ | | [Leu$^7$]-PB$_1$ | |
| Amino Acid | Retn t(min) | Expected | Found | Expected | Found |
| Unknown | 3.63 | 0.00 | 0.07 | 0.00 | 0.09 |
| Ser | 3.82 | 0.00 | 0.07 | 0.00 | 0.00 |
| Thr | 4.39 | 2.00 | 1.76 | 2.00 | 1.82 |
| Ile | 8.25 | 1.00 | 0.88 | 0.00 | 0.00 |
| Leu | 8.57 | 0.00 | 0.13 | 1.00 | 1.00 |
| Phe | 9.38 | 1.00 | 1.00 | 1.00 | 1.00 |
| Dab | 16.35 | 6.00 | 5.82 | 6.00 | 5.75 |

Example 40

Cyclohexylcarbamyl-[Ile$^7$]-Polymyxin Decapeptide (Compounds 48 and 48P)

$(NaSO_3\text{-Fmoc})_5$-PBP-3 (55.8 mg) was prepared according to the procedure of Example 3. The protected peptide was dissolved in 0.60 mL of reaction solvent as in Example 24; 0.012 mL of cyclohexyl isocyanate was added. Cyclohexyl isocyanate is commercially available, e.g., from Aldrich. The solution was stirred 50 min at RT to form Compound 48P and then 0.10 mL piperidine was added to remove the protecting groups. After stirring 30 min at RT the reaction mixture was diluted and product was isolated on a CM-Sepharose column in similar fashion as in Example 24. The product-containing fractions were pooled (8 mL) and injected onto a Waters Delta-Pak® C-18 Radial-Pak column (2.5×21 cm) which was eluted at room temperature at 5.0 mL/min with a 15% to 25% $CH_3CN$ linear gradient over 120 min; eluents were buffered with about 0.04 M sodium sulfate at pH 2.3. UV absorption of the eluate was monitored at 225 nm. The cyclohexylcarbamyl-[Ile$^7$] variant (Compound 48) eluted at about 83 min and the major component, cyclohexylcarbamyl-[Leu$^7$]-polymyxin decapeptide (Compound 23), eluted at about 93 min. Product fractions were pooled, desalted, and freeze dried as in Example 39. Yields: 2.6 mg of a white solid, Compound 48, $C_{54}H_{93}N_{17}O_{13}$. FABMS: calc. for $C_{54}H_{94}N_{17}O_{13}$, $(M+H)^+=1188.7$. Found: 1189 $(M+H)^+$; and 20.1 mg of a white solid, Compound 23. Amino acid analyses were performed on both samples in similar fashion as in Example 39.

| | | Mole Ratios (Phe = 1.00) | | | |
|---|---|---|---|---|---|
| | | [Ile$^7$]-variant | | [Leu$^7$]-variant | |
| Amino Acid | Retn t(min) | Expected | Found | Expected | Found |
| Unknown | 3.12 | 0.00 | 0.09 | 0.00 | 0.14 |
| Thr | 3.72 | 2.00 | 1.86 | 2.00 | 1.82 |
| Ile | 7.06 | 1.00 | 0.96 | 0.00 | 0.00 |
| Leu | 7.34 | 0.00 | 0.04 | 1.00 | 1.00 |
| Phe | 8.09 | 1.00 | 1.00 | 1.00 | 1.00 |
| Dab | 14.96 | 6.00 | 5.49 | 6.00 | 5.44 |

Example 41

Preparation of 2-N-(n-Decanoyl)lysyl-PBP-3 (Compounds 54 and 54P)

$(NaSO_3\text{-Fmoc})_5$-PBP-3 (21.7 mg) was prepared according to the procedure of Example 3. The protected peptide was dissolved as in Example 24; 11.8 mg of 6-N-Fmoc-2-N-(n-decanoyl)lysyl-N-hydroxysuccinimide was added. The solution was stirred 45 min at RT to form Compound 54P and then 0.050 mL of piperidine was added to remove protecting groups. After stirring 30 min at RT the reaction mixture was diluted and product was isolated on a CM-Sepharose column as in Example 24. Product was further purified on a 0.5 g EnviChrom-P cartridge eluted with incrementally increasing concentrations of $CH_3CN$ about 0.05M in sodium sulfate at pH 2.3; product was eluted with 22.5% $CH_3CN$. The product was desalted and freeze dried as in Example 23. Yield: 7.2 mg of a white solid, Compound 54, $C_{63}H_{112}N_{15}O_{14}$. FABMS: calc. for $C_{63}H_{113}N_{18}O_{14}$ $(M+H)^+=1345.9$. Found: 1346 $(M+H)^+$.

Example 42

4-n-Decylphenylcarbamyl-N-hydroxysuccinimide

A mixture of p-decylaniline (0.4504 g, 1.93 mmols), disuccinimidyl carbonate (0.5840 g, 2.28 mmols) and triethylamine (0.26 mL, 1.93 mmols) in 10 mL of acetonitrile was stirred at room temperature overnight. A small amount of insoluble solid was filtered off and the filtrate was evaporated to dryness. The residue was taken up in ethyl acetate and extracted with 0.5 N hydrochloric acid, water, saturated sodium bicarbonate solution and brine, dried over magnesium sulfate and evaporated to the product, $C_{21}H_{30}N_2O_4$, a beige solid, yield 0.3784 g., FABMS: calc. for $C_{21}H_{31}N_2O_4$, $(M+H)^+=375.2$. Found 375 $(M+H)^+$. This intermediate was used in Example 27 to prepare Compounds 17 and 17P.

Example 43

3-Indolylethylcarbamyl-N-hydroxysucinnimide

A solution of tryptamine (0.1730 g, 1.08 mmol) and disuccinimidyl carbonate (0.5213 g, 2.03 mmol) in 20 mL of acetonitrile was stirred at room temperature overnight. The reaction mixture was evaporated to dryness and slurried in ethyl acetate and filtered from insoluble solid. Evaporation of the ethyl acetate gave a glass-like solid which was purified by gradient-elution chromatography on silica gel using ethyl acetate:hexane. The product was eluted with ethyl acetate: hexane (8:2) to afford 0.1402 g of the desired compound, $C_{15}H_{15}N_3O_4$, FABMS: calc. for $C_{15}H_{15}N_3O_4$, $M^+=301.1$. Found 301 $(M)^+$. This intermediate was used to prepare Compounds 14 and 14P in Example 24.

Example 44

N-[(2-Sulfo)-9-fluorenylmethoxycarbonyl)]$_5$-colistin [(HSO$_3$-Fmoc)$_5$-colistin]

Colistin sulfate (polymyxin E) (0.2481 g., 0.1956 mmol) was dissolved in a solution of 7.0 mL, saturated sodium bicarbonate, 7.0 mL of water and 7.0 mL of tetrahydrofuran. Colistin sulfate is commercially available from Sigma (Milwaukee, Wis.). A solution of (2-sulfo)-9-fluorenylmethoxy-N-hydroxysuccinimide (0.5017 g, 1.203 mmol) in 5 mL of tetrahydrofuran was added in several portions over 45 min. The reaction was stirred at room temperature over night, then diluted with 20 mL of water, and acidified with 10 mL of 6N hydrochloric acid to give an oily precipitate. The mixture was chilled and the aqueous layer decanted and the oily residue was dissolved in 100 mL of ethanol. The ethanol was evaporated under vacuum (35° C.) and the resulting solid was triturated with ethyl acetate, filtered and dried to afford 0.431 g of product HPLC with a gradient on a reverse phase column showed a single major peak, N-[2-(sulfo)-9-fluorenyl-methoxycarbonyl]$_5$-colistin,[$C_{128}H_{152}N_{16}O_{35}S_5$], ESIMS: calc. m/z for $C_{125}H_{154}N_{16}O_{38}S_5$ $(M+2H)^{+2}$=1341.4. Found: 1341.6

The above procedure can be used with 2(sulfo-9-)fluorenylmethoxycarbonyl chloride with similar results.

Example 45

(NaSO$_3$-Fmoc)$_5$-colistin decapeptide

Solubilized deacylase enzyme, 940 mg, representing 400 mL original enzyme fermentation volume, prepared according to Example 2, was combined with 320 mL of 0.02 molar ammonium phosphate buffer, pH 7.2, 80 mL ethanol, 2.96 grams EDTA disodium salt and 200 mg (HSO$_3$-Fmoc)$_5$-colistin, prepared according to the procedure of Example 44. The mixture was adjusted to pH 8 and placed on a shaker at 140 rpm, 30° C. Progress of the deacylation was monitored by HPLC. After three hours the completed reaction was removed from the shaker and allowed to stand at room temperature for one hour before being adjusted to pH 2.0 with 1N HCl. The precipitate was mixed with 50 mL water, dissolved by adjusting to pH 6.46 and allowed to stand at 4° C. overnight resulting in a small amount of precipitate of the protected decapeptide. The precipitate was combined with methanol, which was then evaporated to dryness, re-dissolved in water and freeze-dried to obtain 12.5 mg of light tan powder, $C_{122}H_{134}N_{16}O_{37}S_5$. ESIMS: calc. m/z for $C_{122}H_{135}N_{16}O_{37}S_5Na$: $(M+H+Na)^{+2}$=1282.4. Found: 1282.2. The remaining decant was freeze-dried to obtain an additional 192 mg of tan powder, the protected colistin decapeptide.

Example 46

Other Peptides

Other novel peptides and novel protected peptides can be made by the methods described above. Any peptide having the common heptapeptide cyclic core structure of the polymyxins and the octapeptins, including, e.g., polymyxin A, polymyxin B (e.g., polymyxin B1, polymyxin B2, and polymyxin B3), [Ile$^7$]-polymyxin B$_1$, polymyxin C, polymyxin D, polymyxin E (also called colistin), polymyxin F, polymyxin M (also called mattacin), polymyxin P, polymyxin S, polymyxin T (e.g., polymyxin T1), colistin, circulin A, octapeptin A (e.g., octapeptin A1, octapeptin A2, and octapeptin A3) octapeptin B (e.g., octapeptin B1, octapeptin B2, and octapeptin B3), octapeptin C (e.g., octapeptin C1), and octapeptin D, can be amino protected as described in Example 1, deacylated as described in Examples 3 and 4, purified as in Example 5, modified as described in Examples 7 and 9, and subjected to Edman degradation as described in Example 8.

REFERENCES

1. Evans, M. E., Feola, D. J., Rapp, R. P. 1999. Polymyxin B Sulfate and Colistin: Old Antibiotics for Emerging Multi-resistant Gram-Negative Bacteria. Ann. Pharmacother. 33:960-967.
2. McCallister, S. M., Alpar H. O., Brown, M. R. W. 1999. Antimicrob. Chemother. 43:203-210.
3. Chihara, S., Ito, A., Yahata, M., Tobita, T., Koyama, Y. 1974. Chemical Synthesis and Characterization of n-Fattyacyl Mono-Aminoacyl Derivatives of Colistin Nonapeptide. Agr. Biol. Chem. 38: (10), 1767-1777.
4. Chihara, S., Ito, A., Yahata, M., Tobita, T., Koyama, Y. 1973. Chemical Synthesis and Characterization of a —N-Octanoyl and Other α-N-Acyl Nonapeptide Derivatives. Agr. Biol. Chem. 37: (12), 2709-2717.
5. Chichara, S., Ito, A., Yahata, M., Tobita, T., Koyama, Y. 1974. Chemical Synthesis, Isolation and Characterization of n-N-Fattyacyl Colistin Nonapepetide with Special Reference to the Correlation Between Antimicrobial Activity and Carbon Number of Fattyacyl Moiety. Agr. Biol. Chem. 38: (3), 521-529.
6. Weinstein, J., Afonso, A., Moss, E. JR., Miller, G. H. 1988. Selective Chemical Modifications of Polymyxin B. Biorg. Med. Chem. Lett. 8:3991-3996.
7. Tsubery, H., Ofek, I., Cohen, S., Fridkin, M. 2001. N-Terminal Modifications of Polymyxin B Nonapeptide and Their Effect on Antibacterial Activity. Peptides. 22: 1675-1681.
8. Mutter, M., and Bellof, D. 1984. A New Base-labile Anchoring Group for Polymer-supported peptide synthesis, Helv. Chim. Acta, 67, 2009.
9. Liu, Y.-Z., Ding, S. H., Chu, J.-Y. and Felix, A. M. 1990. A Novel Fmoc-based Anchorage for the Synthesis of protected Peptide on Solid Phase, Int. J. Pept. Protein Res., 35, 95.
10. Markou, N., Apostolakos, H., Koumoudiou, C., Anthanasiou, M., Koutsoukou, A., Alamanos, I., and Gregorakos, L. 2003. Intravenous colistin in the treatment of sepsis from multiresistant Gram-negative bacilli in critically ill patients, Critical Care 7, R78-R83.
11. Duwe, A. K., Rupar, C. A., Horsman, G. B., and Vas, S. I., 1986. In Vitro Cytotoxicity and Antibiotic Activity of Polymyxin B Nonapeptide, Antimicrob. Agents Chemother, 30:340-341.
12. Kurihara T., Takeda, H., and Ito, H. 1972. Compounds related to colistin. V. Synthesis and pharmacological activity of colistin analogs, Yakugaku Zasshi 92:129-34.
13. Parker, W. L., Rathnum, M. L., 1975. EM49, A New Peptide Antibiotic IV. The Structure of EM49. J. Antibiot. 28: (5), 379-389.
14. Hausmann, W., et al., 1954. Polymyxin B1. Fractionation, molecular-weight determination, amino acid and fatty acid composition, J. Am. Chem. Soc. 76, 4892-4896.
15. DeVisser Kriek, N. M. A. J., van Hooft, P. A. V., Van Schepdael A., Fillipov, D. V., van der Marel, G. A., Overcleeft, H. S., van Boom, J. H., and Noort, D. M. 2003. Synthesis of polymyxin B and analogues, J. Peptide Res. 61, 298-306.
16. Kimura, Y., Matsunaga, and Vaara, M., 1992. Polymyxin B Octapeptide and Polymyxin B Heptapeptide are Potent Outer Membrane Permeability-Increasing Agents. J. Antibiot., 45, 742-749.
17. Boeck, L. D., Fukuda, D. S., Abbott, B. J., Debono, M. 1988. Deacylation of A21978C, an acidic Lipopeptide Antibiotic Complex, by Actinoplanes utahensis. J. Antibiot. 41: (8), 1085-1092.
18. Kreuzman, A. J., Hodges, R. L., Swartling, J. R., Ghag, S. K., Baker, P. J., McGilvray, D., Yeh, W. K. 2000. Membrane-Associated Echinocandin B Deacylase of Actinoplanes utahensis: Purification, Characterization, Heterologous Cloning
19. Boeck, L. D., Fukuda, D. S., Abbott, B. J., Debono, M. 1989. Deacylation of Echinocandin B by Actinoplanes utahensis. J. Antibiot. 42: (3), 382-388.
20. Borders, D. B. Curran, W. V., Fantini, A., Francis, N. D., Jarolmen, H., Leese, R. A., 2003. Derivatives of Laspartomycin and Preparation and Use Thereof, U.S. Pat. No. 6,511,962.

21. Elverdam, I., Larsen, P., Lund, E. 1981. Isolation and Characterization of Three New Polymyxins in Polymyxins B and E by High-Performance Liquid Chromatography. *J. Chromatogr.* 218: 653-661.
22. Sakura, N., Itoh, T., Uchida, Y., Ohki, K., Okimura, K., Chiba, K., Sato, Y., Sawanishi, H. 2004. The Contribution of the N-Terminal Structure of Polymyxin B Peptides to Antimicrobial and Lipopolysaccharide Binding Activity, *Bull. Chem. Soc. Jpn.* 77: 1915-1924.
23. Falagas, M. E., Kasiakou, S. K. 2005. Colistin: The Revival of Polymyxins for the Management of Multidrug-Resistant Gram-Negative Bacterial Infections. *Rev. Anti-Infect. Agents.* 40: 1333-1341.
24. Salem, E. M., El-Gammal, A. A. 1980. Synthesis of Pelargonoyl-Cyclic Decapeptide Analog of the Antibiotic Polymyxin $B_1$. *Pharmazie* 35: 540-541.
25. Srinivasa, B. R., Ramachandran, L. K. 1980. Essential Amino Groups of Polymyxin B. *Indian J. Biochem. Biophys.* 17: 112-118.
26. Kline, T., Holub, D., Therrien, J., Leung, T., Ryckman, D. 2001. Synthesis and characterization of the colistin peptide polymyxin $E_1$ and related antimicrobial peptides. *J. Pept. Res.*, 57: 175-187.
27. Bouchaudon, J., Jolles, G. 1973. Cyclopeptides Derived From Polymyxins and Their Preparation. U.S. Pat. No. 3,753,970.
28. Shechter, Y., Preciado-Patt, L., Schreiber, G., Fridkin, M. 2001. Prolonging the half-life of human interferon-$\alpha_2$ in circulation: Design, preparation, and analysis of (2-sulfo-9-fluorenylmethoxycarbonyl)7-interferon-$\alpha_2$. *Proc. Natl. Acad. Sci., U.S.A.* 98: 1212-1217.
29. Merrifield, R. B., Bach, A. E. 1978. 9-(2-Sulfo)fluorenylmethyloxycarbonyl chloride, a new reagent for the purification of synthetic peptides. *J. Org. Chem.*, 43: 4808-4816.
30. Kleinkauf, H., van Dohren, H. 1990. Nonribosomal synthesis of peptide antibiotics. *Eur. J. Biochem.* 192: 1-15.
31. Martin, N. I., Hu, H., Moakes, M. M., Churey, J. J., Whittal, R., Worobo, R. W., Vederas, J. C. 2003. Isolation, structural characterization, and properties of mattacin (polymyxin M), a cyclic peptide antibiotic produced by *Paenibacillus kobensis* M. *J. Biol. Chem.* 278: 13124-13132.
32. Gershonov, E., Goldwaser, I., Fridkin, M., Schecter, Y, 2000, "A Novel Approach for a Water-Soluble Long-Acting Insulin Proprug: Design, Preparation, and Analysis of [(2-Sulfo)-9-Fluorenylmethoxycarbonyl]$_3$-Insulin," *J. Med. Chem.* 43: (13), 2530-2537, and
33. Schechter, Y., Tsudbery, H., Fridkin, M., 2002, N-[(2-Sulfo)-9-Fluorenylmethoxycarbonyl]$_3$-Gentamicin Is a Long-Acting Prodrug Derivative," *J. Med. Chem.* 45: (19), 4264-4270.

What is claimed is:

1. An antibiotic compound of the formula:

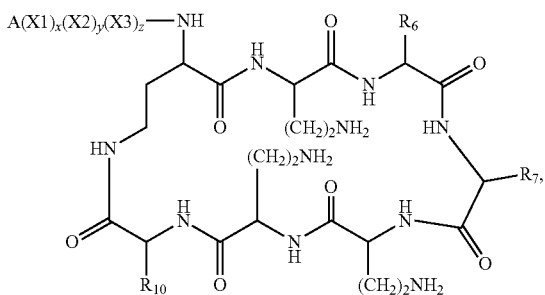

or a pharmaceutically acceptable salt thereof, wherein:
A is selected from R'—(C=O)-(p-aminophenylacetyl)-, R'—(C=O)-Lys-, R'—(C=O)-Phe-, R'—NH—(C=O)—, R'—NH(C=S)—, R'—$SO_2$—, R'—(C=NH)—, R'—O—$CH_2$—(C=O)—, R'—, R'-alkyl, R'—P(O)OH, R'—O—(C=S)—, R'—NH—(C=NH)—, and R'—(C=S)—;
R' is selected from aryl, heteroaryl, alkyl, alkenyl, heterocyclyl and cycloalkyl, wherein each aryl, heteroaryl, alkyl, alkenyl, heterocyclyl and cycloalkyl is optionally substituted with one or more groups selected from halogen, ($C_1$-$C_{20}$) alkyl, aryl, heteroaryl and aryloxy;
x and y are each independently 0 or 1;
z is 1;
X1 is selected from Dab, Phe, Ala, Lys and Gly;
X2 is Thr;
X3 is Dab; and
$R_6$, $R_7$ and $R_{10}$ are each independently selected from isopropyl, benzyl, isobutyl, sec-butyl, 1-hydroxy-1-ethyl, and hydroxymethyl.

2. The antibiotic compound of claim 1, or a pharmaceutically acceptable salt thereof, wherein A is selected from R'—(C=O)-(p-aminophenylacetyl)-, R'—(C=O)-Lys-, R'—(C=O)-Phe-, R'—NH—(C=O)—, R'—NH(C=S)—, R'—$SO_2$—, or R'—O—$CH_2$—(C=O)—.

3. The antibiotic compound of claim 1, or a pharmaceutically acceptable salt thereof, wherein A is selected from
R'—(C=O)-(p-aminophenylacetyl)-, wherein R' is alkyl;
R'—(C=O)-Lys-, wherein R' is alkyl;
R'—(C=O)-Phe-, wherein R' is alkyl;
R'—NH—(C=O)—, wherein R' is a) alkyl optionally substituted with aryl or heteroaryl; b) aryl optionally substituted with halogen, aryl, alkyl or aryloxy; or c) cycloalkyl;
R'—NH(C=S)—, wherein R' is aryl;
R'—$SO_2$—, wherein R' is a) alkyl or b) aryl optionally substituted with alkyl; and
R'—O—$CH_2$—(C=O)—, wherein R' is a) aryl or b) alkyl optionally substituted with aryl.

4. The antibiotic compound of claim 1, or a pharmaceutically acceptable salt thereof, wherein:
A is selected from R'—(C=O)-(p-aminophenylacetyl)-, R'—(C=O)-Lys-, R'—(C=O)-Phe-, R'—NH—(C=O)—, R'—NH(C=S)—, R'—$SO_2$— and R'—O—$CH_2$—(C=O)—, and R' is selected from phenyl, methylphenyl, benzyl, naphthyl, pyridinyl, indolylethyl, ($C_8$-$C_{10}$) alkyl, (n-$C_{10}H_{21}$)-phenyl, biphenyl, phenoxyphenyl, chlorophenyl, and cyclohexyl.

5. The antibiotic compound of claim 1, or a pharmaceutically acceptable salt thereof, wherein:
$R_6$ and $R_7$ are each independently selected from isopropyl, benzyl, isobutyl, sec-butyl, 1-hydroxy-1-ethyl, and hydroxymethyl; and
$R_{10}$ is selected from isopropyl, isobutyl, sec-butyl, 1-hydroxy-1-ethyl, and hydroxymethyl.

6. The antibiotic compound of claim 5, or a pharmaceutically acceptable salt thereof, wherein:
$R_6$ is benzyl or isobutyl;
$R_7$ is isobutyl or sec-butyl; and
$R_{10}$ is 1-hydroxy-1-ethyl.

7. The antibiotic compound of claim 6, or a pharmaceutically acceptable salt thereof, wherein $R_6$ is benzyl.

8. The antibiotic compound of claim 7, or a pharmaceutically acceptable salt thereof, wherein $R_7$ is isobutyl.

9. The antibiotic compound of claim 7, or a pharmaceutically acceptable salt thereof, wherein $R_7$ is sec-butyl.

10. The antibiotic compound of claim 6, or a pharmaceutically acceptable salt thereof, wherein $R_6$ is isobutyl and $R_7$ is isobutyl.

11. The antibiotic compound of claim 1, or a pharmaceutically acceptable salt thereof, wherein:
A is R'—NH—(C=O)—;
R' is phenyl with one hydrogen atom replaced by one chloro substituent;
$R_6$ is benzyl; and
$R_7$ is isobutyl or sec-butyl.

12. The antibiotic compound of claim 1, or a pharmaceutically acceptable salt thereof, wherein:
A is R'—NH(C=O);
R' is 4-Cl—$C_6H_4$—;
X1 is Dab;
X2 is Thr;
X3 is Dab;
$R_6$ is benzyl;
$R_7$ is isobutyl; and
$R_{10}$ is 1-hydroxy-1-ethyl.

13. The antibiotic compound of claim 1, or a pharmaceutically acceptable salt thereof, wherein x is 0.

14. The antibiotic compound of claim 1, or a pharmaceutically acceptable salt thereof, wherein x and y are each 0.

15. The antibiotic compound of claim 1, or a pharmaceutically acceptable salt thereof, wherein:
A is R'—NH(C=O)—;
R' is n-$C_8H_{17}$;
X1 is Dab;
X2 is Thr,
X3 is Dab;
$R_6$ is benzyl;
$R_7$ is isobutyl; and
$R_{10}$ is 1-hydroxy-1-ethyl.

16. The antibiotic compound of claim 1, or a pharmaceutically acceptable salt thereof, wherein:
A is R'—NH(C=S)—;
R' is phenyl;
X1 is Dab;
X2 is Thr,
X3 is Dab;
$R_6$ is benzyl;
$R_7$ is isobutyl; and
$R_{10}$ is 1-hydroxy-1-ethyl.

17. The antibiotic compound of claim 1, or a pharmaceutically acceptable salt thereof, wherein:
A is R'—NH(C=O)—;
R' is phenyl;
X1 is Dab;
X2 is Thr,
X3 is Dab;
$R_6$ is benzyl;
$R_7$ is isobutyl; and
$R_{10}$ is 1-hydroxy-1-ethyl.

18. The antibiotic compound of claim 2, or a pharmaceutically acceptable salt thereof, wherein:
A is R'—O—$CH_2$—(C=O)—;
R' is 2-naphthyl;
X1 is Dab;
X2 is Thr,
X3 is Dab;
$R_6$ is benzyl;
$R_7$ is isobutyl; and
$R_{10}$ is 1-hydroxy-1-ethyl.

19. The antibiotic compound of claim 1, or a pharmaceutically acceptable salt thereof, wherein:
A is R'—$SO_2$—;
R' is 4-$CH_3$—$C_6H_4$—;
X1 is Dab;
X2 is Thr,
X3 is Dab;
$R_6$ is benzyl;
$R_7$ is isobutyl; and
$R_{10}$ is 1-hydroxy-1-ethyl.

20. The antibiotic compound of claim 1, or a pharmaceutically acceptable salt thereof, wherein:
A is R'—(C=O)-Phe-;
R' is n-$C_9H_{19}$—;
X1 is Dab;
X2 is Thr,
X3 is Dab;
$R_6$ is benzyl;
$R_7$ is isobutyl; and
$R_{10}$ is 1-hydroxy-1-ethyl.

21. The antibiotic compound of claim 1, or a pharmaceutically acceptable salt thereof, wherein:
A is R'—O—$CH_2$—(C=O)—;
R' is $C_6H_5CH_2$—;
X1 is Dab;
X2 is Thr,
X3 is Dab;
$R_6$ is benzyl;
$R_7$ is isobutyl; and
$R_{10}$ is 1-hydroxy-1-ethyl.

22. The antibiotic compound of claim 1, or a pharmaceutically acceptable salt thereof, wherein:
A is R'—NH—(C=O)—;
R' is 4-($C_6H_5O)C_6H_4$—;
X1 is Dab;
X2 is Thr,
X3 is Dab;
$R_6$ is benzyl;
$R_7$ is isobutyl; and
$R_{10}$ is 1-hydroxy-1-ethyl.

23. The antibiotic compound of claim 1, or a pharmaceutically acceptable salt thereof, wherein:
A is R'—NH—(C=O)—;
R' is benzyl-;
X1 is Dab;
X2 is Thr,
X3 is Dab;
$R_6$ is benzyl;
$R_7$ is isobutyl; and
$R_{10}$ is 1-hydroxy-1-ethyl.

24. The antibiotic compound of claim 1, or a pharmaceutically acceptable salt thereof, wherein:
A is R'—NH—(C=O)—;
R' is cyclohexyl-;
X1 is Dab;
X2 is Thr,
X3 is Dab;
$R_6$ is benzyl;
$R_7$ is isobutyl; and
$R_{10}$ is 1-hydroxy-1-ethyl.

25. The antibiotic compound of claim 1, or a pharmaceutically acceptable salt thereof, wherein:
A is R'—NH—(C=O)—;
R' is cyclohexyl-;
X1 is Dab;
X2 is Thr,
X3 is Dab;
$R_6$ is benzyl;
$R_7$ is sec-butyl; and
$R_{10}$ is 1-hydroxy-1-ethyl.

26. The antibiotic compound of claim 1, or a pharmaceutically acceptable salt thereof, wherein:
A is R'—NH(C=O)—;
R' is n-$C_8H_{17}$;
X1 is Dab;
X2 is Thr,
X3 is Dab;
$R_6$ is isobutyl;
$R_7$ is isobutyl; and
$R_{10}$ is 1-hydroxy-1-ethyl.

27. The antibiotic compound of claim 1, or a pharmaceutically acceptable salt thereof, wherein:
A is R'—$SO_2$—;
R' is 4-$CH_3$—$C_6H_4$—;
X1 is Dab;
X2 is Thr,
X3 is Dab;
$R_6$ is isobutyl;
$R_7$ is isobutyl; and
$R_{10}$ is 1-hydroxy-1-ethyl.

28. The antibiotic compound of claim 1, or a pharmaceutically acceptable salt thereof, wherein:
A is R'—(C=O)-Lys-;
R' is n-$C_9H_{19}$;
X1 is Dab;
X2 is Thr;
X3 is Dab;
$R_6$ is benzyl;
$R_7$ is isobutyl; and
$R_{10}$ is 1-hydroxy-1-ethyl.

29. An antibiotic compound of the formula:

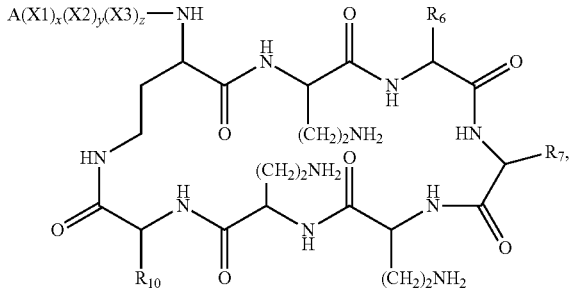

or a pharmaceutically acceptable salt thereof, wherein:
A is selected from R'—(C=O)-(p-aminophenylacetyl)-, R'—(C=O)-Lys-, R'—(C=O)-Phe-, R'—NH—(C=O)—, R'—NH(C=S)—, R'—$SO_2$—, R'—(C=NH)—, R'—O—$CH_2$—(C=O)—, R'—, R'-alkyl, R'—P(O)OH, R'—O—(C=S)—, R'—NH—(C=NH)—, and R'—(C=S)—;
R' is selected from aryl, heteroaryl, alkyl, alkenyl, heterocyclyl and cycloalkyl, wherein each aryl, heteroaryl, alkyl, alkenyl, heterocyclyl and cycloalkyl is optionally substituted with one or more groups selected from halogen, aryl, heteroaryl and aryloxy;
x, y, and z are each 1;
X1 is Dab;
X2 is Thr;
X3 is Dab; and
$R_6$, $R_7$ and $R_{10}$ are each independently selected from isopropyl, benzyl, isobutyl, sec-butyl, 1-hydroxy-1-ethyl, and hydroxymethyl.

30. The antibiotic compound of claim 29, or a pharmaceutically acceptable salt thereof, wherein A is selected from R'—(C=O)-(p-aminophenylacetyl)-, R'—(C=O)-Lys-, R'—(C=O)-Phe-, R'—NH—(C=O)—, R'—NH(C=S)—, R'—$SO_2$—, or R'—O—$CH_2$—(C=O)—.

31. The antibiotic compound of claim 29, or a pharmaceutically acceptable salt thereof, wherein A is selected from
R'—(C=O)-(p-aminophenylacetyl)-, wherein R' is alkyl;
R'—(C=O)-Lys-, wherein R' is alkyl;
R'—(C=O)-Phe-, wherein R' is alkyl;
R'—NH—(C=O)—, wherein R' is a) alkyl optionally substituted with aryl or heteroaryl; b) aryl optionally substituted with halogen, aryl, alkyl or aryloxy; or c) cycloalkyl;
R'—NH(C=S)—, wherein R' is aryl;
R'—$SO_2$—, wherein R' is a) alkyl or b) aryl optionally substituted with alkyl; and
R'—O—$CH_2$—(C=O)—, wherein R' is a) aryl or b) alkyl optionally substituted with aryl.

32. The antibiotic compound of claim 29, or a pharmaceutically acceptable salt thereof, wherein:
A is selected from R'—(C=O)-(p-aminophenylacetyl)-, R'—(C=O)-Lys-, R'—(C=O)-Phe-, R'—NH—(C=O)—, R'—NH(C=S)—, R'—$SO_2$— and R'—O—$CH_2$—(C=O)—, and R' is selected from phenyl, methylphenyl, benzyl, naphthyl, pyridinyl, indolylethyl, ($C_8$-$C_{10}$)alkyl, (n-$C_{10}H_{21}$)-phenyl, biphenyl, phenoxyphenyl, chlorophenyl, and cyclohexyl.

33. The antibiotic compound of claim 29, or a pharmaceutically acceptable salt thereof, wherein:
$R_6$ and $R_7$ are each independently selected from isopropyl, benzyl, isobutyl, sec-butyl, 1-hydroxy-1-ethyl, and hydroxymethyl; and
$R_{10}$ is selected from isopropyl, isobutyl, sec-butyl, 1-hydroxy-1-ethyl, and hydroxymethyl.

34. The antibiotic compound of claim 33, or a pharmaceutically acceptable salt thereof, wherein:
$R_6$ is benzyl or isobutyl;
$R_7$ is isobutyl or sec-butyl; and
$R_{10}$ is 1-hydroxy-1-ethyl.

35. The antibiotic compound of claim 34, or a pharmaceutically acceptable salt thereof, wherein $R_6$ is benzyl.

36. The antibiotic compound of claim 35, or a pharmaceutically acceptable salt thereof, wherein $R_7$ is isobutyl.

37. The antibiotic compound of claim 35, or a pharmaceutically acceptable salt thereof, wherein $R_7$ is sec-butyl.

38. The antibiotic compound of claim 34, or a pharmaceutically acceptable salt thereof, wherein $R_6$ is isobutyl and $R_7$ is isobutyl.

39. An antibiotic compound of the formula:

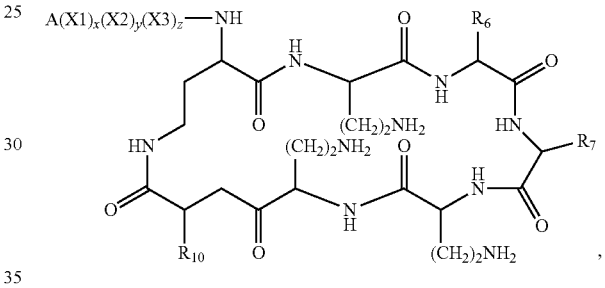

or a pharmaceutically acceptable salt thereof, wherein:
A is R'—O—(C=O)— and R' is selected from aryl, heteroaryl, alkyl, alkenyl, heterocyclyl and cycloalkyl, wherein each aryl, heteroaryl, alkyl, alkenyl, heterocyclyl and cycloalkyl is optionally substituted with one or more groups selected from halogen, ($C_1$-$C_{20}$) alkyl, ($C_6$-$C_{10}$) aryl, heteroaryl and aryloxy;
or
A is R'—O—(C=O)— and R' is selected from unsubstituted, linear alkyl having at least 9 carbon atoms cycloalkyl, alkenyl, aryl, heteroaryl, heterocyclyl, and substituted alkyl, wherein at least one hydrogen on said substituted alkyl is replaced by a substituted group selected from halogen, aryl, heteroaryl, alkoxy and aryloxy;
x and y are each independently 0 or 1;
z is 1;
X1 is Thr;
X2 is Dab; and
$R_6$, $R_7$ and $R_{10}$ are each independently selected from isopropyl, benzyl, isobutyl, sec-butyl, 1-hydroxy-1-ethyl, and hydroxymethyl,
provided that when $R_6$ and $R_7$ are each isobutyl and $R_{10}$ is 1-hydroxy-1-ethyl, then x and Y are each 1 and X1 is Dab.

40. The antibiotic compound of claim 39, or a pharmaceutically acceptable salt thereof, wherein A is R' —(C=O)— and R' is an unsubstituted alkyl having at least 9 carbon atoms, cycloalkyl, aryl, heteroaryl, or substituted alkyl, wherein at least one hydrogen on said substituted alkyl is replaced by a substituent group selected from halogen, aryl, heteroaryl, alkoxy, and aryloxy.

41. The antibiotic compound of claim 39, or a pharmaceutically acceptable salt thereof, wherein A is R'—(C=O)— and R' is selected from $C_9$-alkyl, phenyl, pyridinyl and alkyl substituted with an aryl, alkoxy, or aryloxy group.

42. The antibiotic compound of claim 39, or a pharmaceutically acceptable salt thereof, wherein:
$R_6$ and $R_7$ are each independently selected from isopropyl, benzyl, isobutyl, sec-butyl, 1-hydroxy-1-ethyl, and hydroxymethyl; and
$R_{10}$ is selected from isopropyl, isobutyl, sec-butyl, 1-hydroxy-1-ethyl, and hydroxymethyl.

43. The antibiotic compound of claim 42, or a pharmaceutically acceptable salt thereof, wherein:
$R_6$ is benzyl or isobutyl;
$R_7$ is isobutyl or sec-butyl; and
$R_{10}$ is 1-hydroxy-1-ethyl.

44. The antibiotic compound of claim 43, or a pharmaceutically acceptable salt thereof, wherein $R_6$ is benzyl.

45. The antibiotic compound of claim 44, or a pharmaceutically acceptable salt thereof, wherein $R_7$ is isobutyl.

46. The antibiotic compound of claim 45, or a pharmaceutically acceptable salt thereof, wherein:
R' is n-$C_9H_{19}$—;
x, y, and z are each 1; and
X1 is selected from Dab, Lys, and Phe.

47. The antibiotic compound of claim 44, or a pharmaceutically acceptable salt thereof, wherein $R_7$ is sec-butyl.

48. The antibiotic compound of claim 43, or a pharmaceutically acceptable salt thereof, wherein $R_6$ is isobutyl and $R_7$ is isobutyl.

49. The antibiotic compound of claim 39, or a pharmaceutically acceptable salt thereof, wherein x is 0 and y is 1.

50. The antibiotic compound of claim 39, or a pharmaceutically acceptable salt thereof, wherein x and y are each 0.

51. The antibiotic compound of claim 50, or a pharmaceutically acceptable salt thereof, wherein R' is n-$C_9$-alkyl.

52. An antibiotic compound of the formula:

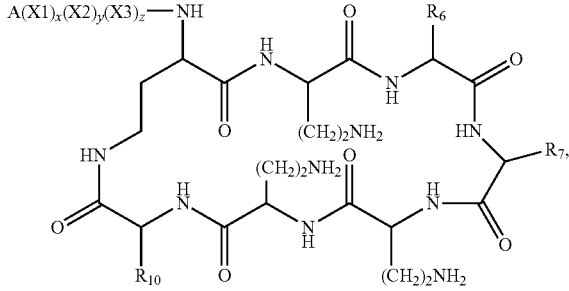

or a pharmaceutically acceptable salt thereof, wherein:
A is R'—(C=O)— and R' is selected from unsubstituted, linear alkyl having at least 9 carbon atoms, cycloalkyl, alkenyl, aryl, heteroaryl, heterocyclyl, and substituted alkyl, wherein at least one hydrogen on said substituted alkyl is replaced by a substituent group selected from halogen, aryl, heteroaryl, alkoxy, and aryloxy;
x, y, and z are each 1;
X1 is Dab;
X2 is Thr;
X3 is Dab; and
$R_6$, $R_7$ and $R_{10}$ are each independently selected from isopropyl, benzyl, isobutyl, sec-butyl, 1-hydroxy-1-ethyl, and hydroxymethyl.

53. The antibiotic compound of claim 52, or a pharmaceutically acceptable salt thereof, wherein:
$R_6$ is benzyl or isobutyl;
$R_7$ is isobutyl or sec-butyl; and
$R_{10}$ is 1-hydroxy-1-ethyl.

54. The antibiotic compound of claim 53, or a pharmaceutically acceptable salt thereof, wherein $R_6$ is benzyl.

55. The antibiotic compound of claim 54, or a pharmaceutically acceptable salt thereof, wherein R' is n-$C_9$-alkyl.

56. The antibiotic compound of claim 54, or a pharmaceutically acceptable salt thereof, wherein R' is an alkyl substituted with a group selected from N-($C_1$-$C_{10}$-alkyl)-4-aminophenyl and benzyloxy.

57. The antibiotic compound of claim 54, or a pharmaceutically acceptable salt thereof, wherein R' is selected from phenyl, 4-pyridinyl, and alkyl substituted with a 2-naphthoxy group.

58. The antibiotic compound of claim 54, or a pharmaceutically acceptable salt thereof, wherein $R_7$ is isobutyl.

59. The antibiotic compound of claim 58, or a pharmaceutically acceptable salt thereof, wherein R' is phenyl.

60. The antibiotic compound of claim 54, or a pharmaceutically acceptable salt thereof, wherein $R_7$ is sec-butyl.

61. The antibiotic compound of claim 53, or a pharmaceutically acceptable salt thereof, wherein $R_6$ is isobutyl and $R_7$ is isobutyl.

62. A method for preparing a compound, the method comprising:
(a) treating a polymyxin peptide having a sidechain comprising an amino group with an amino protecting group reagent to form a protected polymyxin peptide, wherein the polymyxin peptide comprises a cyclic heptapeptide attached to an exocyclic peptide chian comprising an acyl group, and the protecting group comprises at least one acidic substituent;
(b) reacting the protected peptide with a deacylase enzyme in an aqueous solution to form a protected, deacylated peptide comprising a free amino terminus on the exocyclic peptide chain; and
(c) reacting the free amino terminus on the exocyclic peptide chain of the protected, deacylated peptide with an addition reagent and removing the protecting group to form a peptide antibiotic having the following formula:

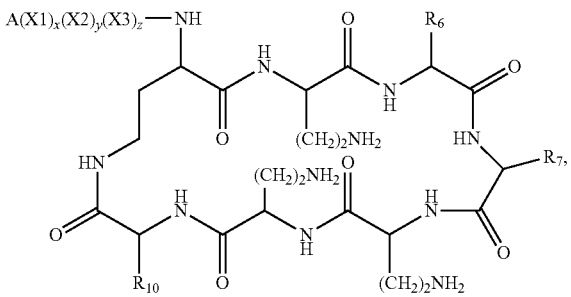

wherein
A is R'—O—(C=O)— and R' is selected from aryl, heteroaryl, alkyl, alkenyl, heterocyclyl and cycloalkyl, wherein each aryl, heteroaryl, alkyl, alkenyl, heterocyclyl and cycloalkyl is optionally substituted with one or more groups selected from halogen, ($C_1$-$C_{20}$) alkyl, ($C_6$-$C_{10}$) aryl, heteroaryl and aryloxy;
A is R'—(C=O)— and R' is selected from unsubstituted, linear alkyl having at least 9 carbon atoms cycloalkyl, alkenyl, aryl, heteroaryl, heterocyclyl, and substituted alkyl, wherein at least one hydrogen on said substituted alkyl is replaced by a substituted group selected from halogen, aryl, heteroaryl, alkoxy and aryloxy;
x and y are each independently 0 or 1;
z is 1;
X1 is Thr;
X2 is Dab; and
$R_6$, $R_7$ and $R_{10}$ are each independently selected from isopropyl, benzyl, isobutyl, sec-butyl, 1-hydroxy-1-ethyl, and hydroxymethyl, provided that when $R_6$ and $R_7$ are each isobutyl and $R_{10}$ is 1-hydroxy-1-ethyl, then x and Y are each 1 and X1 is Dab.

63. The method of claim 62, wherein the protecting group is a sulfonic acid of 9-fluorenylmethoxycarbonyl.

64. The method of claim 63, wherein a source of the deacylase enzyme is *Actinoplanes utahensis*.

* * * * *

UNITED STATES PATENT AND TRADEMARK OFFICE
CERTIFICATE OF CORRECTION

PATENT NO. : 8,889,826 B2  
APPLICATION NO. : 11/630847  
DATED : November 18, 2014  
INVENTOR(S) : Richard A. Leese et al.

Page 1 of 1

It is certified that error appears in the above-identified patent and that said Letters Patent is hereby corrected as shown below:

In the Claims

Claim 39, column 94, lines 25-35, delete the incorrect formula and insert the correct formula below.

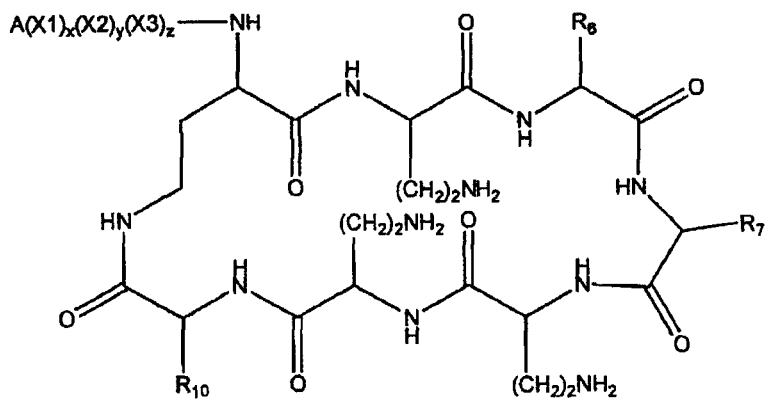

-- --

Signed and Sealed this  
Twenty-eighth Day of April, 2015

Michelle K. Lee  
*Director of the United States Patent and Trademark Office*